US012588907B2

(12) United States Patent
Tennenbaum

(10) Patent No.: US 12,588,907 B2
(45) Date of Patent: Mar. 31, 2026

(54) SELF-LOCKING WINCH

(71) Applicant: Edwards Lifesciences Innovation (Israel) Ltd., Caesarea (IL)

(72) Inventor: Gad Tennenbaum, Kiryat Ono (IL)

(73) Assignee: Edwards Lifesciences Innovation (Israel) Ltd., Caesarea (IL)

( * ) Notice: Subject to any disclaimer, the term of this patent is extended or adjusted under 35 U.S.C. 154(b) by 759 days.

(21) Appl. No.: 17/951,045

(22) Filed: Sep. 22, 2022

(65) Prior Publication Data

US 2023/0016867 A1     Jan. 19, 2023

Related U.S. Application Data

(63) Continuation of application No. PCT/IB2021/051902, filed on Mar. 8, 2021.

(60) Provisional application No. 62/993,669, filed on Mar. 23, 2020.

(51) Int. Cl.
*A61F 2/24* (2006.01)
*A61B 17/064* (2006.01)
*A61B 17/068* (2006.01)

(52) U.S. Cl.
CPC .......... *A61B 17/064* (2013.01); *A61B 17/068* (2013.01); *A61F 2/2442* (2013.01)

(58) Field of Classification Search
CPC .... A61F 2/2442; A61F 2/2445; A61F 2/2448; A61B 17/064; A61B 17/068
See application file for complete search history.

(56) References Cited

U.S. PATENT DOCUMENTS

| | | | |
|---|---|---|---|
| 3,604,488 | A | 9/1971 | Wishart et al. |
| 3,656,185 | A | 4/1972 | Carpentier |
| 3,840,018 | A | 10/1974 | Heifetz |
| 3,881,366 | A | 5/1975 | Bradley et al. |

(Continued)

FOREIGN PATENT DOCUMENTS

| | | | | |
|---|---|---|---|---|
| CA | 3092566 A1 | * | 9/2019 | ......... A61B 17/0401 |
| CN | 113331995 A | | 9/2021 | |

(Continued)

OTHER PUBLICATIONS

Agarwal et al. International Cardiology Perspective Functional Tricuspid Regurgitation, Circ Cardiovasc Interv 2009;2;2;565-573 (2009).

(Continued)

*Primary Examiner* — Alvin J Stewart
(74) *Attorney, Agent, or Firm* — Anya Adams

(57) ABSTRACT
A system includes a transcatheterally-advanceable driver and an implant. The implant includes a winch, and a tether that has an end portion. The winch includes a spool, a mount, and a driver interface engageable and drivable by the driver. The mount is coupled to the driver interface such that driving of the driver interface by the driver rotates the mount about a rotation axis. The spool is coupled to the tether, and defines a spool axis that is non-coaxial with the rotation axis. The tether extends away from the winch toward the end portion. The spool is fixedly coupled to the mount such that rotation of the mount about the rotation axis draws the end portion of the tether toward the spool by winding the tether around the spool axis of the spool. Other embodiments are also described.

20 Claims, 21 Drawing Sheets

(56) References Cited

U.S. PATENT DOCUMENTS

| | | | |
|---|---|---|---|
| 3,898,701 A | 8/1975 | La Russa |
| 4,042,979 A | 8/1977 | Angell |
| 4,118,805 A | 10/1978 | Reimels |
| 4,214,349 A | 7/1980 | Munch |
| 4,261,342 A | 4/1981 | Aranguren Duo |
| 4,290,151 A | 9/1981 | Massana |
| 4,434,828 A | 3/1984 | Trincia |
| 4,473,928 A | 10/1984 | Johnson |
| 4,602,911 A | 7/1986 | Ahmadi et al. |
| 4,625,727 A | 12/1986 | Leiboff |
| 4,712,549 A | 12/1987 | Peters et al. |
| 4,778,468 A | 10/1988 | Hunt et al. |
| 4,917,698 A | 4/1990 | Carpentier et al. |
| 4,935,027 A | 6/1990 | Yoon |
| 4,961,738 A | 10/1990 | Mackin |
| 5,042,707 A | 8/1991 | Taheri |
| 5,061,277 A | 10/1991 | Carpentier et al. |
| 5,064,431 A | 11/1991 | Gilbertson et al. |
| 5,104,407 A | 4/1992 | Lam et al. |
| 5,108,420 A | 4/1992 | Marks |
| 5,201,880 A | 4/1993 | Wright et al. |
| 5,258,008 A | 11/1993 | Wilk |
| 5,300,034 A | 4/1994 | Behnke et al. |
| 5,325,845 A | 7/1994 | Adair |
| 5,346,498 A | 9/1994 | Greelis et al. |
| 5,383,852 A | 1/1995 | Stevens-Wright |
| 5,449,368 A | 9/1995 | Kuzmak |
| 5,450,860 A | 9/1995 | O'Connor |
| 5,464,404 A | 11/1995 | Abela et al. |
| 5,474,518 A | 12/1995 | Farrer Velazquez |
| 5,477,856 A | 12/1995 | Lundquist |
| 5,593,424 A | 1/1997 | Northrup, III |
| 5,601,572 A | 2/1997 | Middleman et al. |
| 5,626,609 A | 5/1997 | Zvenyatsky et al. |
| 5,643,317 A | 7/1997 | Pavcnik et al. |
| 5,669,919 A | 9/1997 | Sanders et al. |
| 5,676,653 A | 10/1997 | Taylor et al. |
| 5,683,402 A | 11/1997 | Cosgrove et al. |
| 5,702,397 A | 12/1997 | Goble et al. |
| 5,702,398 A | 12/1997 | Tarabishy |
| 5,709,695 A | 1/1998 | Northrup, III |
| 5,716,370 A | 2/1998 | Williamson, IV et al. |
| 5,716,397 A | 2/1998 | Myers |
| 5,728,116 A | 3/1998 | Rosenman |
| 5,730,150 A | 3/1998 | Peppel et al. |
| 5,749,371 A | 5/1998 | Zadini et al. |
| 5,752,963 A | 5/1998 | Allard et al. |
| 5,782,844 A | 7/1998 | Yoon et al. |
| 5,810,882 A | 9/1998 | Bolduc et al. |
| 5,824,066 A | 10/1998 | Gross |
| 5,830,221 A | 11/1998 | Stein et al. |
| 5,843,120 A | 12/1998 | Israel et al. |
| 5,855,614 A | 1/1999 | Stevens et al. |
| 5,876,373 A | 3/1999 | Giba et al. |
| 5,935,098 A | 8/1999 | Blaisdell et al. |
| 5,957,953 A | 9/1999 | DiPoto et al. |
| 5,961,440 A | 10/1999 | Schweich, Jr. et al. |
| 5,961,539 A | 10/1999 | Northrup, III et al. |
| 5,984,959 A | 11/1999 | Robertson et al. |
| 5,993,459 A | 11/1999 | Arsen et al. |
| 6,042,554 A | 3/2000 | Rosenman et al. |
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |
| 6,074,341 A | 6/2000 | Anderson et al. |
| 6,074,401 A | 6/2000 | Gardiner et al. |
| 6,074,417 A | 6/2000 | Peredo |
| 6,086,582 A | 7/2000 | Altman et al. |
| 6,102,945 A | 8/2000 | Campbell |
| 6,106,550 A | 8/2000 | Magovern et al. |
| 6,110,200 A | 8/2000 | Hinnenkamp |
| 6,132,390 A | 10/2000 | Cookston et al. |
| 6,143,024 A | 11/2000 | Campbell et al. |
| 6,159,240 A | 12/2000 | Sparer et al. |
| 6,165,119 A | 12/2000 | Schweich, Jr. et al. |
| 6,174,332 B1 | 1/2001 | Loch et al. |
| 6,183,411 B1 | 2/2001 | Mortier et al. |
| 6,187,040 B1 | 2/2001 | Wright |
| 6,210,347 B1 | 4/2001 | Forsell |
| 6,217,610 B1 | 4/2001 | Carpentier et al. |
| 6,228,032 B1 | 5/2001 | Eaton et al. |
| 6,231,602 B1 | 5/2001 | Carpentier et al. |
| 6,251,092 B1 | 6/2001 | Qin et al. |
| 6,296,656 B1 | 10/2001 | Bolduc et al. |
| 6,315,784 B1 | 11/2001 | Djurovic |
| 6,319,281 B1 | 11/2001 | Patel |
| 6,328,746 B1 | 12/2001 | Gambale |
| 6,332,893 B1 | 12/2001 | Mortier et al. |
| 6,355,030 B1 | 3/2002 | Aldrich et al. |
| 6,361,559 B1 | 3/2002 | Houser et al. |
| 6,368,348 B1 | 4/2002 | Gabbay |
| 6,402,780 B2 | 6/2002 | Williamson, IV et al. |
| 6,406,420 B1 | 6/2002 | McCarthy et al. |
| 6,406,493 B1 | 6/2002 | Tu et al. |
| 6,419,696 B1 | 7/2002 | Ortiz et al. |
| 6,451,054 B1 | 9/2002 | Stevens |
| 6,458,076 B1 | 10/2002 | Pruitt |
| 6,461,336 B1 | 10/2002 | Larre |
| 6,461,366 B1 | 10/2002 | Seguin |
| 6,470,892 B1 | 10/2002 | Forsell |
| 6,503,274 B1 | 1/2003 | Howanec, Jr. et al. |
| 6,524,338 B1 | 2/2003 | Gundry |
| 6,527,780 B1 | 3/2003 | Wallace et al. |
| 6,530,952 B2 | 3/2003 | Vesely |
| 6,533,772 B1 | 3/2003 | Sherts et al. |
| 6,537,314 B2 | 3/2003 | Langberg et al. |
| 6,547,801 B1 | 4/2003 | Dargent et al. |
| 6,554,845 B1 | 4/2003 | Fleenor et al. |
| 6,564,805 B2 | 5/2003 | Garrison et al. |
| 6,565,603 B2 | 5/2003 | Cox |
| 6,569,198 B1 | 5/2003 | Wilson et al. |
| 6,579,297 B2 | 6/2003 | Bicek et al. |
| 6,589,160 B2 | 7/2003 | Schweich, Jr. et al. |
| 6,592,593 B1 | 7/2003 | Parodi et al. |
| 6,602,288 B1 | 8/2003 | Cosgrove et al. |
| 6,602,289 B1 | 8/2003 | Colvin et al. |
| 6,613,078 B1 | 9/2003 | Barone |
| 6,613,079 B1 | 9/2003 | Wolinsky et al. |
| 6,619,291 B2 | 9/2003 | Hlavka et al. |
| 6,626,899 B2 | 9/2003 | Houser et al. |
| 6,626,917 B1 | 9/2003 | Craig |
| 6,626,930 B1 | 9/2003 | Allen et al. |
| 6,629,534 B1 | 10/2003 | St. Goar et al. |
| 6,629,921 B1 | 10/2003 | Schweich, Jr. et al. |
| 6,651,671 B1 | 11/2003 | Donlon et al. |
| 6,652,556 B1 | 11/2003 | VanTassel et al. |
| 6,682,558 B2 | 1/2004 | Tu et al. |
| 6,689,125 B1 | 2/2004 | Keith et al. |
| 6,689,164 B1 | 2/2004 | Seguin |
| 6,695,866 B1 | 2/2004 | Kuehn et al. |
| 6,702,826 B2 | 3/2004 | Liddicoat et al. |
| 6,702,846 B2 | 3/2004 | Mikus et al. |
| 6,706,065 B2 | 3/2004 | Langberg et al. |
| 6,709,385 B2 | 3/2004 | Forsell |
| 6,709,456 B2 | 3/2004 | Langberg et al. |
| 6,711,444 B2 | 3/2004 | Koblish |
| 6,719,786 B2 | 4/2004 | Ryan et al. |
| 6,723,038 B1 | 4/2004 | Schroeder et al. |
| 6,726,716 B2 | 4/2004 | Marquez |
| 6,726,717 B2 | 4/2004 | Alfieri et al. |
| 6,749,630 B2 | 6/2004 | McCarthy et al. |
| 6,752,813 B2 | 6/2004 | Goldfarb et al. |
| 6,764,310 B1 | 7/2004 | Ichihashi et al. |
| 6,764,510 B2 | 7/2004 | Vidlund et al. |
| 6,764,810 B2 | 7/2004 | Ma et al. |
| 6,770,083 B2 | 8/2004 | Seguin |
| 6,786,924 B2 | 9/2004 | Ryan et al. |
| 6,786,925 B1 | 9/2004 | Schoon et al. |
| 6,790,231 B2 | 9/2004 | Liddicoat et al. |
| 6,797,001 B2 | 9/2004 | Mathis et al. |
| 6,797,002 B2 | 9/2004 | Spence et al. |
| 6,802,319 B2 | 10/2004 | Stevens et al. |
| 6,805,710 B2 | 10/2004 | Bolling et al. |
| 6,805,711 B2 | 10/2004 | Quijano et al. |

(56) References Cited

U.S. PATENT DOCUMENTS

| | | | |
|---|---|---|---|
| 6,855,126 B2 | 2/2005 | Flinchbaugh | |
| 6,858,039 B2 | 2/2005 | McCarthy | |
| 6,884,250 B2 | 4/2005 | Monassevitch et al. | |
| 6,893,459 B1 | 5/2005 | Macoviak | |
| 6,908,478 B2 | 6/2005 | Alferness et al. | |
| 6,908,482 B2 | 6/2005 | McCarthy et al. | |
| 6,918,917 B1 | 7/2005 | Nguyen et al. | |
| 6,926,730 B1 | 8/2005 | Nguyen et al. | |
| 6,960,217 B2 | 11/2005 | Bolduc | |
| 6,976,995 B2 | 12/2005 | Mathis et al. | |
| 6,986,775 B2 | 1/2006 | Morales et al. | |
| 6,989,028 B2 | 1/2006 | Lashinski et al. | |
| 6,997,951 B2 | 2/2006 | Solem et al. | |
| 7,004,176 B2 | 2/2006 | Lau | |
| 7,007,798 B2 | 3/2006 | Happonen et al. | |
| 7,011,669 B2 | 3/2006 | Kimblad | |
| 7,011,682 B2 | 3/2006 | Lashinski et al. | |
| 7,018,406 B2 | 3/2006 | Seguin et al. | |
| 7,037,334 B1 | 5/2006 | Hlavka et al. | |
| 7,077,850 B2 | 7/2006 | Kortenbach | |
| 7,077,862 B2 | 7/2006 | Vidlund et al. | |
| 7,087,064 B1 | 8/2006 | Hyde | |
| 7,101,395 B2 | 9/2006 | Tremulis et al. | |
| 7,101,396 B2 | 9/2006 | Artof et al. | |
| 7,112,207 B2 | 9/2006 | Allen et al. | |
| 7,118,595 B2 | 10/2006 | Ryan et al. | |
| 7,125,421 B2 | 10/2006 | Tremulis et al. | |
| 7,150,737 B2 | 12/2006 | Purdy et al. | |
| 7,159,593 B2 | 1/2007 | McCarthy et al. | |
| 7,166,127 B2 | 1/2007 | Spence et al. | |
| 7,169,187 B2 | 1/2007 | Datta et al. | |
| 7,172,625 B2 | 2/2007 | Shu et al. | |
| 7,175,660 B2 | 2/2007 | Cartledge et al. | |
| 7,186,262 B2 | 3/2007 | Saadat | |
| 7,186,264 B2 | 3/2007 | Liddicoat et al. | |
| 7,189,199 B2 | 3/2007 | McCarthy et al. | |
| 7,192,443 B2 | 3/2007 | Solem et al. | |
| 7,220,277 B2 | 5/2007 | Arru et al. | |
| 7,226,467 B2 | 6/2007 | Lucatero et al. | |
| 7,226,477 B2 | 6/2007 | Cox | |
| 7,226,647 B2 | 6/2007 | Kasperchik et al. | |
| 7,229,452 B2 | 6/2007 | Kayan | |
| 7,238,191 B2 | 7/2007 | Bachmann | |
| 7,288,097 B2 | 10/2007 | Seguin | |
| 7,294,148 B2 | 11/2007 | McCarthy | |
| 7,311,728 B2 | 12/2007 | Solem et al. | |
| 7,311,729 B2 | 12/2007 | Mathis et al. | |
| 7,314,485 B2 | 1/2008 | Mathis | |
| 7,316,710 B1 | 1/2008 | Cheng et al. | |
| 7,329,279 B2 | 2/2008 | Haug et al. | |
| 7,329,280 B2 | 2/2008 | Bolling et al. | |
| 7,335,213 B1 | 2/2008 | Hyde et al. | |
| 7,361,190 B2 | 4/2008 | Shaoulian et al. | |
| 7,364,588 B2 | 4/2008 | Mathis et al. | |
| 7,377,941 B2 | 5/2008 | Rhee et al. | |
| 7,390,329 B2 | 6/2008 | Westra et al. | |
| 7,404,824 B1 | 7/2008 | Webler et al. | |
| 7,431,692 B2 | 10/2008 | Zollinger et al. | |
| 7,442,207 B2 | 10/2008 | Rafiee | |
| 7,452,376 B2 | 11/2008 | Lim et al. | |
| 7,455,690 B2 | 11/2008 | Cartledge et al. | |
| 7,485,142 B2 | 2/2009 | Milo | |
| 7,485,143 B2 | 2/2009 | Webler et al. | |
| 7,500,989 B2 | 3/2009 | Solem et al. | |
| 7,507,252 B2 | 3/2009 | Lashinski et al. | |
| 7,510,575 B2 | 3/2009 | Spenser et al. | |
| 7,510,577 B2 | 3/2009 | Moaddeb et al. | |
| 7,527,647 B2 | 5/2009 | Spence | |
| 7,530,995 B2 | 5/2009 | Quijano et al. | |
| 7,549,983 B2 | 6/2009 | Roue et al. | |
| 7,559,936 B2 | 7/2009 | Levine | |
| 7,562,660 B2 | 7/2009 | Saadat | |
| 7,563,267 B2 | 7/2009 | Goldfarb et al. | |
| 7,563,273 B2 | 7/2009 | Goldfarb et al. | |
| 7,569,062 B1 | 8/2009 | Kuehn et al. | |
| 7,585,321 B2 | 9/2009 | Cribier | |
| 7,588,582 B2 | 9/2009 | Starksen et al. | |
| 7,591,826 B2 | 9/2009 | Alferness et al. | |
| 7,604,646 B2 | 10/2009 | Goldfarb et al. | |
| 7,608,091 B2 | 10/2009 | Goldfarb et al. | |
| 7,608,103 B2 | 10/2009 | McCarthy | |
| 7,618,449 B2 | 11/2009 | Tremulis et al. | |
| 7,625,403 B2 | 12/2009 | Krivoruchko | |
| 7,632,303 B1 | 12/2009 | Stalker et al. | |
| 7,635,329 B2 | 12/2009 | Goldfarb et al. | |
| 7,635,386 B1 | 12/2009 | Gammie | |
| 7,655,015 B2 | 2/2010 | Goldfarb et al. | |
| 7,666,204 B2 | 2/2010 | Thornton et al. | |
| 7,682,319 B2 | 3/2010 | Martin et al. | |
| 7,682,369 B2 | 3/2010 | Seguin | |
| 7,686,822 B2 | 3/2010 | Shayani | |
| 7,699,892 B2 | 4/2010 | Rafiee et al. | |
| 7,704,269 B2 | 4/2010 | St. Goar et al. | |
| 7,704,277 B2 | 4/2010 | Zakay et al. | |
| 7,722,666 B2 | 5/2010 | Afontaine | |
| 7,736,388 B2 | 6/2010 | Goldfarb et al. | |
| 7,748,389 B2 | 7/2010 | Salahieh et al. | |
| 7,753,924 B2 | 7/2010 | Starksen et al. | |
| 7,758,632 B2 | 7/2010 | Hojeibane et al. | |
| 7,780,726 B2 | 8/2010 | Seguin | |
| 7,871,368 B2 | 1/2011 | Zollinger et al. | |
| 7,871,433 B2 | 1/2011 | Lattouf | |
| 7,883,475 B2 | 2/2011 | Dupont et al. | |
| 7,883,538 B2 | 2/2011 | To et al. | |
| 7,892,281 B2 | 2/2011 | Seguin et al. | |
| 7,927,370 B2 | 4/2011 | Webler et al. | |
| 7,927,371 B2 | 4/2011 | Navia et al. | |
| 7,942,927 B2 | 5/2011 | Kaye et al. | |
| 7,947,056 B2 | 5/2011 | Griego et al. | |
| 7,955,315 B2 | 6/2011 | Feinberg et al. | |
| 7,955,377 B2 | 6/2011 | Melsheimer | |
| 7,981,152 B1 | 7/2011 | Webler et al. | |
| 7,992,567 B2 | 8/2011 | Hirotsuka et al. | |
| 7,993,368 B2 | 8/2011 | Gambale et al. | |
| 7,993,397 B2 | 8/2011 | Lashinski et al. | |
| 8,012,201 B2 | 9/2011 | Lashinski et al. | |
| 8,034,103 B2 | 10/2011 | Burriesci et al. | |
| 8,052,592 B2 | 11/2011 | Goldfarb et al. | |
| 8,057,493 B2 | 11/2011 | Goldfarb et al. | |
| 8,062,355 B2 | 11/2011 | Figulla et al. | |
| 8,070,804 B2 | 12/2011 | Hyde et al. | |
| 8,070,805 B2 | 12/2011 | Vidlund et al. | |
| 8,075,616 B2 | 12/2011 | Solem et al. | |
| 8,100,964 B2 | 1/2012 | Spence | |
| 8,123,801 B2 | 2/2012 | Milo | |
| 8,142,493 B2 | 3/2012 | Spence et al. | |
| 8,142,495 B2 | 3/2012 | Hasenkam et al. | |
| 8,142,496 B2 | 3/2012 | Berreklouw | |
| 8,147,542 B2 | 4/2012 | Maisano et al. | |
| 8,152,844 B2 | 4/2012 | Rao et al. | |
| 8,163,013 B2 | 4/2012 | Machold et al. | |
| 8,187,299 B2 | 5/2012 | Goldfarb et al. | |
| 8,187,324 B2 | 5/2012 | Webler et al. | |
| 8,202,315 B2 | 6/2012 | Hlavka et al. | |
| 8,206,439 B2 | 6/2012 | Gomez Duran | |
| 8,216,302 B2 | 7/2012 | Wilson et al. | |
| 8,231,671 B2 | 7/2012 | Kim | |
| 8,241,351 B2 * | 8/2012 | Cabiri | A61F 2/2466 623/2.37 |
| 8,262,725 B2 | 9/2012 | Subramanian | |
| 8,265,758 B2 | 9/2012 | Policker et al. | |
| 8,277,502 B2 | 10/2012 | Miller et al. | |
| 8,287,584 B2 | 10/2012 | Salahieh et al. | |
| 8,287,591 B2 | 10/2012 | Keidar et al. | |
| 8,292,884 B2 | 10/2012 | Levine et al. | |
| 8,303,608 B2 | 11/2012 | Goldfarb et al. | |
| 8,323,334 B2 | 12/2012 | Deem et al. | |
| 8,328,868 B2 | 12/2012 | Paul et al. | |
| 8,333,777 B2 | 12/2012 | Schaller et al. | |
| 8,343,173 B2 | 1/2013 | Starksen et al. | |
| 8,343,174 B2 | 1/2013 | Goldfarb et al. | |
| 8,343,213 B2 | 1/2013 | Salahieh et al. | |
| 8,349,002 B2 | 1/2013 | Milo | |
| 8,353,956 B2 | 1/2013 | Miller et al. | |

(56)                References Cited

U.S. PATENT DOCUMENTS

| 8,357,195 | B2 | 1/2013 | Kuehn |
| 8,382,829 | B1 | 2/2013 | Call et al. |
| 8,388,680 | B2 | 3/2013 | Starksen et al. |
| 8,393,517 | B2 | 3/2013 | Milo |
| 8,419,825 | B2 | 4/2013 | Burgler et al. |
| 8,430,926 | B2 | 4/2013 | Kirson |
| 8,449,573 | B2 | 5/2013 | Chu |
| 8,449,599 | B2 | 5/2013 | Chau et al. |
| 8,454,686 | B2 | 6/2013 | Alkhatib |
| 8,460,370 | B2 | 6/2013 | Zakay |
| 8,460,371 | B2 | 6/2013 | Hlavka et al. |
| 8,475,491 | B2 | 7/2013 | Milo |
| 8,475,525 | B2 | 7/2013 | Maisano et al. |
| 8,480,732 | B2 | 7/2013 | Subramanian |
| 8,518,107 | B2 | 8/2013 | Tsukashima et al. |
| 8,523,940 | B2 | 9/2013 | Richardson et al. |
| 8,545,553 | B2 * | 10/2013 | Zipory ................. A61B 17/072 |
| | | | 623/2.37 |
| 8,551,161 | B2 | 10/2013 | Dolan |
| 8,585,755 | B2 | 11/2013 | Chau et al. |
| 8,591,576 | B2 | 11/2013 | Hasenkam et al. |
| 8,608,797 | B2 | 12/2013 | Gross et al. |
| 8,628,569 | B2 | 1/2014 | Benichou et al. |
| 8,628,571 | B1 | 1/2014 | Hacohen et al. |
| 8,641,727 | B2 | 2/2014 | Starksen et al. |
| 8,652,202 | B2 | 2/2014 | Alon et al. |
| 8,652,203 | B2 | 2/2014 | Quadri et al. |
| 8,679,174 | B2 | 3/2014 | Ottma et al. |
| 8,685,086 | B2 | 4/2014 | Navia et al. |
| 8,728,097 | B1 | 5/2014 | Sugimoto et al. |
| 8,728,155 | B2 | 5/2014 | Montorfano et al. |
| 8,734,467 | B2 | 5/2014 | Miller et al. |
| 8,734,699 | B2 | 5/2014 | Heideman et al. |
| 8,740,920 | B2 | 6/2014 | Goldfarb et al. |
| 8,747,463 | B2 | 6/2014 | Fogarty et al. |
| 8,778,021 | B2 | 7/2014 | Cartledge |
| 8,784,481 | B2 | 7/2014 | Alkhatib et al. |
| 8,790,367 | B2 | 7/2014 | Nguyen et al. |
| 8,790,394 | B2 | 7/2014 | Miller et al. |
| 8,795,298 | B2 | 8/2014 | Hernlund et al. |
| 8,795,355 | B2 | 8/2014 | Alkhatib |
| 8,795,356 | B2 | 8/2014 | Quadri et al. |
| 8,795,357 | B2 | 8/2014 | Yohanan et al. |
| 8,808,366 | B2 | 8/2014 | Braido et al. |
| 8,808,368 | B2 | 8/2014 | Maisano et al. |
| 8,845,717 | B2 | 9/2014 | Khairkhahan et al. |
| 8,845,723 | B2 | 9/2014 | Spence et al. |
| 8,852,261 | B2 | 10/2014 | White |
| 8,852,272 | B2 | 10/2014 | Gross et al. |
| 8,858,623 | B2 * | 10/2014 | Miller ................... A61F 2/2445 |
| | | | 623/2.36 |
| 8,864,822 | B2 | 10/2014 | Spence et al. |
| 8,870,948 | B1 | 10/2014 | Erzberger et al. |
| 8,870,949 | B2 | 10/2014 | Rowe |
| 8,888,843 | B2 | 11/2014 | Khairkhahan et al. |
| 8,889,861 | B2 | 11/2014 | Skead et al. |
| 8,894,702 | B2 | 11/2014 | Quadri et al. |
| 8,911,461 | B2 | 12/2014 | Traynor et al. |
| 8,911,494 | B2 | 12/2014 | Hammer et al. |
| 8,926,696 | B2 | 1/2015 | Cabiri et al. |
| 8,926,697 | B2 | 1/2015 | Gross et al. |
| 8,932,343 | B2 | 1/2015 | Alkhatib et al. |
| 8,932,348 | B2 | 1/2015 | Solem et al. |
| 8,940,044 | B2 | 1/2015 | Hammer et al. |
| 8,945,211 | B2 | 2/2015 | Sugimoto |
| 8,951,285 | B2 | 2/2015 | Sugimoto et al. |
| 8,951,286 | B2 | 2/2015 | Sugimoto et al. |
| 8,961,595 | B2 | 2/2015 | Alkhatib |
| 8,961,602 | B2 | 2/2015 | Kovach et al. |
| 8,979,922 | B2 | 3/2015 | Jayasinghe et al. |
| 8,992,604 | B2 | 3/2015 | Gross et al. |
| 9,005,273 | B2 | 4/2015 | Salahieh et al. |
| 9,011,520 | B2 | 4/2015 | Miller et al. |
| 9,011,530 | B2 | 4/2015 | Reich et al. |
| 9,023,100 | B2 | 5/2015 | Quadri et al. |
| 9,072,603 | B2 | 7/2015 | Tuval et al. |
| 9,107,749 | B2 | 8/2015 | Bobo et al. |
| 9,119,719 | B2 | 9/2015 | Zipory et al. |
| 9,125,632 | B2 | 9/2015 | Loulmet et al. |
| 9,125,742 | B2 | 9/2015 | Yoganathan et al. |
| 9,138,316 | B2 | 9/2015 | Bielefeld |
| 9,173,646 | B2 | 11/2015 | Fabro |
| 9,180,005 | B1 | 11/2015 | Ashinski et al. |
| 9,180,007 | B2 | 11/2015 | Reich et al. |
| 9,192,472 | B2 | 11/2015 | Gross et al. |
| 9,198,756 | B2 | 12/2015 | Aklog et al. |
| 9,226,825 | B2 | 1/2016 | Starksen et al. |
| 9,265,608 | B2 | 2/2016 | Miller et al. |
| 9,326,857 | B2 | 5/2016 | Cartledge et al. |
| 9,414,921 | B2 | 8/2016 | Miller et al. |
| 9,427,316 | B2 | 8/2016 | Schweich, Jr. et al. |
| 9,474,606 | B2 | 10/2016 | Zipory et al. |
| 9,526,613 | B2 | 12/2016 | Gross et al. |
| 9,561,104 | B2 | 2/2017 | Miller et al. |
| 9,579,090 | B1 | 2/2017 | Simms et al. |
| 9,693,865 | B2 | 7/2017 | Gilmore et al. |
| 9,730,793 | B2 | 8/2017 | Reich et al. |
| 9,788,941 | B2 | 10/2017 | Hacohen |
| 9,801,720 | B2 | 10/2017 | Gilmore et al. |
| 9,907,547 | B2 | 3/2018 | Gilmore et al. |
| 9,949,828 | B2 * | 4/2018 | Sheps ................... A61F 2/2427 |
| 10,368,852 | B2 | 8/2019 | Gerhardt et al. |
| 10,765,514 | B2 * | 9/2020 | Iflah ................... A61B 17/0401 |
| 2001/0021874 | A1 | 9/2001 | Carpentier et al. |
| 2002/0022862 | A1 | 2/2002 | Grafton et al. |
| 2002/0082525 | A1 | 6/2002 | Oslund et al. |
| 2002/0087048 | A1 | 7/2002 | Brock et al. |
| 2002/0103532 | A1 | 8/2002 | Angberg et al. |
| 2002/0120292 | A1 | 8/2002 | Morgan |
| 2002/0151916 | A1 | 10/2002 | Muramatsu et al. |
| 2002/0151970 | A1 | 10/2002 | Garrison et al. |
| 2002/0169358 | A1 | 11/2002 | Mortier et al. |
| 2002/0177904 | A1 | 11/2002 | Huxel et al. |
| 2002/0188301 | A1 | 12/2002 | Dallara et al. |
| 2002/0188350 | A1 | 12/2002 | Arru et al. |
| 2002/0198586 | A1 | 12/2002 | Inoue |
| 2003/0050693 | A1 | 3/2003 | Quijano et al. |
| 2003/0078465 | A1 | 4/2003 | Pai et al. |
| 2003/0078653 | A1 | 4/2003 | Vesely et al. |
| 2003/0083538 | A1 | 5/2003 | Adams et al. |
| 2003/0093148 | A1 | 5/2003 | Bolling et al. |
| 2003/0105519 | A1 | 6/2003 | Fasol et al. |
| 2003/0114901 | A1 | 6/2003 | Loeb et al. |
| 2003/0120340 | A1 | 6/2003 | Liska et al. |
| 2003/0144657 | A1 | 7/2003 | Bowe et al. |
| 2003/0167062 | A1 | 9/2003 | Gambale et al. |
| 2003/0171760 | A1 | 9/2003 | Gambale |
| 2003/0199974 | A1 | 10/2003 | Lee et al. |
| 2003/0204193 | A1 | 10/2003 | Gabriel et al. |
| 2003/0204195 | A1 | 10/2003 | Keane et al. |
| 2003/0229350 | A1 | 12/2003 | Kay |
| 2003/0229395 | A1 | 12/2003 | Cox |
| 2004/0002735 | A1 | 1/2004 | Lizardi et al. |
| 2004/0010287 | A1 | 1/2004 | Bonutti |
| 2004/0019359 | A1 | 1/2004 | Worley et al. |
| 2004/0019377 | A1 | 1/2004 | Taylor et al. |
| 2004/0024451 | A1 | 2/2004 | Johnson et al. |
| 2004/0039442 | A1 | 2/2004 | St. Goar et al. |
| 2004/0044350 | A1 | 3/2004 | Martin et al. |
| 2004/0049211 | A1 | 3/2004 | Tremulis et al. |
| 2004/0059413 | A1 | 3/2004 | Argento |
| 2004/0068273 | A1 | 4/2004 | Fariss et al. |
| 2004/0106950 | A1 | 6/2004 | Grafton et al. |
| 2004/0111095 | A1 | 6/2004 | Gordon et al. |
| 2004/0122514 | A1 | 6/2004 | Fogarty et al. |
| 2004/0127982 | A1 | 7/2004 | Machold et al. |
| 2004/0133274 | A1 | 7/2004 | Webler et al. |
| 2004/0133374 | A1 | 7/2004 | Kattan |
| 2004/0138744 | A1 | 7/2004 | Ashinski et al. |
| 2004/0138745 | A1 | 7/2004 | Macoviak et al. |
| 2004/0148019 | A1 | 7/2004 | Vidlund et al. |
| 2004/0148020 | A1 | 7/2004 | Vidlund et al. |
| 2004/0148021 | A1 | 7/2004 | Cartledge et al. |
| 2004/0176788 | A1 | 9/2004 | Opolski |

(56)　　　　References Cited

U.S. PATENT DOCUMENTS

| | | |
|---|---|---|
| 2004/0181287 A1 | 9/2004 | Gellman |
| 2004/0186566 A1 | 9/2004 | Hindrichs et al. |
| 2004/0193191 A1 | 9/2004 | Starksen et al. |
| 2004/0243227 A1 | 12/2004 | Starksen et al. |
| 2004/0260317 A1 | 12/2004 | Bloom et al. |
| 2004/0260344 A1 | 12/2004 | Lyons et al. |
| 2004/0260393 A1 | 12/2004 | Rahdert et al. |
| 2004/0260394 A1 | 12/2004 | Douk et al. |
| 2004/0267358 A1 | 12/2004 | Reitan |
| 2005/0004668 A1 | 1/2005 | Aklog et al. |
| 2005/0010287 A1 | 1/2005 | Macoviak et al. |
| 2005/0010787 A1 | 1/2005 | Tarbouriech |
| 2005/0016560 A1 | 1/2005 | Voughlohn |
| 2005/0049692 A1 | 3/2005 | Numamoto et al. |
| 2005/0055038 A1 | 3/2005 | Kelleher et al. |
| 2005/0055087 A1 | 3/2005 | Starksen |
| 2005/0060030 A1 | 3/2005 | Ashinski et al. |
| 2005/0065601 A1 | 3/2005 | Lee et al. |
| 2005/0070999 A1 | 3/2005 | Spence |
| 2005/0075654 A1 | 4/2005 | Kelleher |
| 2005/0075727 A1 | 4/2005 | Wheatley |
| 2005/0090827 A1 | 4/2005 | Gedebou |
| 2005/0090834 A1 | 4/2005 | Chiang et al. |
| 2005/0096740 A1 | 5/2005 | Langberg et al. |
| 2005/0107871 A1 | 5/2005 | Realyvasquez et al. |
| 2005/0119734 A1 | 6/2005 | Spence et al. |
| 2005/0125002 A1 | 6/2005 | Baran et al. |
| 2005/0125011 A1 | 6/2005 | Spence et al. |
| 2005/0131533 A1 | 6/2005 | Alfieri et al. |
| 2005/0137686 A1 | 6/2005 | Salahieh et al. |
| 2005/0137688 A1 | 6/2005 | Salahieh et al. |
| 2005/0137695 A1 | 6/2005 | Salahieh et al. |
| 2005/0159728 A1 | 7/2005 | Armour et al. |
| 2005/0159810 A1 | 7/2005 | Filsoufi |
| 2005/0171601 A1 | 8/2005 | Cosgrove et al. |
| 2005/0177180 A1 | 8/2005 | Kaganov et al. |
| 2005/0177228 A1 | 8/2005 | Solem et al. |
| 2005/0187568 A1 | 8/2005 | Klenk et al. |
| 2005/0192596 A1 | 9/2005 | Jugenheimer et al. |
| 2005/0203549 A1 | 9/2005 | Realyvasquez |
| 2005/0203606 A1 | 9/2005 | VanCamp |
| 2005/0216039 A1 | 9/2005 | Lederman |
| 2005/0216079 A1 | 9/2005 | MaCoviak |
| 2005/0222665 A1 | 10/2005 | Aranyi |
| 2005/0234481 A1 | 10/2005 | Waller |
| 2005/0240199 A1 | 10/2005 | Martinek et al. |
| 2005/0251177 A1 | 11/2005 | Saadat et al. |
| 2005/0256532 A1 | 11/2005 | Nayak et al. |
| 2005/0267478 A1 | 12/2005 | Corradi et al. |
| 2005/0273138 A1 | 12/2005 | To et al. |
| 2005/0288778 A1 | 12/2005 | Shaoulian et al. |
| 2006/0004442 A1 | 1/2006 | Spenser et al. |
| 2006/0004443 A1 | 1/2006 | Liddicoat et al. |
| 2006/0020326 A9 | 1/2006 | Bolduc et al. |
| 2006/0020327 A1 | 1/2006 | Ashinski et al. |
| 2006/0020333 A1 | 1/2006 | Lashinski et al. |
| 2006/0020336 A1 | 1/2006 | Liddicoat |
| 2006/0025787 A1 | 2/2006 | Morales et al. |
| 2006/0025858 A1 | 2/2006 | Alameddine |
| 2006/0030885 A1 | 2/2006 | Hyde |
| 2006/0041319 A1 | 2/2006 | Taylor et al. |
| 2006/0069429 A1 | 3/2006 | Spence et al. |
| 2006/0074486 A1 | 4/2006 | Liddicoat et al. |
| 2006/0085012 A1 | 4/2006 | Dolan |
| 2006/0095009 A1 | 5/2006 | Lampropoulos et al. |
| 2006/0106423 A1 | 5/2006 | Weisel et al. |
| 2006/0116757 A1 | 6/2006 | Lashinski et al. |
| 2006/0122633 A1 | 6/2006 | To et al. |
| 2006/0129166 A1 | 6/2006 | Lavelle |
| 2006/0142694 A1 | 6/2006 | Bednarek et al. |
| 2006/0149280 A1 | 7/2006 | Harvie et al. |
| 2006/0149368 A1 | 7/2006 | Spence |
| 2006/0161265 A1 | 7/2006 | Evine et al. |
| 2006/0173251 A1 | 8/2006 | Govari et al. |
| 2006/0184240 A1 | 8/2006 | Jimenez et al. |
| 2006/0184242 A1 | 8/2006 | Lichtenstein |
| 2006/0195134 A1 | 8/2006 | Crittenden |
| 2006/0206203 A1 | 9/2006 | Yang et al. |
| 2006/0212048 A1 | 9/2006 | Crainich |
| 2006/0241622 A1 | 10/2006 | Zergiebel |
| 2006/0241656 A1 | 10/2006 | Starksen et al. |
| 2006/0241748 A1 | 10/2006 | Lee et al. |
| 2006/0247763 A1 | 11/2006 | Slater |
| 2006/0259135 A1 | 11/2006 | Navia et al. |
| 2006/0271175 A1 | 11/2006 | Woolfson et al. |
| 2006/0276871 A1 | 12/2006 | Lamson et al. |
| 2006/0282161 A1 | 12/2006 | Huynh et al. |
| 2006/0287661 A1 | 12/2006 | Bolduc et al. |
| 2006/0287716 A1 | 12/2006 | Banbury et al. |
| 2007/0001627 A1 | 1/2007 | Lin et al. |
| 2007/0010800 A1 | 1/2007 | Weitzner et al. |
| 2007/0016287 A1 | 1/2007 | Cartledge et al. |
| 2007/0016288 A1 | 1/2007 | Gurskis et al. |
| 2007/0021781 A1 | 1/2007 | Jervis et al. |
| 2007/0027533 A1 | 2/2007 | Douk |
| 2007/0027536 A1 | 2/2007 | Mihaljevic et al. |
| 2007/0032823 A1 | 2/2007 | Tegg |
| 2007/0038221 A1 | 2/2007 | Fine et al. |
| 2007/0038293 A1 | 2/2007 | St.Goar et al. |
| 2007/0038296 A1 | 2/2007 | Navia et al. |
| 2007/0039425 A1 | 2/2007 | Wang |
| 2007/0049942 A1 | 3/2007 | Hindrichs et al. |
| 2007/0049970 A1 | 3/2007 | Belef et al. |
| 2007/0051377 A1 | 3/2007 | Douk et al. |
| 2007/0055206 A1 | 3/2007 | To et al. |
| 2007/0060922 A1 | 3/2007 | Dreyfuss |
| 2007/0061010 A1 | 3/2007 | Hauser et al. |
| 2007/0066863 A1 | 3/2007 | Rafiee et al. |
| 2007/0078297 A1 | 4/2007 | Rafiee et al. |
| 2007/0080188 A1 | 4/2007 | Spence et al. |
| 2007/0083168 A1 | 4/2007 | Whiting et al. |
| 2007/0083235 A1 | 4/2007 | Jervis et al. |
| 2007/0100427 A1 | 5/2007 | Perouse |
| 2007/0106328 A1 | 5/2007 | Wardle et al. |
| 2007/0112359 A1 | 5/2007 | Kimura et al. |
| 2007/0112422 A1 | 5/2007 | Dehdashtian |
| 2007/0112425 A1 | 5/2007 | Schaller et al. |
| 2007/0118151 A1 | 5/2007 | Davidson |
| 2007/0118154 A1 | 5/2007 | Crabtree |
| 2007/0118213 A1 | 5/2007 | Loulmet |
| 2007/0118215 A1 | 5/2007 | Moaddeb |
| 2007/0142907 A1 | 6/2007 | Moaddeb et al. |
| 2007/0162111 A1 | 7/2007 | Fukamachi et al. |
| 2007/0173931 A1 | 7/2007 | Tremulis et al. |
| 2007/0198082 A1 | 8/2007 | Kapadia et al. |
| 2007/0219558 A1 | 9/2007 | Deutsch |
| 2007/0239208 A1 | 10/2007 | Crawford |
| 2007/0244554 A1 | 10/2007 | Rafiee et al. |
| 2007/0244556 A1 | 10/2007 | Rafiee et al. |
| 2007/0255397 A1 | 11/2007 | Ryan et al. |
| 2007/0255400 A1 | 11/2007 | Parravicini et al. |
| 2007/0270755 A1 | 11/2007 | Von Oepen et al. |
| 2007/0276437 A1 | 11/2007 | Call et al. |
| 2007/0282375 A1 | 12/2007 | Hindrichs et al. |
| 2007/0282429 A1 | 12/2007 | Hauser et al. |
| 2007/0295172 A1 | 12/2007 | Swartz |
| 2007/0299424 A1 | 12/2007 | Cumming et al. |
| 2008/0004697 A1 | 1/2008 | Lichtenstein et al. |
| 2008/0027483 A1 | 1/2008 | Cartledge et al. |
| 2008/0027555 A1 | 1/2008 | Hawkins |
| 2008/0033460 A1 | 2/2008 | Ziniti et al. |
| 2008/0035160 A1 | 2/2008 | Woodson et al. |
| 2008/0039935 A1 | 2/2008 | Buch et al. |
| 2008/0051703 A1 | 2/2008 | Thornton et al. |
| 2008/0058595 A1 | 3/2008 | Snoke et al. |
| 2008/0065011 A1 | 3/2008 | Marchand et al. |
| 2008/0065204 A1 | 3/2008 | Macoviak et al. |
| 2008/0071366 A1 | 3/2008 | Tuval et al. |
| 2008/0086138 A1 | 4/2008 | Stone et al. |
| 2008/0086203 A1 | 4/2008 | Roberts |
| 2008/0091169 A1 | 4/2008 | Heideman et al. |
| 2008/0091257 A1 | 4/2008 | Andreas et al. |
| 2008/0097483 A1 | 4/2008 | Ortiz et al. |
| 2008/0097523 A1 | 4/2008 | Bolduc et al. |

(56)                  References Cited

U.S. PATENT DOCUMENTS

| | | |
|---|---|---|
| 2008/0103572 A1 | 5/2008 | Gerber |
| 2008/0140116 A1 | 6/2008 | Bonutti |
| 2008/0167713 A1 | 7/2008 | Bolling |
| 2008/0167714 A1 | 7/2008 | St. Goar et al. |
| 2008/0177380 A1 | 7/2008 | Starksen et al. |
| 2008/0195126 A1 | 8/2008 | Solem |
| 2008/0195200 A1 | 8/2008 | Vidlund et al. |
| 2008/0208265 A1 | 8/2008 | Frazier et al. |
| 2008/0221672 A1 | 9/2008 | Lamphere et al. |
| 2008/0228030 A1 | 9/2008 | Godin |
| 2008/0228223 A1 | 9/2008 | Alkhatib |
| 2008/0234729 A1 | 9/2008 | Page et al. |
| 2008/0262480 A1 | 10/2008 | Stahler et al. |
| 2008/0262609 A1 | 10/2008 | Gross et al. |
| 2008/0275300 A1 | 11/2008 | Rothe et al. |
| 2008/0275469 A1 | 11/2008 | Fanton et al. |
| 2008/0275551 A1 | 11/2008 | Alfieri |
| 2008/0281353 A1 | 11/2008 | Aranyi et al. |
| 2008/0281411 A1 | 11/2008 | Berreklouw |
| 2008/0287862 A1 | 11/2008 | Weitzner et al. |
| 2008/0288044 A1 | 11/2008 | Osborne |
| 2008/0288062 A1 | 11/2008 | Andrieu et al. |
| 2008/0294251 A1 | 11/2008 | Annest et al. |
| 2008/0300537 A1 | 12/2008 | Bowman |
| 2008/0300629 A1 | 12/2008 | Surti |
| 2008/0312506 A1 | 12/2008 | Spivey et al. |
| 2009/0024110 A1 | 1/2009 | Heideman et al. |
| 2009/0028670 A1 | 1/2009 | Garcia et al. |
| 2009/0043381 A1 | 2/2009 | Macoviak et al. |
| 2009/0054723 A1 | 2/2009 | Khairkhahan et al. |
| 2009/0054969 A1 | 2/2009 | Salahieh et al. |
| 2009/0062866 A1 | 3/2009 | Jackson |
| 2009/0076586 A1 | 3/2009 | Hauser et al. |
| 2009/0076600 A1 | 3/2009 | Quinn |
| 2009/0082797 A1 | 3/2009 | Fung et al. |
| 2009/0088837 A1 | 4/2009 | Gillinov et al. |
| 2009/0093877 A1 | 4/2009 | Keidar et al. |
| 2009/0099650 A1 | 4/2009 | Bolduc et al. |
| 2009/0105816 A1 | 4/2009 | Olsen et al. |
| 2009/0125102 A1 | 5/2009 | Cartledge et al. |
| 2009/0166913 A1 | 7/2009 | Guo et al. |
| 2009/0171439 A1 | 7/2009 | Nissl |
| 2009/0177266 A1 | 7/2009 | Powell et al. |
| 2009/0177274 A1 | 7/2009 | Scorsin et al. |
| 2009/0248148 A1 | 10/2009 | Shaolian et al. |
| 2009/0254103 A1 | 10/2009 | Deutsch |
| 2009/0264994 A1 | 10/2009 | Saadat |
| 2009/0287231 A1 | 11/2009 | Brooks et al. |
| 2009/0287304 A1 | 11/2009 | Dahlgren et al. |
| 2009/0299409 A1 | 12/2009 | Coe et al. |
| 2009/0326648 A1 | 12/2009 | Machold et al. |
| 2010/0001038 A1 | 1/2010 | Levin et al. |
| 2010/0010538 A1 | 1/2010 | Juravic et al. |
| 2010/0023118 A1 | 1/2010 | Medlock et al. |
| 2010/0030014 A1 | 2/2010 | Ferrazzi |
| 2010/0030328 A1 | 2/2010 | Seguin et al. |
| 2010/0042147 A1 | 2/2010 | Janovsky et al. |
| 2010/0049213 A1 | 2/2010 | Serina et al. |
| 2010/0063542 A1 | 3/2010 | van der Burg et al. |
| 2010/0063550 A1 | 3/2010 | Felix et al. |
| 2010/0076499 A1 | 3/2010 | McNamara et al. |
| 2010/0094248 A1 | 4/2010 | Nguyen et al. |
| 2010/0094314 A1 | 4/2010 | Hernlund et al. |
| 2010/0106141 A1 | 4/2010 | Osypka et al. |
| 2010/0114180 A1 | 5/2010 | Rock et al. |
| 2010/0121349 A1 | 5/2010 | Meier et al. |
| 2010/0121435 A1 | 5/2010 | Subramanian et al. |
| 2010/0121437 A1 | 5/2010 | Subramanian et al. |
| 2010/0130989 A1 | 5/2010 | Bourque et al. |
| 2010/0130992 A1 | 5/2010 | Machold et al. |
| 2010/0152845 A1 | 6/2010 | Bloom et al. |
| 2010/0161042 A1* | 6/2010 | Maisano ............... A61F 2/2457 623/2.11 |
| 2010/0161043 A1 | 6/2010 | Maisano et al. |
| 2010/0168845 A1 | 7/2010 | Wright |
| 2010/0174358 A1 | 7/2010 | Rabkin et al. |
| 2010/0179574 A1 | 7/2010 | Longoria et al. |
| 2010/0217184 A1 | 8/2010 | Koblish et al. |
| 2010/0217382 A1 | 8/2010 | Chau et al. |
| 2010/0234935 A1 | 9/2010 | Bashiri et al. |
| 2010/0249497 A1 | 9/2010 | Peine et al. |
| 2010/0249908 A1 | 9/2010 | Chau et al. |
| 2010/0249915 A1 | 9/2010 | Zhang |
| 2010/0249920 A1 | 9/2010 | Bolling et al. |
| 2010/0262232 A1 | 10/2010 | Annest |
| 2010/0262233 A1 | 10/2010 | He |
| 2010/0280604 A1* | 11/2010 | Zipory ................. A61F 2/2436 623/2.37 |
| 2010/0286628 A1 | 11/2010 | Gross |
| 2010/0298929 A1 | 11/2010 | Thornton et al. |
| 2010/0305475 A1 | 12/2010 | Hinchliffe et al. |
| 2010/0324598 A1 | 12/2010 | Anderson |
| 2011/0004210 A1 | 1/2011 | Johnson et al. |
| 2011/0004298 A1 | 1/2011 | Lee et al. |
| 2011/0009956 A1 | 1/2011 | Cartledge et al. |
| 2011/0011917 A1 | 1/2011 | Loulmet |
| 2011/0026208 A1 | 2/2011 | Utsuro et al. |
| 2011/0029066 A1 | 2/2011 | Gilad et al. |
| 2011/0035000 A1 | 2/2011 | Nieminen et al. |
| 2011/0066231 A1 | 3/2011 | Cartledge et al. |
| 2011/0067770 A1 | 3/2011 | Pederson et al. |
| 2011/0071626 A1 | 3/2011 | Wright et al. |
| 2011/0082538 A1 | 4/2011 | Dahlgren et al. |
| 2011/0087146 A1 | 4/2011 | Ryan et al. |
| 2011/0093002 A1 | 4/2011 | Rucker et al. |
| 2011/0118832 A1 | 5/2011 | Punjabi |
| 2011/0137410 A1 | 6/2011 | Hacohen |
| 2011/0144576 A1 | 6/2011 | Rothe et al. |
| 2011/0144703 A1 | 6/2011 | Krause et al. |
| 2011/0202130 A1 | 8/2011 | Cartledge et al. |
| 2011/0208283 A1 | 8/2011 | Rust |
| 2011/0230941 A1 | 9/2011 | Markus |
| 2011/0230961 A1 | 9/2011 | Langer et al. |
| 2011/0238088 A1 | 9/2011 | Bolduc et al. |
| 2011/0257433 A1 | 10/2011 | Walker |
| 2011/0257633 A1 | 10/2011 | Cartledge et al. |
| 2011/0264208 A1 | 10/2011 | Duffy et al. |
| 2011/0276062 A1 | 11/2011 | Bolduc |
| 2011/0288435 A1 | 11/2011 | Christy et al. |
| 2011/0301498 A1 | 12/2011 | Maenhout et al. |
| 2011/0301698 A1* | 12/2011 | Miller .................. A61F 2/2442 623/2.1 |
| 2012/0053628 A1 | 3/2012 | Sojka et al. |
| 2012/0053642 A1 | 3/2012 | Lozier et al. |
| 2012/0065464 A1 | 3/2012 | Ellis et al. |
| 2012/0078355 A1 | 3/2012 | Zipory et al. |
| 2012/0078359 A1 | 3/2012 | Li et al. |
| 2012/0089022 A1 | 4/2012 | House et al. |
| 2012/0089125 A1 | 4/2012 | Scheibe et al. |
| 2012/0095552 A1 | 4/2012 | Spence et al. |
| 2012/0109155 A1 | 5/2012 | Robinson et al. |
| 2012/0143226 A1 | 6/2012 | Belson et al. |
| 2012/0150290 A1 | 6/2012 | Gabbay |
| 2012/0158021 A1 | 6/2012 | Morrill |
| 2012/0158023 A1 | 6/2012 | Mitelberg et al. |
| 2012/0179086 A1 | 7/2012 | Shank et al. |
| 2012/0191182 A1 | 7/2012 | Hauser et al. |
| 2012/0226349 A1 | 9/2012 | Tuval et al. |
| 2012/0239142 A1 | 9/2012 | Liu et al. |
| 2012/0245604 A1 | 9/2012 | Tegzes |
| 2012/0271198 A1 | 10/2012 | Whittaker et al. |
| 2012/0296349 A1 | 11/2012 | Smith et al. |
| 2012/0296417 A1 | 11/2012 | Hill et al. |
| 2012/0310330 A1 | 12/2012 | Buchbinder et al. |
| 2012/0323313 A1 | 12/2012 | Seguin |
| 2013/0030522 A1 | 1/2013 | Rowe et al. |
| 2013/0046373 A1 | 2/2013 | Cartledge et al. |
| 2013/0053884 A1 | 2/2013 | Roorda |
| 2013/0079873 A1 | 3/2013 | Migliazza et al. |
| 2013/0085529 A1 | 4/2013 | Housman |
| 2013/0090724 A1 | 4/2013 | Subramanian et al. |
| 2013/0096673 A1 | 4/2013 | Hill et al. |
| 2013/0116776 A1 | 5/2013 | Gross et al. |
| 2013/0123910 A1 | 5/2013 | Cartledge et al. |

(56) References Cited

U.S. PATENT DOCUMENTS

| | | |
|---|---|---|
| 2013/0131791 A1 | 5/2013 | Hlavka et al. |
| 2013/0166017 A1 | 6/2013 | Cartledge et al. |
| 2013/0190863 A1 | 7/2013 | Call et al. |
| 2013/0204361 A1 | 8/2013 | Adams et al. |
| 2013/0218206 A1 | 8/2013 | Gadlage |
| 2013/0226289 A1 | 8/2013 | Shaolian et al. |
| 2013/0226290 A1 | 8/2013 | Yellin et al. |
| 2013/0231701 A1 | 9/2013 | Voss et al. |
| 2013/0268069 A1 | 10/2013 | Zakai et al. |
| 2013/0282059 A1 | 10/2013 | Ketai et al. |
| 2013/0289718 A1 | 10/2013 | Tsukashima et al. |
| 2013/0297013 A1 | 11/2013 | Klima et al. |
| 2013/0304093 A1 | 11/2013 | Serina et al. |
| 2013/0331930 A1 | 12/2013 | Rowe et al. |
| 2014/0067054 A1 | 3/2014 | Chau et al. |
| 2014/0081394 A1 | 3/2014 | Keranen et al. |
| 2014/0088368 A1 | 3/2014 | Park |
| 2014/0088646 A1 | 3/2014 | Wales et al. |
| 2014/0094826 A1 | 4/2014 | Sutherland et al. |
| 2014/0094903 A1 | 4/2014 | Miller et al. |
| 2014/0094906 A1 | 4/2014 | Spence et al. |
| 2014/0114390 A1 | 4/2014 | Tobis et al. |
| 2014/0135799 A1 | 5/2014 | Henderson |
| 2014/0142619 A1 | 5/2014 | Serina et al. |
| 2014/0142695 A1 | 5/2014 | Gross et al. |
| 2014/0148849 A1 | 5/2014 | Serina et al. |
| 2014/0155783 A1 | 6/2014 | Starksen et al. |
| 2014/0163615 A1 | 6/2014 | Gadlage et al. |
| 2014/0163670 A1 | 6/2014 | Alon et al. |
| 2014/0163690 A1 | 6/2014 | White |
| 2014/0188108 A1 | 7/2014 | Goodine et al. |
| 2014/0188140 A1 | 7/2014 | Meier et al. |
| 2014/0188215 A1 | 7/2014 | Hlavka et al. |
| 2014/0194976 A1 | 7/2014 | Starksen et al. |
| 2014/0207231 A1 | 7/2014 | Hacohen et al. |
| 2014/0243859 A1 | 8/2014 | Robinson |
| 2014/0243894 A1 | 8/2014 | Groothuis et al. |
| 2014/0243963 A1 | 8/2014 | Sheps et al. |
| 2014/0251042 A1 | 9/2014 | Asselin et al. |
| 2014/0275757 A1 | 9/2014 | Goodwin et al. |
| 2014/0276648 A1 | 9/2014 | Hammer et al. |
| 2014/0296962 A1 | 10/2014 | Cartledge et al. |
| 2014/0303649 A1 | 10/2014 | Nguyen et al. |
| 2014/0303720 A1 | 10/2014 | Sugimoto et al. |
| 2014/0309661 A1 | 10/2014 | Sheps et al. |
| 2014/0309730 A1 | 10/2014 | Alon et al. |
| 2014/0343668 A1 | 11/2014 | Zipory et al. |
| 2014/0350660 A1 | 11/2014 | Cocks et al. |
| 2014/0379006 A1 | 12/2014 | Sutherland et al. |
| 2015/0018940 A1 | 1/2015 | Quill et al. |
| 2015/0051697 A1 | 2/2015 | Spence et al. |
| 2015/0081014 A1 | 3/2015 | Gross et al. |
| 2015/0094800 A1 | 4/2015 | Chawla |
| 2015/0100116 A1 | 4/2015 | Mohl et al. |
| 2015/0112432 A1 | 4/2015 | Reich et al. |
| 2015/0127097 A1 | 5/2015 | Neumann et al. |
| 2015/0133997 A1 | 5/2015 | Deitch et al. |
| 2015/0182336 A1 | 7/2015 | Zipory et al. |
| 2015/0230919 A1 | 8/2015 | Chau et al. |
| 2015/0272586 A1 | 10/2015 | Herman et al. |
| 2015/0272734 A1 | 10/2015 | Sheps et al. |
| 2015/0282931 A1 | 10/2015 | Brunnett et al. |
| 2015/0351910 A1 | 12/2015 | Gilmore et al. |
| 2016/0008132 A1 | 1/2016 | Cabiri et al. |
| 2016/0029920 A1 | 2/2016 | Kronstrom et al. |
| 2016/0030034 A1 | 2/2016 | Graul et al. |
| 2016/0058557 A1 | 3/2016 | Reich et al. |
| 2016/0113767 A1 | 4/2016 | Miller et al. |
| 2016/0120642 A1 | 5/2016 | Shaolian et al. |
| 2016/0120645 A1 | 5/2016 | Alon |
| 2016/0158008 A1 | 6/2016 | Miller et al. |
| 2016/0242762 A1 | 8/2016 | Gilmore et al. |
| 2016/0256149 A1 | 9/2016 | Sampson et al. |
| 2016/0256274 A1 | 9/2016 | Hayoz |
| 2016/0262755 A1 | 9/2016 | Zipory et al. |
| 2016/0302917 A1 | 10/2016 | Schewel |
| 2016/0317302 A1 | 11/2016 | Madjarov et al. |
| 2016/0346084 A1 | 12/2016 | Taylor et al. |
| 2016/0361058 A1 | 12/2016 | Bolduc et al. |
| 2016/0361168 A1 | 12/2016 | Gross et al. |
| 2016/0361169 A1 | 12/2016 | Gross et al. |
| 2017/0000609 A1 | 1/2017 | Gross et al. |
| 2017/0042670 A1 | 2/2017 | Shaolian et al. |
| 2017/0100119 A1 | 4/2017 | Baird et al. |
| 2017/0224489 A1 | 8/2017 | Starksen et al. |
| 2017/0245993 A1 | 8/2017 | Gross et al. |
| 2018/0008409 A1 | 1/2018 | Kutzik et al. |
| 2018/0049875 A1 * | 2/2018 | Iflah .................... A61F 2/2412 |
| 2018/0140420 A1 | 5/2018 | Hayoz et al. |
| 2018/0168803 A1 | 6/2018 | Pesce et al. |
| 2018/0228608 A1 | 8/2018 | Sheps et al. |
| 2018/0256334 A1 | 9/2018 | Sheps et al. |
| 2018/0280019 A1 | 10/2018 | Azar et al. |
| 2018/0289480 A1 | 10/2018 | D'Ambra et al. |
| 2018/0318080 A1 | 11/2018 | Quill et al. |
| 2018/0318083 A1 | 11/2018 | Bolling et al. |
| 2019/0029498 A1 | 1/2019 | Mankowski et al. |
| 2019/0038411 A1 | 2/2019 | Alon |
| 2019/0091445 A1 | 3/2019 | House |
| 2019/0111239 A1 | 4/2019 | Bolduc et al. |
| 2019/0117400 A1 | 4/2019 | Medema et al. |
| 2019/0125325 A1 | 5/2019 | Sheps et al. |
| 2019/0151093 A1 | 5/2019 | Keidar et al. |
| 2019/0175344 A1 | 6/2019 | Khairkhahan |
| 2019/0175345 A1 | 6/2019 | Schaffner et al. |
| 2019/0175346 A1 | 6/2019 | Schaffner et al. |
| 2019/0183648 A1 | 6/2019 | Trapp et al. |
| 2019/0240023 A1 | 8/2019 | Spence et al. |
| 2019/0290260 A1 | 9/2019 | Caffes et al. |
| 2019/0290431 A1 | 9/2019 | Genovese et al. |
| 2019/0321049 A1 | 10/2019 | Herman et al. |
| 2019/0343633 A1 | 11/2019 | Garvin et al. |
| 2020/0015810 A1 | 1/2020 | Piccirillo |
| 2020/0015971 A1 | 1/2020 | Brauon et al. |
| 2020/0113685 A1 * | 4/2020 | Miller .................... A61F 2/2487 |
| 2020/0178956 A1 | 6/2020 | Mitelberg et al. |
| 2020/0289267 A1 * | 9/2020 | Peleg .................... A61F 2/2466 |
| 2020/0337840 A1 | 10/2020 | Reich |
| 2020/0390551 A1 | 12/2020 | McCarthy |
| 2021/0015475 A1 | 1/2021 | Lau |
| 2021/0052387 A1 | 2/2021 | Greenan et al. |
| 2021/0059820 A1 | 3/2021 | Clark et al. |
| 2021/0085461 A1 | 3/2021 | Neumark et al. |
| 2021/0093453 A1 | 4/2021 | Peleg et al. |
| 2021/0145584 A1 | 5/2021 | Kasher et al. |
| 2022/0096232 A1 | 3/2022 | Skaro et al. |
| 2022/0110656 A1 | 4/2022 | Azar et al. |
| 2022/0142779 A1 * | 5/2022 | Sharon .................... A61F 2/2466 |
| 2022/0233316 A1 | 7/2022 | Sheps et al. |
| 2022/0313438 A1 | 10/2022 | Chappel-Ram |
| 2022/0323221 A1 | 10/2022 | Sharon et al. |
| 2023/0218291 A1 | 7/2023 | Zarbatany et al. |
| 2023/0320856 A1 | 10/2023 | Zarbatany et al. |
| 2024/0000571 A1 * | 1/2024 | Peleg .................... A61F 2/9517 |
| 2024/0008985 A1 | 1/2024 | Yuan et al. |
| 2024/0099736 A1 | 3/2024 | Elsheikh et al. |

FOREIGN PATENT DOCUMENTS

| | | | | |
|---|---|---|---|---|
| CN | 119499010 A * | 2/2025 | ........... | A61F 2/2448 |
| EP | 1034753 A1 | 9/2000 | | |
| EP | 3531975 A1 | 9/2019 | | |
| EP | 4088688 A1 * | 11/2022 | ........... | A61F 2/2466 |
| EP | 4193934 A1 * | 6/2023 | ......... | A61B 17/0401 |
| WO | 9205093 A1 | 4/1992 | | |
| WO | 9846149 A1 | 10/1998 | | |
| WO | WO-2002085250 A2 | 10/2002 | | |
| WO | 02085250 A3 | 2/2003 | | |
| WO | 03047467 A1 | 6/2003 | | |
| WO | WO-2007098512 A1 | 9/2007 | | |
| WO | 2010000454 A1 | 1/2010 | | |
| WO | WO-2012176195 A2 | 12/2012 | | |
| WO | 2012176195 A3 | 3/2013 | | |
| WO | 2014064964 A1 | 5/2014 | | |

(56) References Cited

FOREIGN PATENT DOCUMENTS

| | | | | |
|---|---|---|---|---|
| WO | 2019145941 A1 | 8/2019 | | |
| WO | WO-2019145947 A1 * | 8/2019 | .......... | A61F 2/9517 |
| WO | 2019182645 A1 | 9/2019 | | |
| WO | 2019224814 A1 | 11/2019 | | |
| WO | 2020240282 A2 | 12/2020 | | |
| WO | 2021014440 A2 | 1/2021 | | |
| WO | 2021038559 A1 | 3/2021 | | |
| WO | 2021038560 A1 | 3/2021 | | |
| WO | WO-2021146757 A2 * | 7/2021 | .......... | A61F 2/2457 |
| WO | WO-2021191713 A1 * | 9/2021 | .......... | A61B 17/068 |
| WO | WO-2022064401 A2 | 3/2022 | | |
| WO | WO-2022090907 A1 | 5/2022 | | |
| WO | WO-2022101817 A2 | 5/2022 | | |
| WO | WO-2022153131 A1 | 7/2022 | | |
| WO | WO-2022157592 A1 | 7/2022 | | |
| WO | WO-2022172108 A1 | 8/2022 | | |
| WO | WO-2022172149 A1 | 8/2022 | | |
| WO | WO-2022200972 A1 | 9/2022 | | |
| WO | WO-2022224071 A1 | 10/2022 | | |
| WO | WO-2022229815 A1 | 11/2022 | | |
| WO | WO-2022250983 A1 | 12/2022 | | |

OTHER PUBLICATIONS

Ahmadi, A., G. Spillner, and Th Johannesson. "Hemodynamic changes following experimental production and correction of acute mitral regurgitation with an adjustable ring prosthesis." The Thoracic and cardiovascular surgeon36.06 (1988): 313-319.

Ahmadi, Ali et al. "Percutaneously adjustable pulmonary artery band." The Annals of thoracic surgery 60 (1995): S520-S522.

Alfieri et al."Novel Suture Device for Beating-Heart Mitral Leaflet Approximation", Ann Thorac Surg. 2002, 74:1488-1493.

Alfieri et al., "An effective technique to correct anterior mitral leaflet prolapse," J Card 14(6):468-470 (1999).

Alfieri et al., "The double orifice technique in mitral valve repair: a simple solution for complex problems," Journal of Thoracic Cardiovascular Surgery 122:674-681 (2001).

Alfieri, "The edge-to-edge repair of the mitral valve," [Abstract] 6th Annual NewEra Cardiac Care: Innovation & Technology, Heart Surgery Forum pp. 103. (2000).

Amplatzer Cardiac Plug brochure (English pages), AGA Medical Corporation (Plymouth, MN) (copyright 2008-2010, downloaded Jan. 11, 2011).

AMPLATZER® Cribriform Occluder. A patient guide to Percutaneous, Transcatheter, Atrial Septal Defect Closuer, AGA Medical Corporation, Apr. 2008.

AMPLATZER® Septal Occluder. A patient guide to the Non-Surgical Closuer of the Atrial Septal Defect Using the AMPLATZER Septal Occluder System, AGA Medical Corporation, Apr. 2008.

Assad, Renato S. "Adjustable Pulmonary Artery Banding." (2014).

Brennan, Jennifer, 510(k) Summary of safety and effectiveness, Jan. 2008.

Daebritz, S. et al. "Experience with an adjustable pulmonary artery banding device in two cases: initial success—midterm failure." The Thoracic and cardiovascular surgeon 47.01 (1999): 51-52.

Dang NC et al. "Simplified Placement of Multiple Artificial Mitral Valve Chords," The Heart Surgery Forum #2005-1005, 8 (3) (2005).

Dictionary.com definition of "lock", Jul. 29, 2013.

Dieter RS, "Percutaneous valve repair: Update on mitral regurgitation and endovascular approaches to the mitral valve," Applications in Imaging, Cardiac Interventions, Supported by an educational grant from Amersham Health pp. 11-14 (2003).

Elliott, Daniel S., Gerald W. Timm, and David M. Barrett. "An implantable mechanical urinary sphincter: a new honhydraulic design concept." Urology52.6 (1998): 1151-1154.

Langer et al. Ring plus String: Papillary muscle repositioning as an adjunctive repair technique for ischemic mitral regurgitation, The Journal of Thoracic Cardiovascular surgery vol. 133 No. 1, Jan. 2007.

Langer et al. Ring+String, Successful Repair technique for ischemic mitral regurgitation with severe leaflet Tethering, The Department of Thoracic Cardiovascular surgery, Hamburg, Germany, Nov. 2008.

Maisano, "The double-orifice technique as a standardized approach to treat mitral," European Journal of Cardio-thoracic Surgery 17 (2000) 201-205.

O'Reilly S et al., "Heart valve surgery pushes the envelope," Medtech Insight 8(3): 73, 99-108 (2006).

Odell JA et al., "Early Results 04yf a Simplified Method of Mitral Valve Annuloplasty," Circulation 92:150-154 (1995).

Park, Sang C. et al. "A percutaneously adjustable device for banding of the pulmonary trunk." International journal of cardiology 9.4 (1985): 477-484.

Swain CP et al., "An endoscopically deliverable tissue-transfixing device for securing biosensors in the gastrointestinal tract," Gastrointestinal Endoscopy 40(6): 730-734 (1994).

Swenson, O. An experimental implantable urinary sphincter. Invest Urol. Sep. 1976;14(2):100-3.

Swenson, O. and Malinin, T.I., 1978. An improved mechanical device for control of urinary incontinence. Investigative urology, 15(5), pp. 389-391.

Swenson, Orvar. "Internal device for control of urinary incontinence." Journal of pediatric surgery 7.5 (1972): 542-545.

Tajik, Abdul, "Two dimensional real-time ultrasonic imaging of the heart and great vessels", Mayo Clin Proc. vol. 53:271-303, 1978.

* cited by examiner

SELF-LOCKING WINCH

CROSS-REFERENCES TO RELATED APPLICATIONS

The present application is a Continuation of International Patent Application PCT/IB2021/051902 to Tennenbaum, filed Mar. 8, 2021, and entitled "Self-locking winch," which published as WO 2021/191713, and which claims priority from Provisional U.S. Patent Application 62/993,669 to Tennenbaum, filed Mar. 23, 2020, and entitled "Self-locking winch," which is incorporated herein by reference for all purposes.

BACKGROUND

Dilation of the annulus of a heart valve, such as that caused by ischemic heart disease, prevents the valve leaflets from fully coapting when the valve is closed. Regurgitation of blood from the ventricle into the atrium results in increased total stroke volume and decreased cardiac output, and ultimate weakening of the ventricle secondary to a volume overload and a pressure overload of the atrium.

SUMMARY OF THE INVENTION

This summary is meant to provide some examples and is not intended to be limiting of the scope of the invention in any way. For example, any feature included in an example of this summary is not required by the claims, unless the claims explicitly recite the features. Also, the features described can be combined in a variety of ways. Various features and steps as described elsewhere in this disclosure can be included in the examples summarized here.

Some applications of the present invention are directed to systems, apparatuses, and methods for adjusting a medical implant using an adjustment mechanism.

The adjustment mechanism can comprise a winch. For some applications, adjustment is achieved by using the winch to apply tension to a tether, the tether extending away from the winch toward an end portion. The winch can comprise a spool coupled to the tether. The winch can be fixedly coupled to a mount having a driver interface, such that such that driving of the driver interface by a driver rotates the mount about a rotation axis, drawing the end portion of the tether toward the spool by winding the tether around the spool axis of the spool.

The spool can be coupled to the mount in a position and an orientation with respect to the rotation axis that facilitates the spool drawing the end portion of the tether toward the winch by winding of the tether around the spool in response to rotation of the mount in a forward rotational direction about the rotation axis. Further, the spool can be coupled to the mount in a position and an orientation with respect to the rotation axis that inhibits unwinding of the tether from the spool in response to pulling of the end portion away from the spool, by inhibiting the pulling from rotating the mount in a reverse rotational direction about the rotation axis.

That is, although the position and orientation of the spool facilitate the spool drawing the end portion of the tether toward the winch by winding of the tether around the spool in response to forward rotation of the mount about the rotation axis, this position and orientation typically inhibit pulling of the end portion away from the spool from causing reverse rotation of the mount and unwinding of the tether from the spool.

Generally, the spool (e.g., a spool axis defined by the spool) is not coaxial with the rotation axis.

For some applications, the spool can be disposed laterally from (e.g., parallel with) the rotation axis. For some such applications, the spool is entirely disposed laterally form the rotation axis, e.g., such that upon rotation of the mount about the rotation axis, the spool revolves around the rotation axis.

Optionally, the spool can be orthogonal to the rotation axis, e.g., such that the rotation axis passes through the spool, e.g., such that upon rotation of the mount about the rotation axis, the spool rotates about the rotation axis in a manner similar to that of a propeller on its axle.

For some applications, the adjustment mechanism includes at least one inclined guide coupled to the mount and disposed laterally from the rotation axis. The inclined guide can be positioned such that, upon rotation of the mount in the forward rotational direction, the guide guides the tether around the spool. For some such applications, driving of the driver interface by the driver moves the guide, with the mount, about the rotation axis.

For some applications, the adjustment mechanism includes a housing that houses the winch and is configured to facilitate rotation of the mount about the rotation axis with respect to the housing, the spool moving with the mount. The housing can define an aperture configured to facilitate passage of the tether from outside the winch to the spool as the spool draws the end portion of the tether toward the winch.

For some applications, the adjustment mechanism comprises at least one flange, configured to provide mechanical separation between the tether and the driver interface.

For some applications, the winch includes an eyelet that defines an aperture therethrough. The aperture can be configured to facilitate passage of the tether from outside the winch to the spool as the spool draws the end portion of the tether toward the winch. For some applications, the eyelet is mechanically engaged with the guide such that, upon rotation of the mount in the forward rotational direction, the inclined guide guides the tether around the spool by moving the eyelet longitudinally, parallel with the rotation axis, e.g., along a track, such as a track defined by the housing.

For some applications, at least one anchor is used to anchor the end portion of the tether to tissue of a subject. Some such applications include an annuloplasty structure that is configured such that the drawing of the end portion of the tether from the anchor toward the winch reduces a length of the structure. For example, the annuloplasty structure can comprise a longitudinal flexible sleeve defining an elongate lumen, coupled to the winch, and having a contracting portion along which the tether extends. Drawing of the end portion of the tether toward the winch can longitudinally contract the contracting portion.

There is therefore provided, in accordance with some applications, a system and/or an apparatus for use with a transcatheterally-advanceable driver, the system/apparatus including an implant. The implant can include a tether, having an end portion and a winch.

For some applications, the winch includes a driver interface, engageable and drivable by the driver and a mount, coupled to the driver interface such that driving of the driver interface by the driver rotates the mount about a rotation axis.

For some applications, the winch includes a spool coupled to the tether, the tether extending away from the winch toward the end portion and is fixedly coupled to the mount in a position and an orientation with respect to the rotation axis. For some applications, the position and the orientation facilitate the spool drawing the end portion of the tether toward the winch by winding of the tether around the spool in response to rotation of the mount in a forward rotational direction about the rotation axis; and inhibiting unwinding of the tether from the spool in response to pulling of the end portion away from the spool, by inhibiting the pulling from rotating the mount in a reverse rotational direction about the rotation axis.

In an application, the spool is fixedly coupled to the mount such that the spool is entirely disposed laterally from the rotation axis.

In an application, the spool is shaped to define an eye therethrough, the tether being threaded through the eye.

In an application, the spool is fixedly coupled to the mount in a position and an orientation that provides at least one stable rotational orientation of the mount at which the pulling is inhibited from rotating the mount in the reverse rotational direction about the rotation axis. In an application, the spool is fixedly coupled to the mount in a position and an orientation that provides exactly one stable rotational orientation of the mount at which the pulling is inhibited from rotating the mount in the reverse rotational direction about the rotation axis.

In an application, the spool is fixedly coupled to the mount in a position and an orientation that provides at least two stable rotational orientations of the mount at which pulling is inhibited from rotating the mount in the reverse rotational direction about the rotation axis. In an application, the spool is fixedly coupled to the mount in a position and an orientation that provides exactly two stable rotational orientations of the mount at which pulling is inhibited from rotating the mount in the reverse rotational direction about the rotation axis.

In an application, the winch includes at least one flange, the flange configured to provide mechanical separation between the tether and the driver interface. In an application, the mount is shaped to define the at least one flange.

In an application, the position and the orientation inhibit unwinding of the tether from the spool in response to the pulling by limiting, to less than 180 degrees of reverse rotation, the rotation of the mount in the reverse rotational direction in response to the pulling. In an application, the position and the orientation inhibit unwinding of the tether from the spool in response to the pulling by limiting, to less than 90 degrees of reverse rotation, the rotation of the mount in the reverse rotational direction in response to the pulling. In an application, the position and the orientation inhibit unwinding of the tether from the spool in response to the pulling by limiting, to less than 45 degrees of reverse rotation, the rotation of the mount in the reverse rotational direction in response to the pulling.

In an application, the system/apparatus includes a housing that houses the winch, the housing configured to facilitate movement of the mount and the spool about the rotation axis, with respect to the housing.

In an application, the housing defines an aperture, the aperture configured to facilitate passage of the tether from outside the winch to the spool as the spool draws the end portion of the tether toward the winch.

In an application, the driver interface is accessible to the driver while the winch is housed within the housing.

In an application, the housing is shaped to define an aperture, and the tether extends from the spool, out of the winch via the aperture, and away from the winch toward the end portion.

In an application, the aperture defined by the housing is a circular aperture.

In an application, the aperture defined by the housing is an elongate aperture. In an application, the elongate aperture has a long axis that is disposed on an aperture plane that is transverse to the rotation axis.

In an application, the implant further includes at least one anchor configured to anchor the end portion of the tether to tissue of a subject.

In an application, the at least one anchor includes a plurality of anchors, the tether is slidable with respect to at least one of the anchors, and the winch is configured such that drawing the end portion of the tether toward the winch in response to rotation of the mount in the forward rotational direction causes at least one of the anchors to slide distally with respect to the tether.

In an application, the implant includes an annuloplasty structure, and is configured such that the drawing of the end portion of the tether toward the winch reduces a length of the structure.

In an application, the annuloplasty structure includes a longitudinal flexible sleeve: defining an elongate lumen, coupled to the winch, anchorable by the anchor to the tissue, such that the tether is anchored to the tissue by the sleeve being anchored to the tissue, and having a contracting portion along which the tether extends. In an application, the system/apparatus is configured such that the drawing of the end portion of the tether toward the winch longitudinally contracts the contracting portion.

In an application, the sleeve is coupled to the winch by stitches.

In an application, the winch is coupled to an outer, lateral surface of the sleeve.

In an application, a first portion of the tether extends along the contracting portion; and a second portion of the tether: exits the sleeve at an exit point and is coupled to the winch.

In an application, the system/apparatus includes a delivery tool for delivering the implant to a body of a subject, the delivery tool including a catheter, a distal portion of the catheter being advanceable into the body of the subject.

In an application, the catheter is a steerable transluminal catheter.

In an application, the system/apparatus includes the driver and a guide member, and in a delivery state of the system/apparatus: the implant is disposed at the distal portion of the catheter, and the guide member is coupled to the winch, and extends from the winch proximally through the catheter, to a proximal portion of the catheter, and the driver is slidable over and along the guide member.

In an application, the spool is fixedly coupled to the mount laterally from the rotation axis, such that, in a cross-section of the winch orthogonal to the rotation axis, a radius of the winch: extends radially outward from the rotation axis toward the spool, reaches the spool at a first surface point of the spool, passes through the spool, and passes out of the spool at a second surface point of the spool.

In an application, in the cross-section, the spool has a cross-sectional shape that is a trapezoid. In an application, in the cross-section, the spool has a cross-sectional shape that is a D-shape. In an application, the spool is shaped to define a spool axis, the spool axis being parallel with the rotation axis.

In an application, in the cross-section, the first surface point of the spool is a closest point of the spool to the rotation axis. In an application, in the cross-section, the first surface point of the spool is at least 0.2 mm from the rotation axis. In an application, in the cross-section, the first surface point of the spool is 0.2-4 mm from the rotation axis. In an application, in the cross-section, the first surface point of the spool is 0.3-2 mm from the rotation axis.

In an application, the spool is fixedly coupled to the mount orthogonally to the rotation axis.

In an application, the winch includes at least one inclined guide coupled to the mount, disposed laterally from the rotation axis, and positioned such that, upon rotation of the mount in the forward rotational direction, the at least one inclined guide guides the tether around the spool.

In an application, the at least one inclined guide is fixedly coupled to the mount such that, upon driving of the driver interface by the driver, the at least one inclined guide moves with the mount about the rotation axis.

In an application, the at least one inclined guide defines a guide surface that extends helically around and along the rotation axis.

In an application, the at least one inclined guide includes a first inclined guide and a second inclined guide, the first inclined guide is positioned such that, upon rotation of the mount in the forward rotational direction, the first inclined guide guides the tether to a second side of the spool, and the second inclined guide is positioned such that, upon rotation of the mount in the forward rotational direction, the second inclined guide guides the tether to a first side of the spool that is opposite the second side of the spool.

In an application, the winch defines a first shoulder at which the first inclined guide is coupled to a first end of the spool, and a second shoulder at which the second inclined guide is coupled to a second end of the spool, the first inclined guide is positioned such that, upon rotation of the mount in the forward rotational direction, the first inclined guide guides the tether over the first shoulder to the second side of the spool, and the second inclined guide is positioned such that, upon rotation of the mount in the forward rotational direction, the second inclined guide guides the tether over the second shoulder to the first side of the spool.

In an application, the winch further includes an eyelet that defines an aperture therethrough, the aperture configured to facilitate passage of the tether from outside the winch to the spool as the spool draws the end portion of the tether toward the winch, the eyelet mechanically engaged with the guide such that, upon rotation of the mount in the forward rotational direction, the at least one inclined guide guides the tether around the spool by moving the eyelet longitudinally, parallel with the rotation axis.

In an application, the system/apparatus includes a housing that houses the winch, the housing configured to facilitate movement of the mount and the spool about the rotation axis, with respect to the housing.

In an application, the housing defines a longitudinal track along a track axis, parallel with the rotation axis, the track configured to facilitate, upon rotation of the mount in the forward rotational direction, longitudinal movement of the eyelet along the track axis.

In an application, the driver interface is accessible to the driver while the winch is housed within the housing.

There is further provided, in accordance with some applications, a system and/or an apparatus for use with a trans-catheterally-advanceable driver the system/apparatus including an implant, the implant including: a tether, having an end portion; and a winch.

For some applications, the winch includes a driver interface, engageable and drivable by the driver, and a mount, coupled to the driver interface such that driving of the driver interface by the driver rotates the mount about a rotation axis.

For some applications, the winch includes a spool: defining a spool axis, coupled to the tether, the tether extending away from the winch toward the end portion. The spool can be fixedly coupled to the mount such that: rotation of the mount about the rotation axis draws the end portion of the tether toward the spool by winding the tether around the spool axis of the spool, and the spool axis is non-coaxial with the rotation axis.

In an application, the spool is fixedly coupled to the mount such that the spool is entirely disposed laterally from the rotation axis.

In an application, the spool axis is parallel with the rotation axis.

In an application, the spool is shaped to define an eye therethrough, the tether being threaded through the eye.

In an application, the winch includes at least one flange, the flange configured to provide mechanical separation between the tether and the driver interface.

In an application, the mount is shaped to define the at least one flange.

In an application, the system/apparatus includes a housing that houses the winch, the housing configured to facilitate movement of the mount and the spool about the rotation axis, with respect to the housing.

In an application, the driver interface is accessible to the driver while the winch is housed within the housing.

In an application, the housing is shaped to define an aperture, the tether extends from the spool, out of the winch via the aperture, and away from the winch toward the end portion, and the aperture configured to facilitate passage of the tether into the winch as the spool draws the end portion of the tether toward the winch.

In an application, the housing defines the aperture as circular in shape. In an application, the housing defines the aperture as elongate in shape.

In an application, the housing defines the aperture to have a long axis that is disposed on an aperture plane that is transverse to the rotation axis.

In an application, the implant further includes at least one anchor configured to anchor the end portion of the tether to tissue of a subject.

In an application, the at least one anchor includes a plurality of anchors, the tether is slidable with respect to at least one of the anchors, and the winch is configured such that drawing the end portion of the tether toward the winch in response to rotation of the mount in the forward rotational direction causes at least one of the anchors to slide distally with respect to the tether.

In an application, the implant includes an annuloplasty structure, and is configured such that the drawing of the end portion of the tether toward the winch reduces a length of the structure.

In an application, the annuloplasty structure includes a longitudinal flexible sleeve: defining an elongate lumen, coupled to the winch, and having a contracting portion along which the tether extends, and the system/apparatus is configured such that the drawing of the end portion of the tether toward the winch longitudinally contracts the contracting portion.

In an application, the sleeve is coupled to the winch by stitches.

In an application, the winch is coupled to an outer, lateral surface of the sleeve.

In an application, a first portion of the tether extends along the contracting portion; and a second portion of the tether: exits the sleeve at an exit point and is coupled to the winch.

In an application, the system/apparatus includes a delivery tool for delivering the implant to a body of a subject, the delivery tool including a catheter, a distal portion of the catheter being advanceable into the body of the subject.

In an application, the catheter is a steerable transluminal catheter.

In an application, the system/apparatus includes the driver and a guide member, and in a delivery state of the system/apparatus: the implant is disposed at the distal portion of the catheter, and the guide member is coupled to the winch, and extends from the winch proximally through the catheter, to a proximal portion of the catheter, and the driver is slidable over and along the guide member.

In an application, the spool is fixedly coupled to the mount laterally from the rotation axis, such that, in a cross-section of the winch orthogonal to the rotation axis, a radius of the winch: extends radially outward from the rotation axis toward the spool, reaches the spool at a first surface point of the spool, passes through the spool, and passes out of the spool at a second surface point of the spool.

In an application, in the cross-section, the spool has a cross-sectional shape that is a trapezoid. In an application, in the cross-section, the spool has a cross-sectional shape that is a D-shape.

In an application, in the cross-section, the first surface point of the spool is a closest point of the spool to the rotation axis. In an application, in the cross-section, the first surface point of the spool is at least 0.2 mm from the rotation axis. In an application, in the cross-section, the first surface point of the spool is 0.2-4 mm from the rotation axis. In an application, in the cross-section, the first surface point of the spool is 0.3-2 mm from the rotation axis.

In an application, the spool is fixedly coupled to the mount orthogonally to the rotation axis.

In an application, the winch includes at least one inclined guide coupled to the mount, disposed laterally from the rotation axis, and positioned such that, upon rotation of the mount in the forward rotational direction, the at least one inclined guide guides the tether around the spool.

In an application, the at least one inclined guide is fixedly coupled to the mount such that, upon driving of the driver interface by the driver, the at least one inclined guide moves with the mount about the rotation axis.

In an application, the at least one inclined guide defines a guide surface that extends helically around and along the rotation axis.

In an application, the at least one inclined guide includes a first inclined guide and a second inclined guide, the first inclined guide is positioned such that, upon rotation of the mount in the forward rotational direction, the first inclined guide guides the tether to a second side of the spool, and the second inclined guide is positioned such that, upon rotation of the mount in the forward rotational direction, the second inclined guide guides the tether to a first side of the spool that is opposite the second side of the spool.

In an application, the winch defines a first shoulder at which the first inclined guide is coupled to a first end of the spool, and a second shoulder at which the second inclined guide is coupled to a second end of the spool, the first inclined guide is positioned such that, upon rotation of the mount in the forward rotational direction, the first inclined guide guides the tether over the first shoulder to the second side of the spool, and the second inclined guide is positioned such that, upon rotation of the mount in the forward rotational direction, the second inclined guide guides the tether over the second shoulder to the first side of the spool.

In an application, the system/apparatus includes an eyelet that defines an aperture therethrough, the aperture configured to facilitate passage of the tether from outside the winch to the spool as the spool draws the end portion of the tether toward the winch, the eyelet mechanically engaged with the guide such that, upon rotation of the mount in the forward rotational direction, the at least one inclined guide guides the tether around the spool by moving the eyelet longitudinally, parallel with the rotation axis.

In an application, the system/apparatus includes a housing that houses the winch, the housing configured to facilitate movement of the mount and the spool about the rotation axis, with respect to the housing.

In an application, the housing defines a longitudinal track along a track axis, parallel with the rotation axis, the track configured to facilitate, upon rotation of the mount in the forward rotational direction, longitudinal movement of the eyelet along the track axis.

In an application, the driver interface is accessible to the driver while the winch is housed within the housing.

There is further provided, in accordance with some applications, a method, including: transcatheterally delivering an implant to tissue of a subject, the implant including a tether, having an end portion and a winch.

For some applications, the winch includes a driver interface and a mount, coupled to the driver interface such that driving of the driver interface rotates the mount about a rotation axis.

For some applications, the winch includes a spool: defining a spool axis that is non-coaxial with the rotation axis, coupled to the tether, the tether extending away from the winch toward the end portion, and fixedly coupled to the mount. For some applications, drawing the end portion of the tether toward the spool by winding the tether around the spool axis that is non-coaxial with the rotation axis by rotating the mount about the rotation axis.

In an application, the spool axis is parallel with the rotation axis, and winding the tether around the spool axis includes winding the tether around the spool axis that is parallel with the rotation axis.

In an application, the spool axis that is orthogonal to the rotation axis and winding the tether around the spool axis includes winding the tether around the spool axis that is orthogonal to the rotation axis.

In an application, the method includes engaging the driver interface with a driver and rotating the mount about the rotation axis includes rotating the mount about the rotation axis by driving the driver interface with the driver.

In an application, the method includes, subsequently to transcatheterally delivering the implant to the tissue of the subject, and prior to engaging the driver interface with the driver, transcatheterally advancing the driver to the driver interface.

This method can be performed on a living animal or on a simulation, such as on a cadaver, cadaver heart, simulator (e.g. with the body parts, tissue, etc. being simulated), etc.

There is further provided, in accordance with some applications, a method, including transcatheterally delivering an implant to tissue of a subject, the implant including: a tether, having an end portion; and a winch that includes a driver interface and a mount. The winch can also include a spool defining a spool axis.

For some applications, the method includes engaging the driver interface with a driver. For some applications, the method includes using the driver, tensioning the tether by winding the tether toward the winch by rotating the mount in a forward rotational direction about a rotation axis.

For some applications, without locking a discrete locking mechanism, the method includes disengaging the driver from the driver interface such that the mount is inhibited from rotating in a reverse rotational direction about the rotation axis in response to pulling from the tensioned tether.

In an application, the spool axis is parallel with the rotation axis, and winding the tether toward the winch includes winding the tether around the spool axis that is parallel with the rotation axis.

In an application, the spool axis that is orthogonal to the rotation axis, and winding the tether toward the winch includes winding the tether around the spool axis that is orthogonal to the rotation axis.

In an application, the method includes, subsequently to transcatheterally delivering the implant to the tissue of the subject, and prior to engaging the driver interface with the driver, transcatheterally advancing the driver to the driver interface.

This method can be performed on a living animal or on a simulation, such as on a cadaver, cadaver heart, simulator (e.g. with the body parts, tissue, etc. being simulated), etc.

The present invention will be more fully understood from the following detailed description of applications thereof, taken together with the drawings, in which:

DETAILED DESCRIPTION OF EMBODIMENTS

Figure 1C:
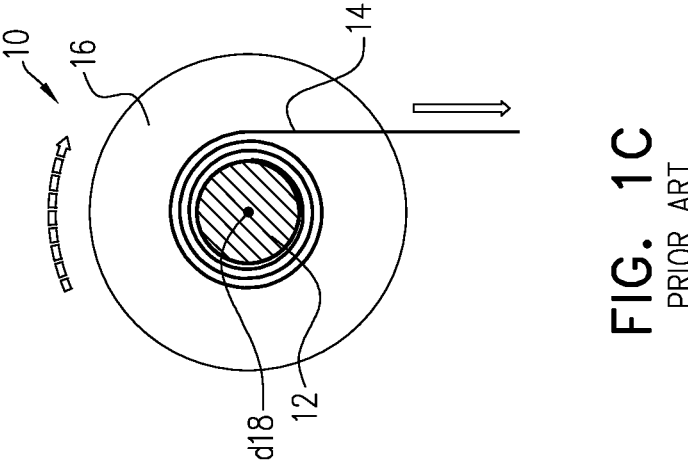
FIGS. 1A-C and 2A-C are schematic illustrations showing prior art winches.
Figure 1B:
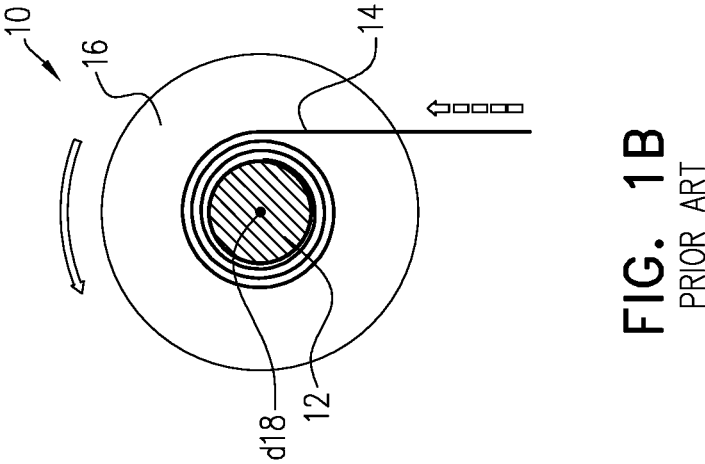
Figure 1A:
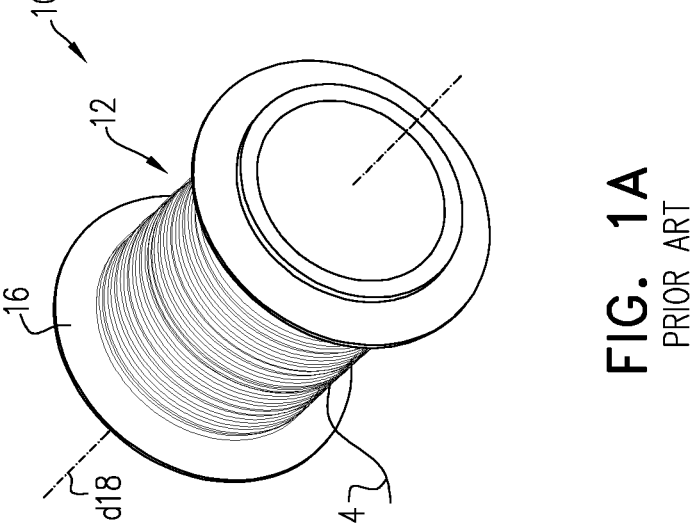

Reference is made to FIGS. 1A-C, 2A-C, which are schematic illustrations showing prior art winches 10 and 10b. For some applications, and as shown in FIG. 1A, winch 10 comprises a spool 12 to which a tether 14, comprising an elongate member (e.g. a wire, a ribbon, a rope, a cable, a thread, a filament, etc.) is affixed.

Winch 10 can further comprise a mount 16 to which spool 12 is fixedly attached, such that both the mount and the spool rotate together about a common rotation axis d18. In this way, and as shown in FIG. 1B, rotation of the mount and spool (indicated by solid arrow) about axis d18 winds tether 14 into the winch (indicated by a broken arrow), the tether winding around spool 12.

Throughout this patent application, the direction of rotation of a winch (or the mount thereof) about its rotation axis that results in winding of the tether about the spool is defined as "forward rotation."

It is to be noted that mount 16 and spool 12 are coaxial.

As shown in FIG. 1C, in the absence of any inhibiting force or element, a pulling force applied to a distal end of tether 14 pulls the tether out of the winch, due to the pulling force rotating spool 12 in a reverse rotational direction (indicated by dotted arrow), in a direction opposite of that which accompanied winding of the tether about the spool, such that the tether unwinds from the spool. Throughout this disclosure, the direction of rotation of a winch that results in unwinding of the tether from about the spool is defined as "reverse rotation."

Figures 2A, 2B, 2C:
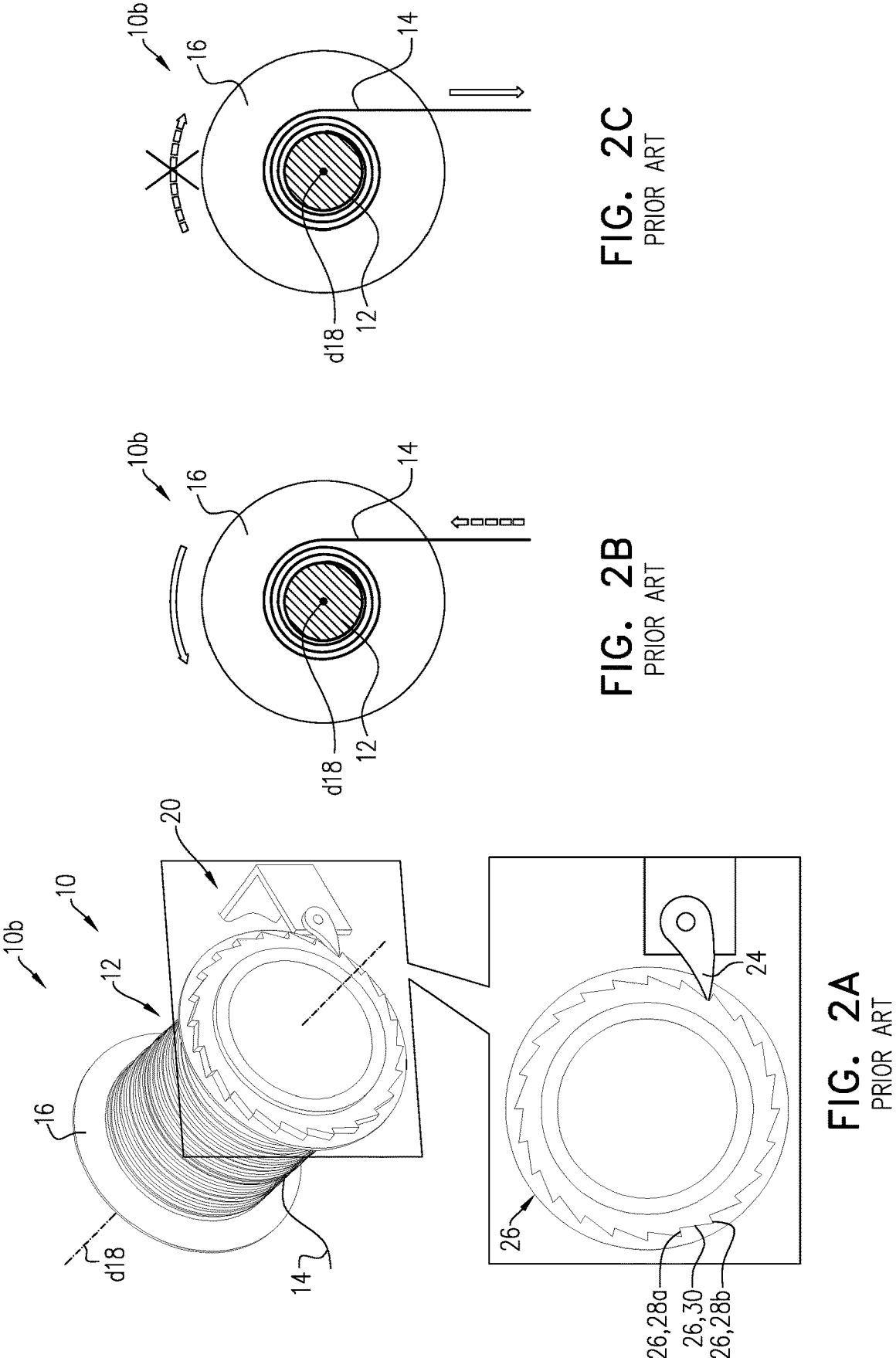

For some applications, it may be desirable to prevent unwinding of tether 14 in response to a pulling force applied to the distal end of the tether. For example, after applying tension to tether 14 during winding in the forward direction, it may be desirable to maintain this tension in the tether. FIG. 2A shows a prior art solution for this, in which a locking mechanism 20 is incorporated into winch 10, resulting in a winch 10b. For example, and as shown, locking mechanism 20 can comprise a ratchet 22 and a pawl 24 affixed to mount 16. Often, and as shown, ratchet 22 is affixed to mount 16 in a manner which enables rotational movement of both the mount and spool 12, about axis d18. Further, ratchet 22 can be shaped to define teeth 26, and pawl 24 is shaped to complimentarily fit teeth 26 of the ratchet. Pawl 24 can be biased (e.g., by a spring) to engage ratchet 22, such that pawl abuts successive teeth 26 of the ratchet, as the ratchet rotates. Due to the shape of teeth 26 and pawl 24, rotation of spool 12 in the forward direction (counter-clockwise, in FIG. 2A) results in the sliding of the pawl from a brake zone 28a of a first tooth 26, along a ramp zone 30 of a second tooth, to a brake zone 28b of the second tooth.

Often, and as shown, locking mechanism 20 enables rotation of spool (solid arrow in FIG. 2B) about axis d18, accompanied by winding of tether 14 (dotted arrow in FIG. 2B). However, when a pulling force is applied to a distal end of tether 14 (solid arrow in FIG. 2C), spool 12 is largely prevented from rotating in the reverse direction (dotted arrow in FIG. 2C). That is, the pulling force pulls the spool in the reverse direction such that pawl 24 generally crosses a portion of a ramp zone 30, until the pawl abuts a brake zone 28, ceasing backward rotation of winch 10. In this way, tether 14 can unwind for less than the rotational length of a tooth 26, until the static abutment of pawl 24 against brake zone 28 prevents the tether from unwinding further. That is, locking mechanism 20 inhibits unwinding of tether 14 from spool 12 in response to pulling of the end portion of the tether away from the spool, by providing winch 10 with unidirectionality.

Other prior art solutions for inhibiting such unwinding of a tether from a spool include actuatable locking mechanisms, which are unlocked during winding in of the tether, and are subsequently locked to inhibit further rotation of the spool (e.g., in either direction). An example of such a locking mechanism is described in US Patent Application Publication 2010/0280604 to Zipory et al. (e.g., with reference to FIGS. 6A-8).

Reference is made to FIGS. 3A-E, 4A-C, which are schematic illustrations showing an adjustment mechanism 36 comprising a winch 40, in accordance with some applications.

Figures 3A, 3B:
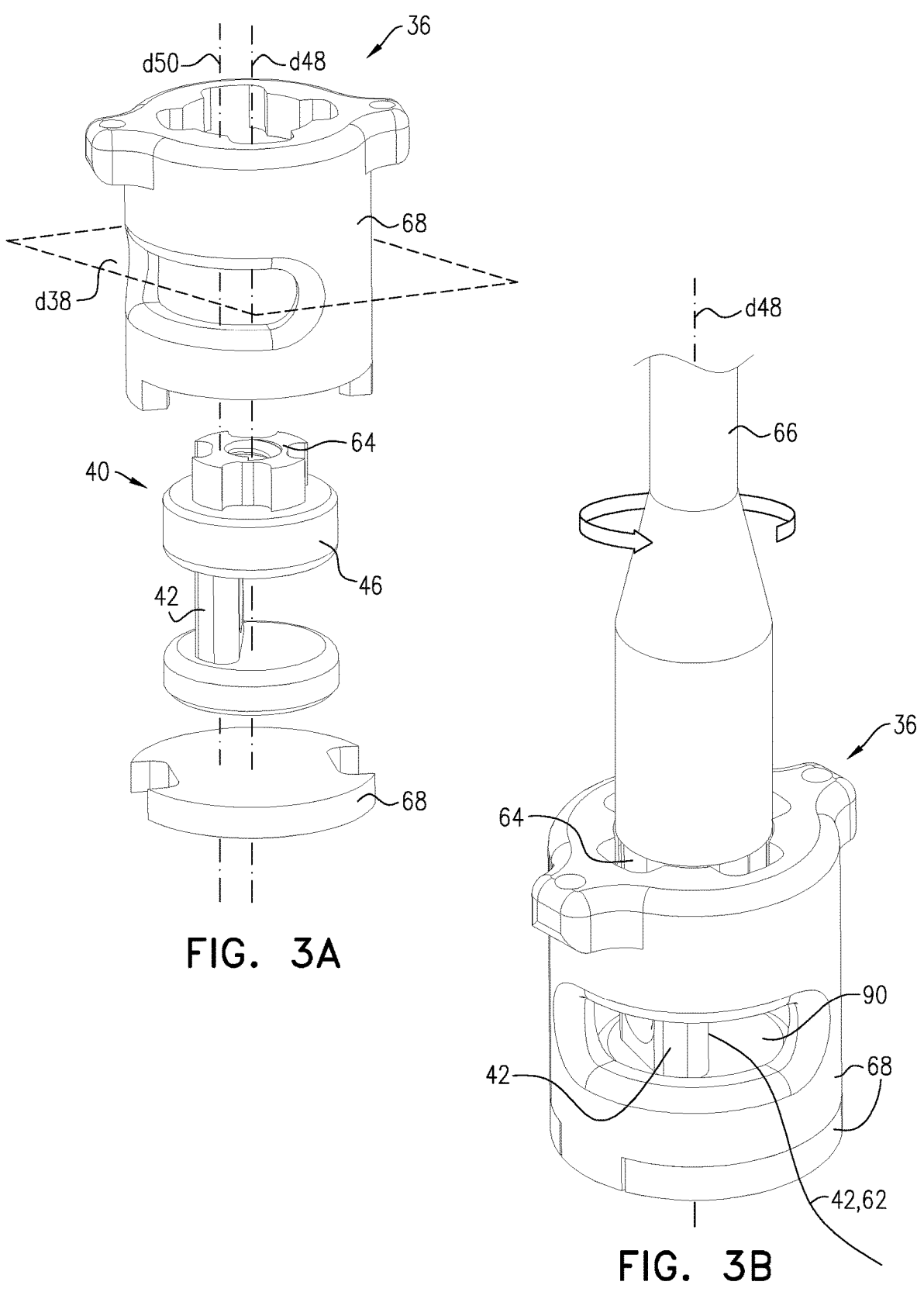
FIGS. 3A-E and 4A-C are schematic illustrations showing an adjustment mechanism comprising a winch, in accordance with some applications.

As shown in FIG. 3A, winch 40 comprises a mount 46, a spool 42, and a driver interface 64. As shown in FIG. 3B, engaging and driving of the driver interface by a transcatheterally-advanceable driver 66 rotates mount 46 about a rotation axis d48 of the winch.

Spool 42 is generally shaped to define a longitudinal spool axis d50.

Whereas the mount and the spool of winch 10 are coaxial, in winch 40 spool 42 is not coaxial with rotation axis d48.

Instead, and as described in more detail hereinbelow, spool 42 is disposed laterally from axis d48.

Similarly to winch 10, for winch 40, in response to rotation in a forward rotational direction, tether 44 is drawn into the winch and is wound around spool 42. However, in contrast to winch 10, the position and orientation at which spool 42 is coupled to mount 46 inhibits subsequent unwinding of tether 44 from the spool in response to pulling of the end portion away from the spool. That is, the position and orientation at which spool 42 is coupled to mount 46 at least in part obviates a need for adjustment mechanism 36 to comprise a discrete locking mechanism (e.g., a discrete actuatable locking mechanism). It is to be noted that, despite this, winch 40 is bidirectionally rotational by driver 66.

For some applications, and as shown in FIGS. 3A-B, adjustment mechanism 36 further comprises a housing 68 in which the winch is housed, such that mount 46 rotates about axis d48 with respect to the housing. Often, and as shown, housing 68 is shaped to define an aperture 90, and tether 44 extends from spool 42, out of winch 40 via the aperture, and away from the winch toward end portion 62. For some applications, and as shown, aperture 90 is shaped to define an elongate shape, a long axis thereof being disposed on an aperture plane d38 that is transverse to spool axis d50.

As shown in FIG. 3B, for applications in which winch 40 is housed within housing 68, driver interface 64 can be accessible to driver 66 from outside of the housing.

Tether 44 (e.g., a proximal end thereof) is fixedly attached (e.g. tied, crimped, soldered, brazed or welded) to spool 42. For some applications, and as shown, spool 42 is shaped to define an eye 80 that is configured to facilitate this affixation.

Figures 3C, 3D, 3E:
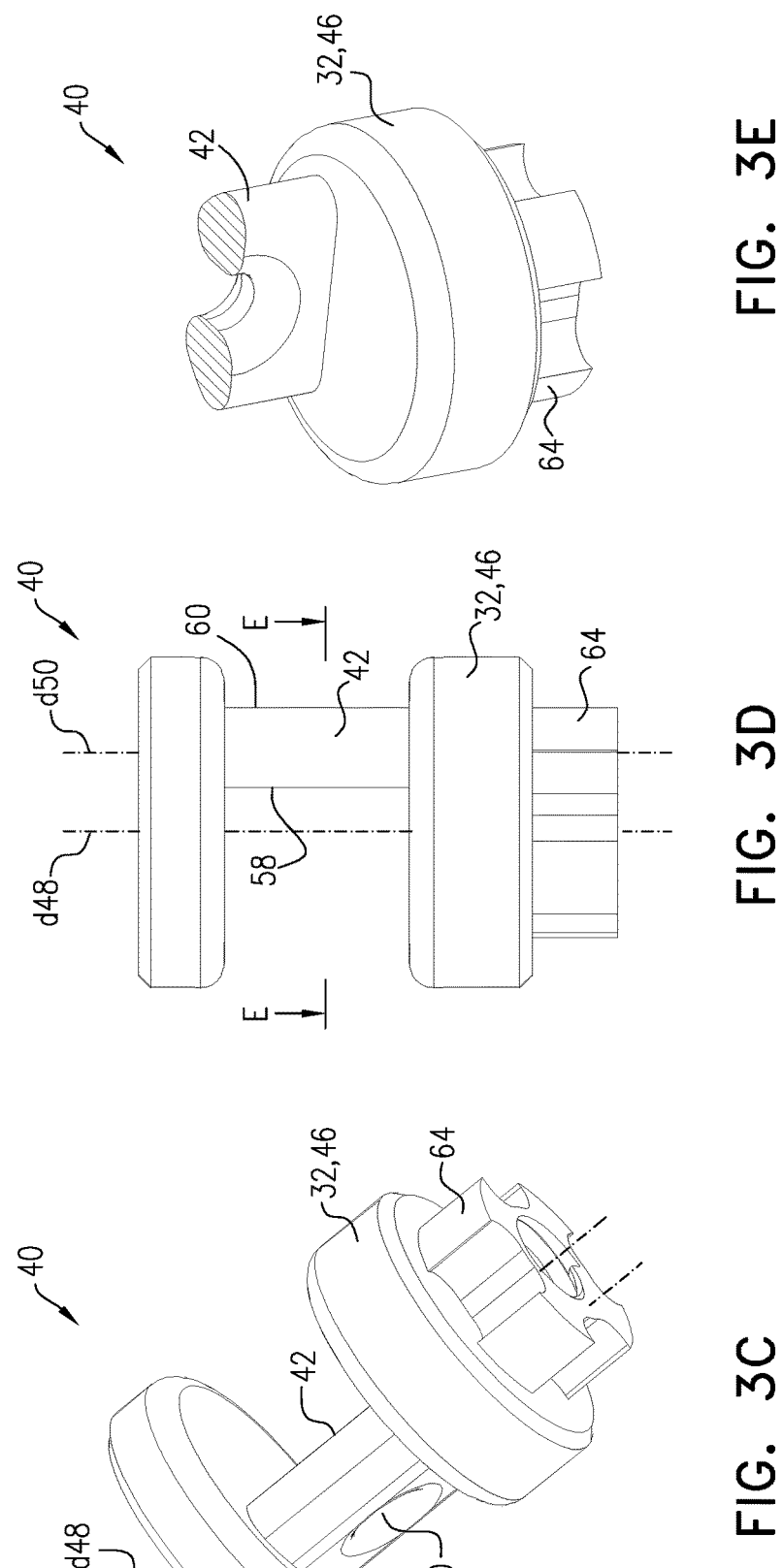

For some applications, and as shown in FIG. 3C, winch 40 further comprises at least one flange 32, e.g., two flanges 32, one at each end of spool 42 (e.g., abutting the spool). For some applications, flanges 32 are defined by and/or are integral with mount 46. Often, flange 32 is shaped to provide mechanical separation between spool 42 and driver interface 64. It is therefore hypothesized that flange 32 inhibits tether 44 from slipping off of spool 42 and/or becoming trapped between elements of the adjustment mechanism.

As described hereinabove, in response to rotation of mount 46 in its forward rotational direction (solid arrow in FIG. 4A), tether 44 is drawn into the winch (broken arrow in FIG. 4A), and is wound around spool 42—e.g., as shown by the transition between FIGS. 4A and 4B. As also described hereinabove, the position and orientation at which spool 42 is coupled to mount 46 inhibits subsequent unwinding of tether 44 from the spool (represented by the absence of a rotational arrow in FIG. 4C) in response to pulling of tether 44 away from the spool (solid arrow in FIG. 4C). That is, pulling tether 44 does not rotate mount 46 in a reverse rotational direction about the rotation axis. In fact, in certain rotational positions of mount 46, pulling tether 44 rotates the mount a little further in the forward rotational orientation (e.g., as shown by the transition between FIGS. 4B and 4C), e.g., until the winch reaches a stable rotational orientation.

Figures 4A, 4B, 4C:
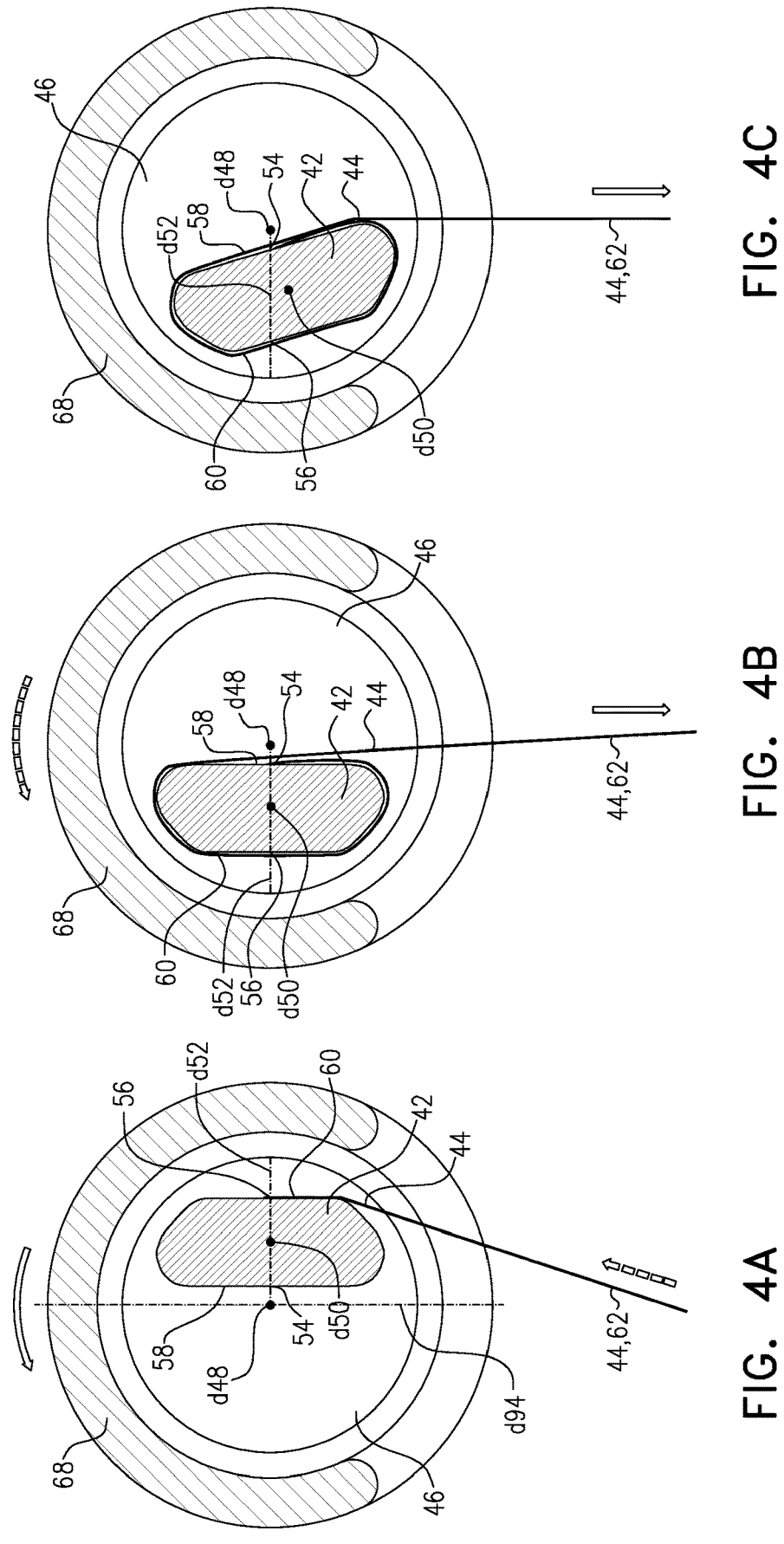

FIG. 4B and FIG. 4C illustrate transition of winch 40 from a dynamic rotational position (FIG. 4B) to a stable rotational orientation (FIG. 4C). In both the dynamic rotational position and the stable rotational orientation, the pulling force (solid arrow) is applied to tether 44 in the same direction. As denoted by the broken arrow in FIG. 4B, the pulling force rotates spool 42 in the forward rotational direction, until it reaches the stable rotational orientation shown in FIG. 4C. When winch 40 assumes its stable rotational orientation, further pulling of the tether does not: (i) unwind tether 44 from spool 42 in response to pulling of tether 44 away from the spool, nor (ii) rotate mount 46 about the rotation axis.

As described hereinabove, the stable rotational orientation that provides resistance to unwinding in response to pulling of the tether results from the position and orientation at which spool 42 is coupled to mount 46. As shown, spool 42 is disposed laterally from axis d48, e.g., with spool axis d50 being non-coaxial with rotation axis d48. For example, and as shown, spool axis d50 can be parallel to rotation axis d48.

For some applications, spool 42 is entirely disposed laterally from the rotation axis. That is, a radius d52 of the winch extends radially outward from axis d48 toward spool 42, reaches spool 42 at a first surface point 54, passes through the spool, and passes out of the spool at a second surface point 56. For some applications, spool 42 defines two opposing sides: (i) a first side 58 that includes surface point 54 and faces axis d48, and (ii) a second side 60 that includes surface point 56 and faces away from axis d48. Both sides 58 and 60 are disposed on the same lateral side of rotation axis d48, such that axis d48 does not pass through spool 42.

Due to the position of spool 42 with respect to mount 46, when the mount rotates about rotation axis d48, the spool revolves around the rotation axis d48 but typically does not meet the rotation axis. That is, spool axis d50 remains radially outward from rotation axis d48 during rotation of winch 40.

Often, the position and orientation at which spool 42 is coupled to mount 46 is such that portions of tether 44 that are wound around the spool are disposed laterally from rotation axis d48 (e.g., on one side of line d94).

Often, spool 42 is fixedly coupled to mount 46 such that the spool is entirely disposed laterally from rotation axis d48. That is, often, a central line d94 (e.g., a diameter or a secant thereof) can be drawn transverse to rotation axis d48, without the line passing through the spool. For example, in the cross-section (as in FIGS. 4A-C), first surface point 54 is a closest point of spool 42 to rotation axis d48, and is generally sufficiently distant from axis d48 to provide space for windings of the wire to be disposed between the spool and axis d48. First surface point 54 can be at least 0.2 mm (e.g. 0.2-4 mm, such as 0.3-2 mm) from rotation axis d48 and/or from line d94. Similarly, first side 58 can be entirely disposed at least 0.2 mm (e.g. 0.2-4 mm, such as 0.3-2 mm) from line d94. It is hypothesized that both the spool and the tether being disposed laterally from the rotation axis facilitates assumption of a stable rotational orientation by the winch, despite the pulling force upon the end portion of the tether.

For some applications, spool 42 has a cross-sectional shape that is circular. For some applications, and as shown, the cross-sectional shape of spool 42 is non-circular, e.g., such that first side 58 defines a long side of the spool. For example, the cross-sectional shape in the cross section (as in FIGS. 4A-C), spool 42 can have a cross-sectional shape that is a trapezoid (e.g. wherein the longer of the parallel sides of the trapezoid is first side 58). Optionally, in the cross section (as in FIGS. 4A-C), spool 42 can have a cross-sectional shape that is a D-shape (e.g. wherein the curved side of the D-shape is the second side). The cross-sectional shape shown is configured to provide a relatively large circumference in order to wind in a relatively long length of tether 44 per revolution, while remaining entirely laterally from axis d48. These exemplary cross-sectional shapes of spool 42 are not meant to be exhaustive, and other shapes are contemplated.

Reference is made to FIGS. 5A-B, 6A-C, 7A-L, and to FIGS. 8A-E, 9A-C, which are schematic illustrations showing adjustment mechanisms 136 and 236, respectively comprising winches 140 and 240, in accordance with some applications. Features common to adjustment mechanisms 136 and 236 will be presented first, followed by description of aspects unique to each winch.

Whereas the mount and the spool of winch 10 are coaxial, in winches 140, 240, spool 142, 242 is not coaxial with rotation axis d148, d248. Instead, and as described in more detail hereinbelow, spool 142, 242 is disposed orthogonally to axis d148, d248. It is to be noted that, despite this, winch 140, 240 are also bidirectionally rotational by driver 66.

Tether 44 (e.g., a proximal end thereof) is fixedly attached (e.g. tied, crimped, soldered, brazed or welded) to spool 142, 242. For some applications, and as shown, spool 142, 242 is shaped to define an eye 180, 280 that facilitates this affixation.

Similarly to winch 40, for winch 140, 240, in response to rotation in a forward rotational direction, tether 44 is drawn into the winch and is wound around the respective spool 142, 242. Further similarly to winch 40, the position and orientation at which spool 142, 242 is coupled to mount 146, 246, respectively, inhibits subsequent unwinding of tether 44 from the spool in response to pulling of the end portion away from the spool. In this way, pulling force applied to spool 142, 242 does not result in substantial rotational movement, yielding a stable rotational orientation of winch 140, 240. That is, the position and orientation at which spool 142, 242 is coupled, respectively, to mount 146, 246 at least in part precludes the need for adjustment mechanism 136, 236 to comprise a discrete locking mechanism (e.g., a discrete actuatable locking mechanism).

For some applications, spool 42 is fixedly coupled to mount 46 in a position and an orientation that provides at least one stable rotational orientation (e.g. exactly one stable rotational orientation) of the mount at which the pulling is inhibited from rotating the mount in the reverse rotational direction about rotation axis d48. That is, depending on an initial rotational orientation of winch 40, application of a pulling force to end portion 62 of tether 44 can rotate the winch almost one complete turn until the winch reaches a stable position. In contrast, spool 142, 242 is fixedly coupled to mount 146, 246 in a position and an orientation that provides at least two stable rotational orientations of the mount at which pulling is inhibited from rotating the mount in the reverse rotational direction about rotation axis d148, d248. That is, depending on an initial rotational orientation of the winch, application of a pulling force to the end portion 62 of tether 44 can rotate the winch almost half a turn until the winch reaches a stable position.

Spool 142, 242 is fixedly coupled to respective mount 146, 246. For some applications, and as shown, spool 142, 242 is shaped to define a spool axis d150, d250 disposed orthogonally to rotation axis d148, d248 (e.g., passing through the rotation axis).

For some applications, winch 140, 240 is housed within housing 168, 268 such that mount 146, 246 and spool 142, 242 rotate about axis d148, d248 with respect to the housing. Further, driver interface 164, 264 can be accessible to driver 66, while winch 140, 240 is housed within housing 168, 268. Accessibility of driver interface 164, 264 while winch 140, 240 is housed within housing 168, 268 facilitates the engaging and driving of the winch, by driver 66, while the winch is housed within the housing.

Figure 5A:
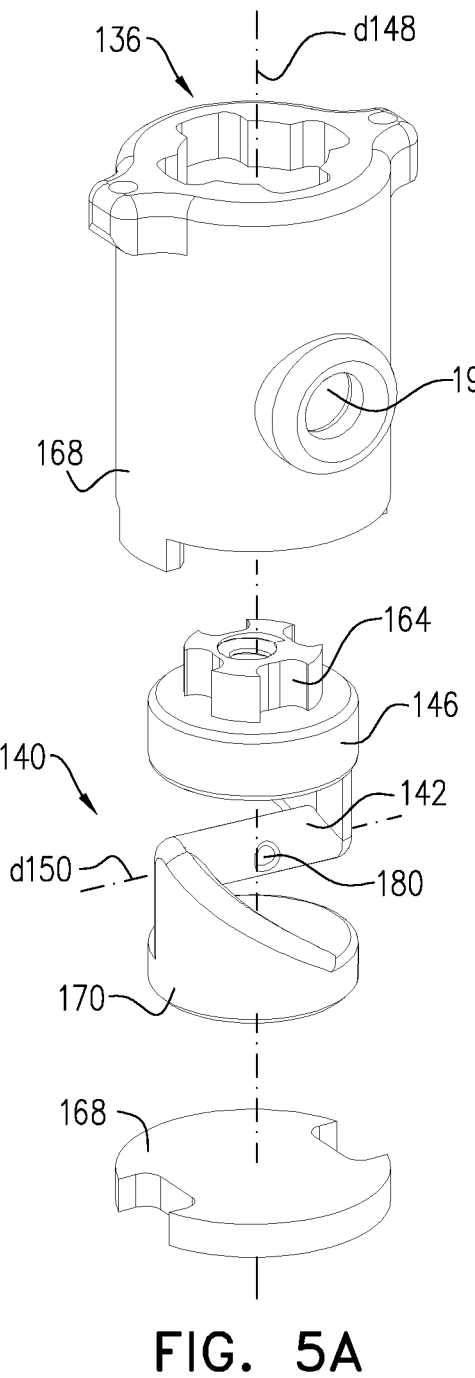
FIGS. 5A-B, 6A-C, 7A-L, and FIGS. 8A-E, 9A-C are schematic illustrations showing adjustment mechanisms, respectively comprising winches, in accordance with some applications.
Figure 5B:
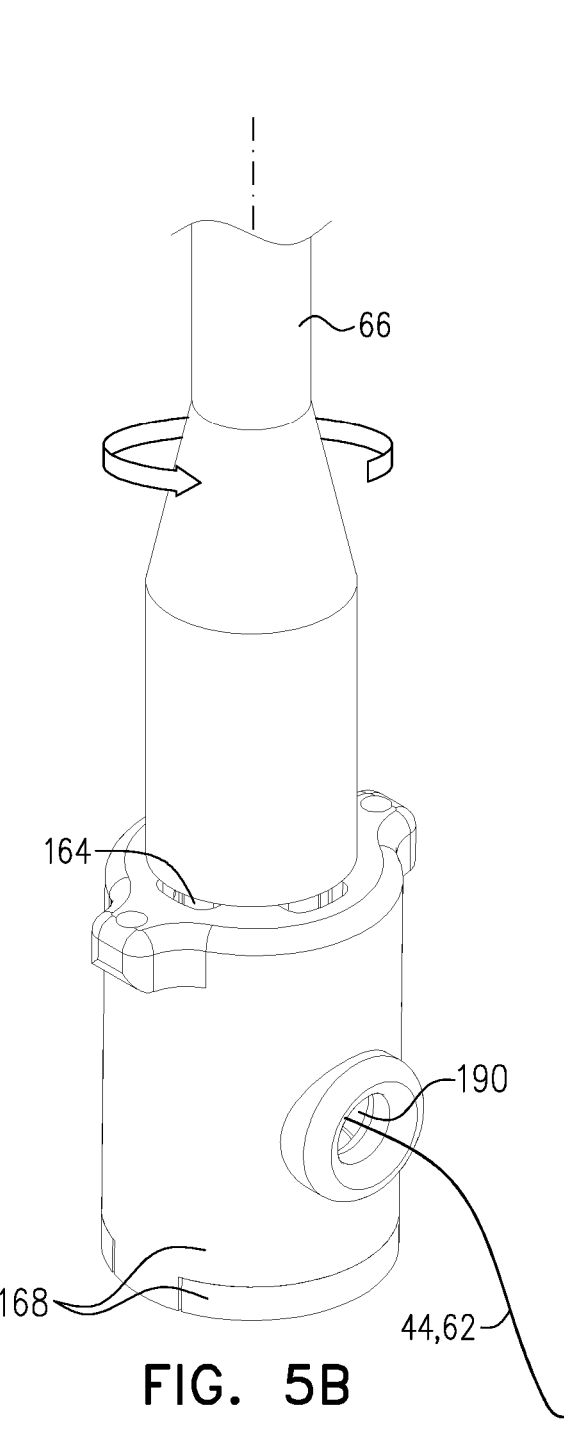
Figures 6A, 6B, 6C:
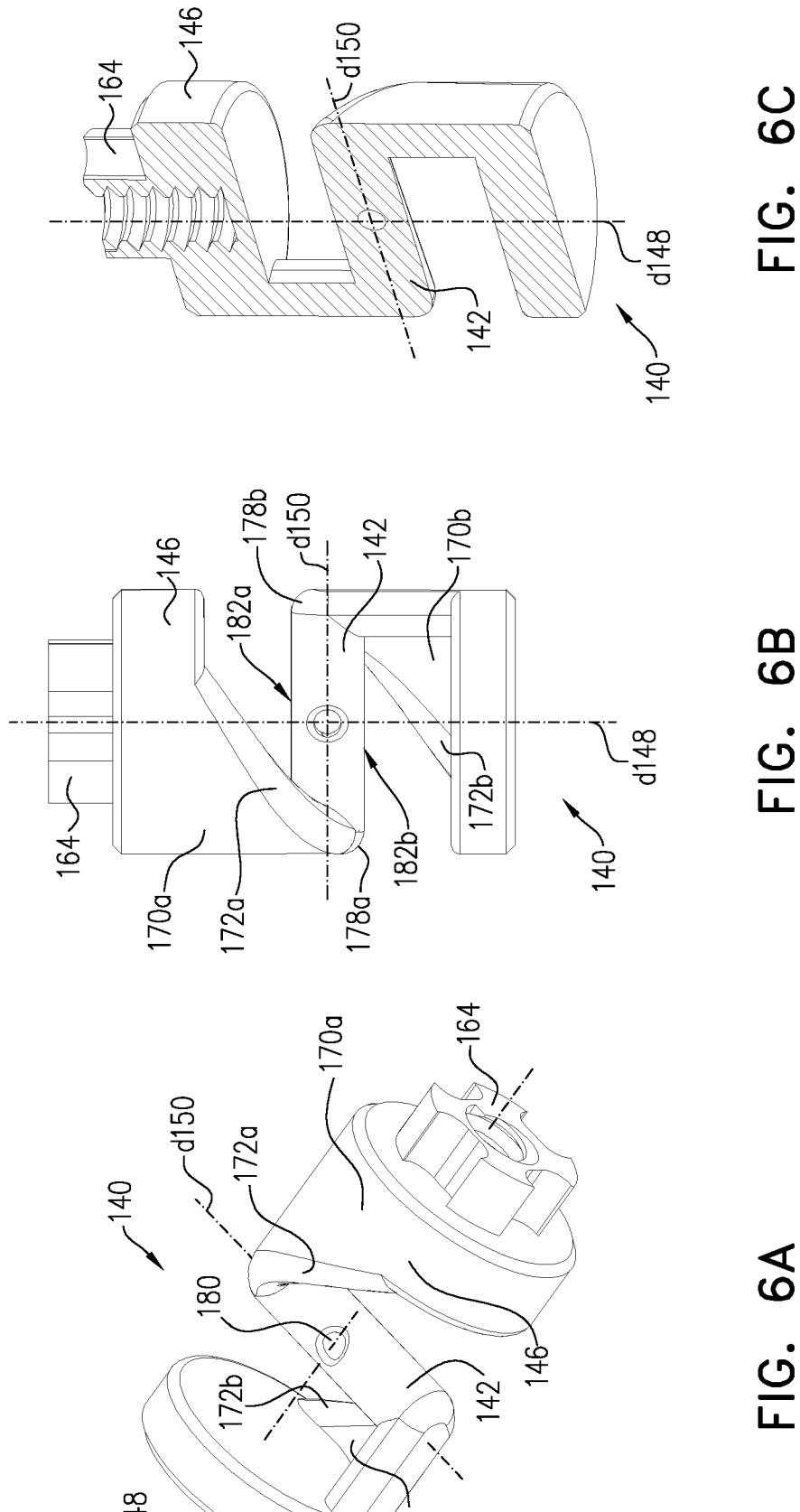

As shown in FIGS. 5A-B, housing 168 is shaped to define an aperture 190 therethrough, the aperture configured to facilitate passage of tether 44 from outside winch 140 to spool 142 as the spool draws end portion 62 of the tether toward the winch.

For some applications, and as shown, winch 140, 240 comprises at least one inclined guide 170, 270. Often, inclined guide 170, 270 is coupled to mount 146, 246. For some applications, mount 146, 246 is shaped to define guide 170, 270. For instance, guide 170, 270 can be integral to mount 146, 246 (i.e. molded from the same material). Often, and as shown, inclined guide 170, 270 is coupled to mount 146, 246 and disposed laterally from rotation axis d148, 248. In this way, inclined guide 170, 270 is positioned such that, upon rotation of mount 146, 246 in the forward rotational direction, the inclined guide guides tether 44 around spool 142, 242.

The manner in which tether 44 is guided around spool 142 is different from the manner in which the tether is guided around spool 242, as described hereinbelow.

As shown in FIGS. 7A-L, rotation of mount 146 about rotation axis d148 causes tether 44 to wind around the spool—i.e., around spool axis d150. Often, and as shown, inclined guide 170 is shaped such that, upon driving of driver interface 164 by driver 66, the inclined guide rotates with the mount about rotation axis d148. For some applications, and as shown, inclined guide 170 defines a guide surface 172 that extends helically around and along rotation axis d148. Contact of tether 44 with guide surface 172 along a helical slope of inclined guide 170 facilitates translation of circular movement of mount 146 into wrapping of tether 44 about spool 142.

For example, and as shown in FIGS. 7A-L, winch 140 includes a first inclined guide 170a and a second inclined guide 170b. First inclined guide 170a is positioned such that, upon rotation of mount 146 in the forward rotational direction, the first inclined guide guides tether 44 to a second side 182b of spool 142. Second inclined guide 170b is positioned such that, upon forward rotation of mount 146, the second inclined guide guides tether 44 to a first side 182a of spool 142. Often, first inclined guide 170a is disposed generally on first side 182a of the spool, and second inclined guide 170b is disposed generally on second side 182b of the spool.

In some applications, and as shown in FIGS. 7A-L, guiding of tether 44, by respective inclined guides 170a and 170b, to respective sides 174, 176 of spool 142, is facilitated by the winch being shaped to define two shoulders: a first shoulder 178a at which first inclined guide 170a is coupled to a second side 182b of spool 142, and a second shoulder 178b at which second inclined guide 170b is coupled to a first side 182a of spool 142.

For some applications, and as shown, inclined guides 170a, 170b are positioned such that, upon forward rotation of mount 146, the first inclined guide guides tether 44 over first shoulder 178a to second side 182b of the spool, and the second inclined guide guides the tether over second shoulder 178b to the first side 182a of the spool.

For instance, as shown in FIGS. 7A-D, forward rotation of winch 140 initially causes tether 44 to contact inclined guide 170a at guide surface 172a. Continued forward rotation of winch 140 causes tether 44 to be guided along guide surface 172a, towards first shoulder 178a. As shown in FIG. 7E, continued forward rotation of winch 140 causes tether 44 to be guided further, over first shoulder 178a, such that the tether becomes draped over second side 182b of spool 142. As is evident in FIG. 7F, one half turn of forward rotation of winch 140 facilitates wrapping tether 44 about at least one half of a circumference of spool 142.

As shown in FIGS. 7G-K, continued forward rotation of winch 140 causes tether 44 to climb guide surface 172*b*, towards second shoulder 178*b*, such that the tether becomes draped over first side 182*a* of spool 142. In this way, one full turn of forward rotation of winch 140 facilitates wrapping tether 44 about at least one full circumference of spool 142.

Figures 7A, 7B, 7C:
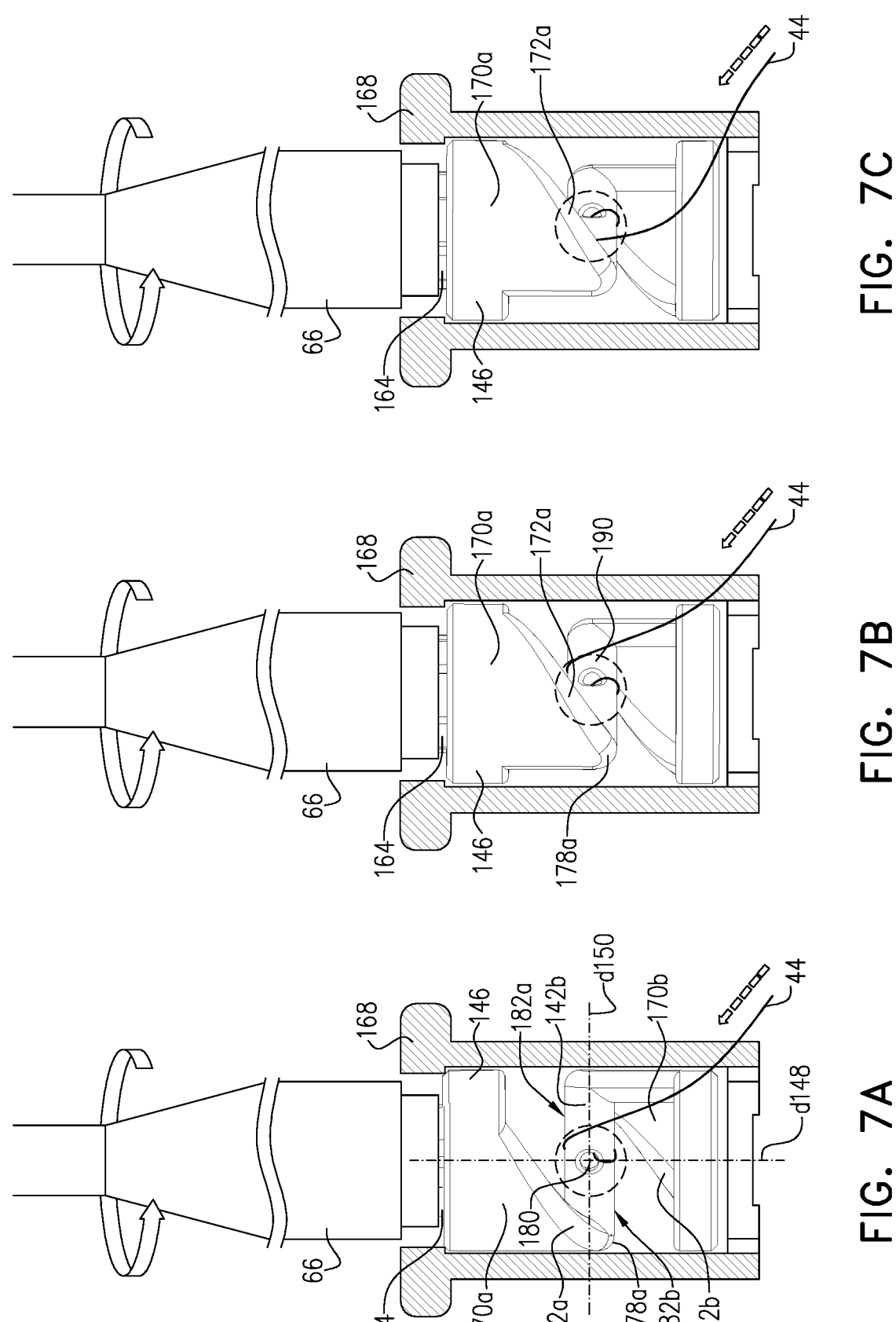
Figures 7D, 7E, 7F:
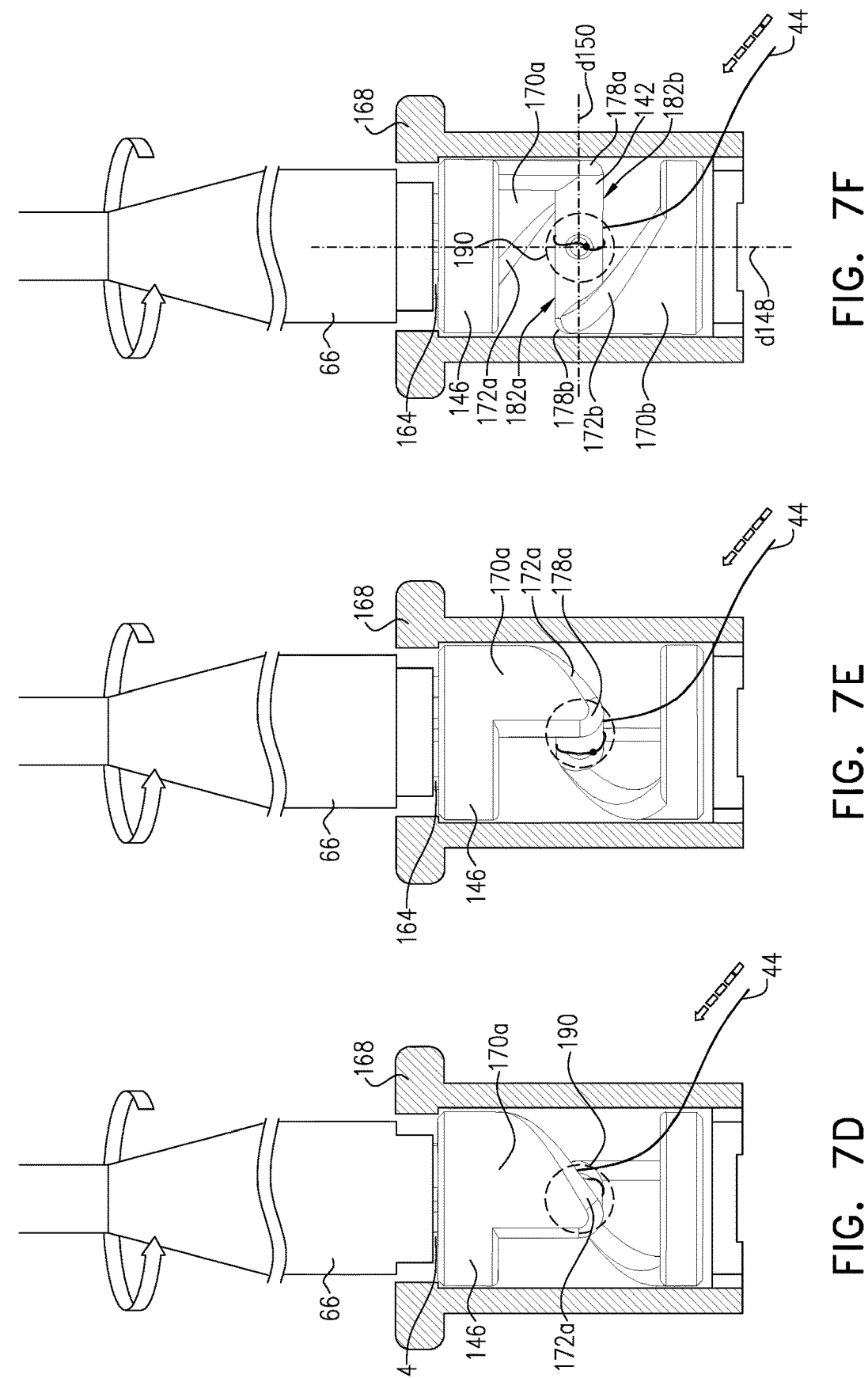
Figures 7G, 7H, 7I:
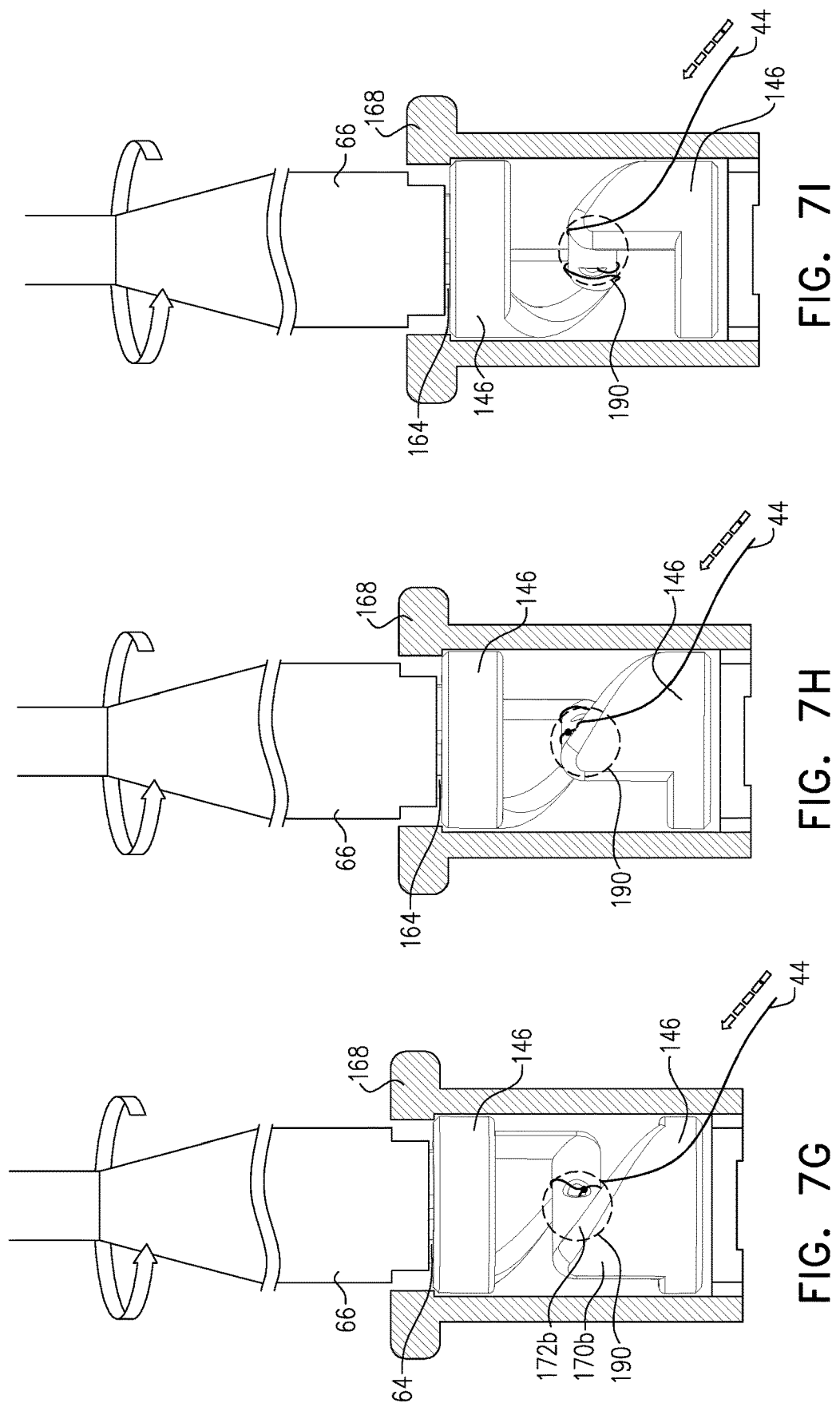
Figures 7J, 7K, 7L:
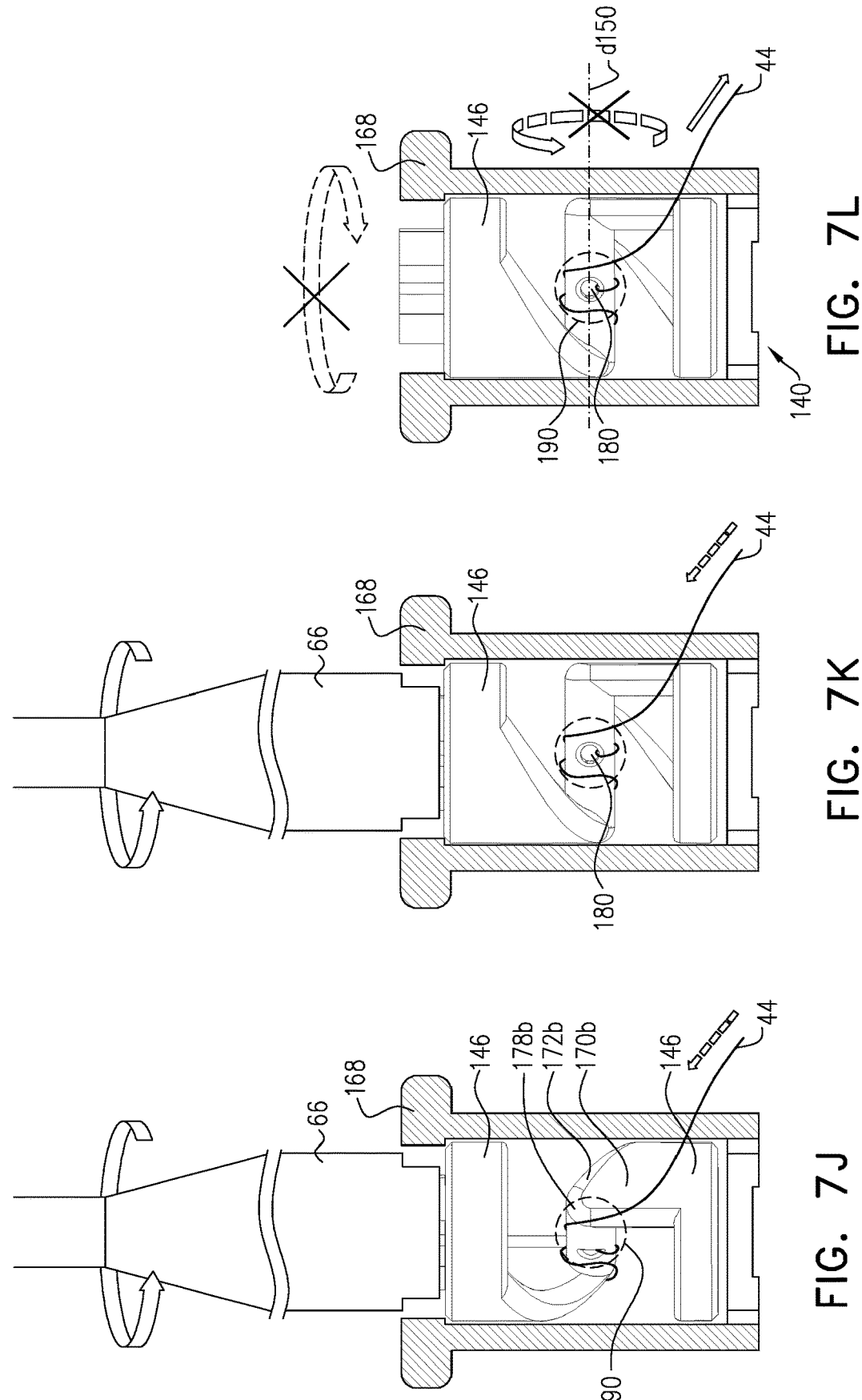

As shown in FIG. 7L, when a rotational force is no longer applied to winch 140 (e.g., upon disengagement of driver 66 from the winch), if a pulling force (solid arrow in FIG. 7L) is applied to tether 44, it is not significantly translated into reverse rotation of winch 140, nor into unwinding of the tether. It is hypothesized that the pulling force is not significantly translated into reverse rotation of the winch at least in part since spool 142 is fixedly coupled to mount 146 orthogonally to rotation axis d148. That is, tension on tether 44 "attempts" to rotate spool 142 about spool axis d150 (represented by the broken arrow in FIG. 7L), but that axis is orthogonal to the axis d148 about which mount 146 is configured to rotate. Winch 140 is unable to rotate about axis d150 within housing 168 (represented by the striking out of the broken arrow in FIG. 7L). Therefore, tension applied to tether 44 during winding of the winch does not automatically unwind the winch upon subsequent disengagement of driver 66.

It is further hypothesized that this at least in part obviates a need for an adjustment mechanism 136 to comprise a discrete locking mechanism (e.g., a discrete actuatable locking mechanism). It is further hypothesized that this thereby contributes to the simplicity and ease of use of winch 140.

Reference is again made to FIGS. 8A-E, 9A-C, which are schematic illustrations showing winch 240 comprising mount 246 and spool 242, in accordance with some applications.

While the shape of inclined guides 270*a*, 270*b* of winch 240 is similar to that of inclined guide 170 of winch 140, guides 270*a*, 270*b* of winch 240 are not configured to directly contact tether 44, but instead are configured to indirectly guide the tether by guiding an eyelet 288 that defines an aperture 290 through which the tether passes. For some applications, aperture 290 is configured to facilitate passage of tether 44 from outside winch 240 to spool 242 as the spool draws the end portion 62 of the tether toward the winch.

Further for some applications, and as described in more detail hereinbelow, eyelet 288 is mechanically engaged with guide surfaces 272*a*, 272*b* of guides 270*a*, 270*b* such that, upon rotation of mount 246 in the forward rotational direction, the guides guide the eyelet linearly parallel to rotation axis d248.

Figures 8A, 8B:
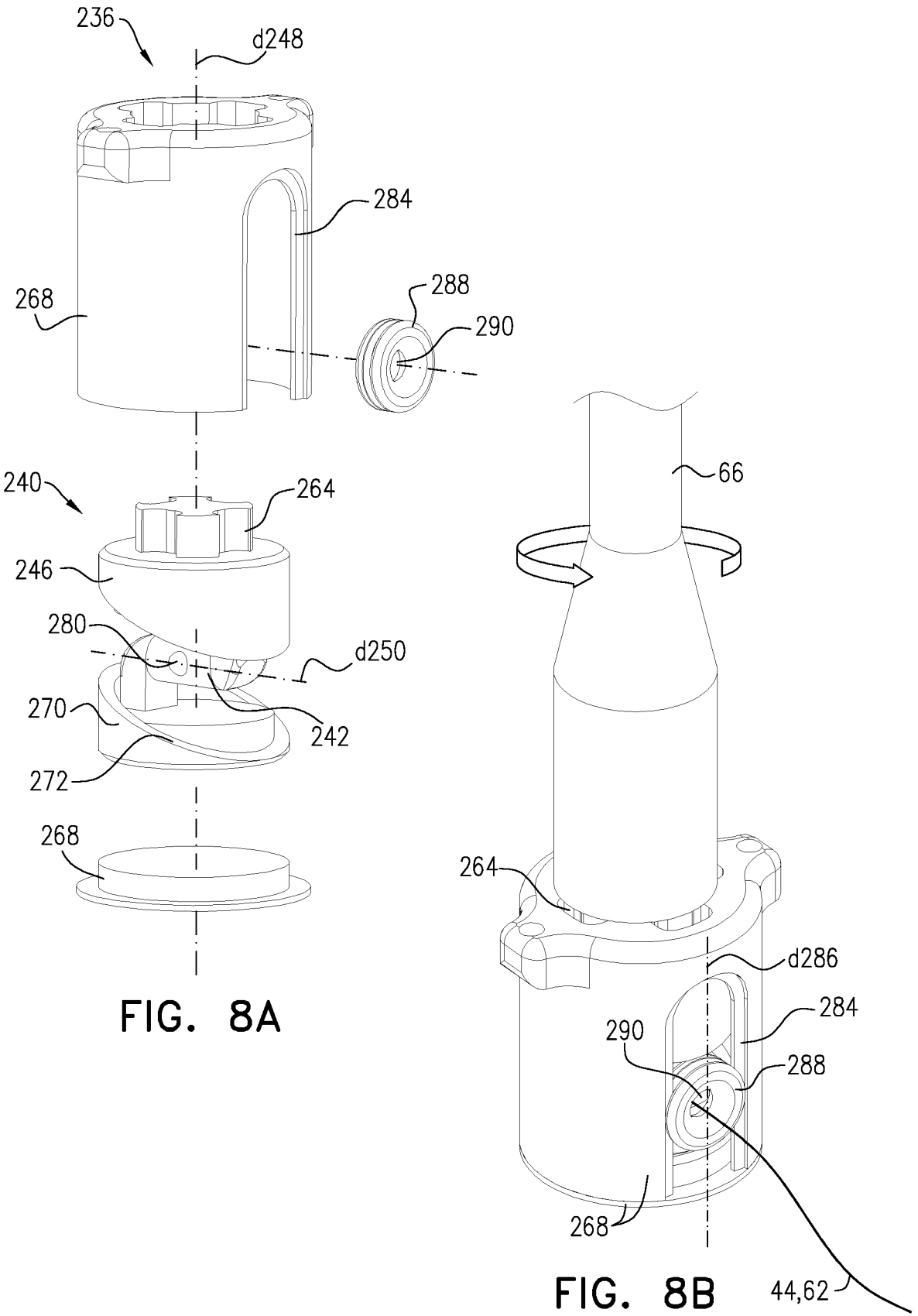
Figures 8C, 8D, 8E:
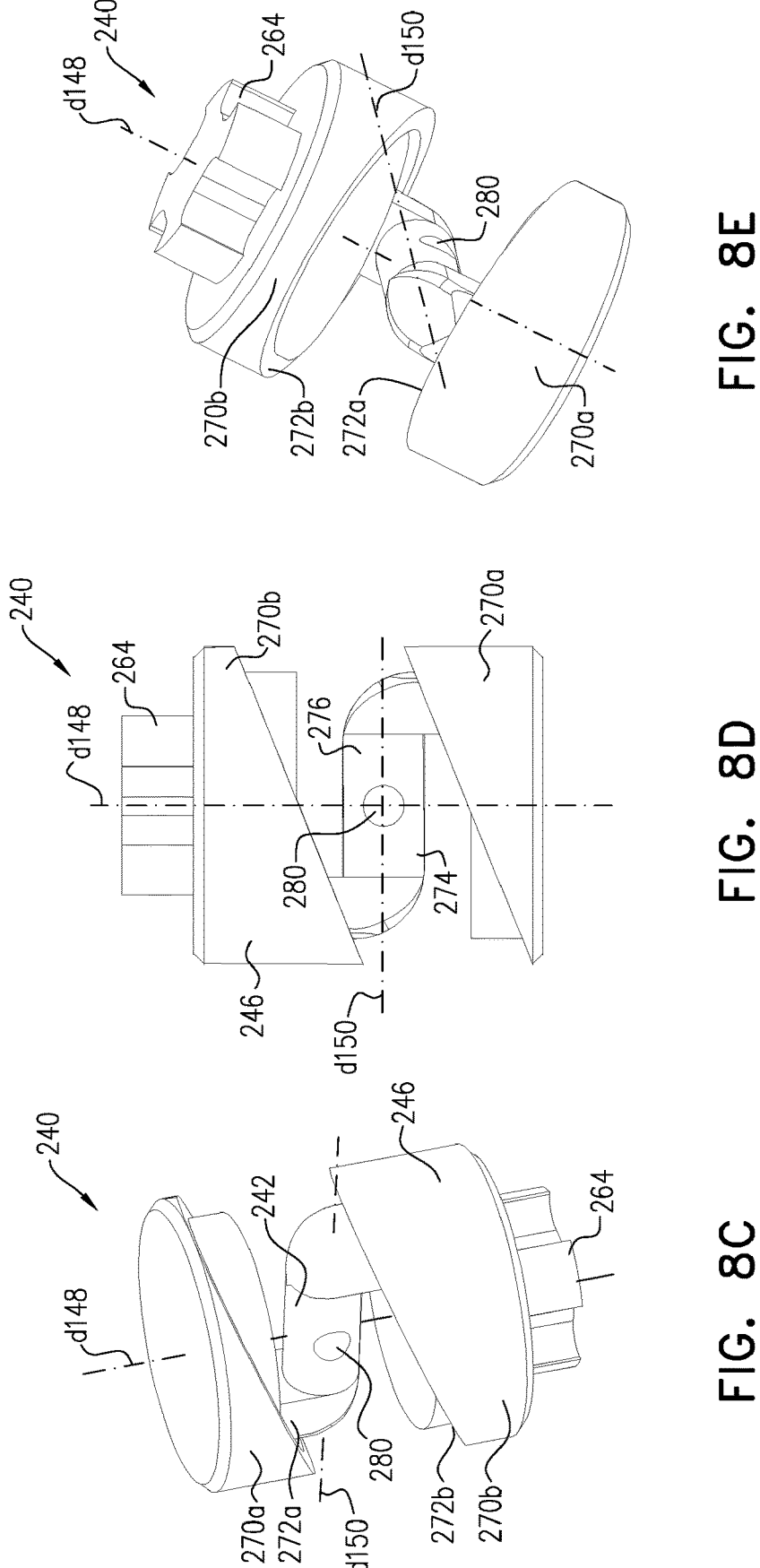
Figure 9C:
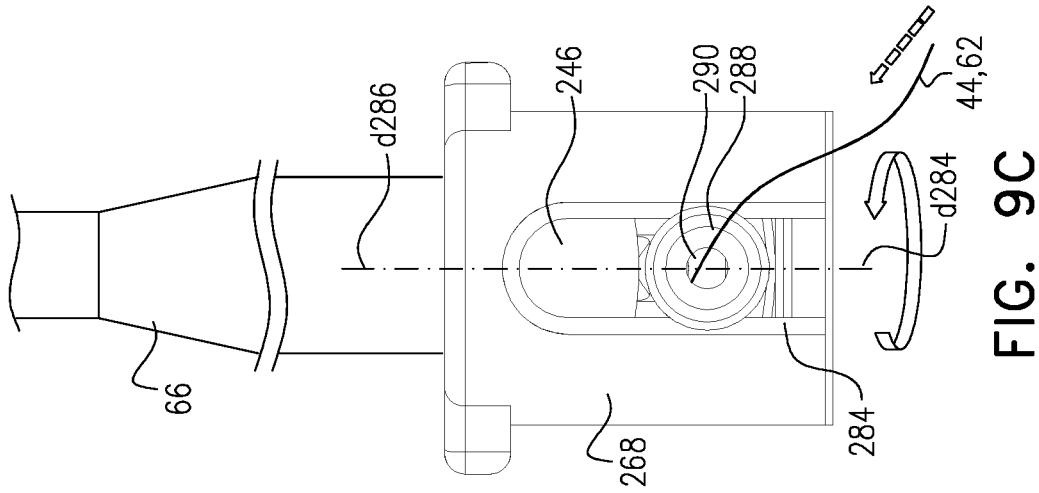
Figure 9B:
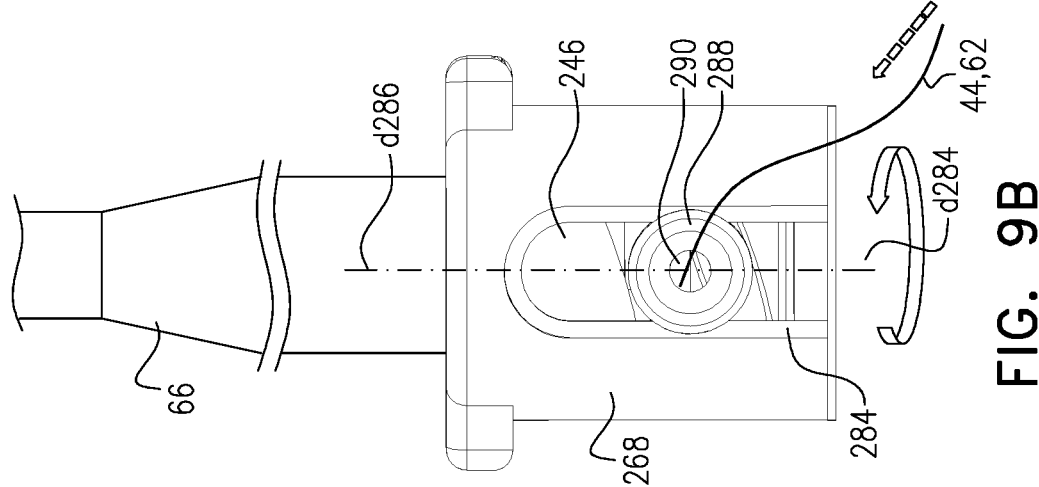
Figure 9A:
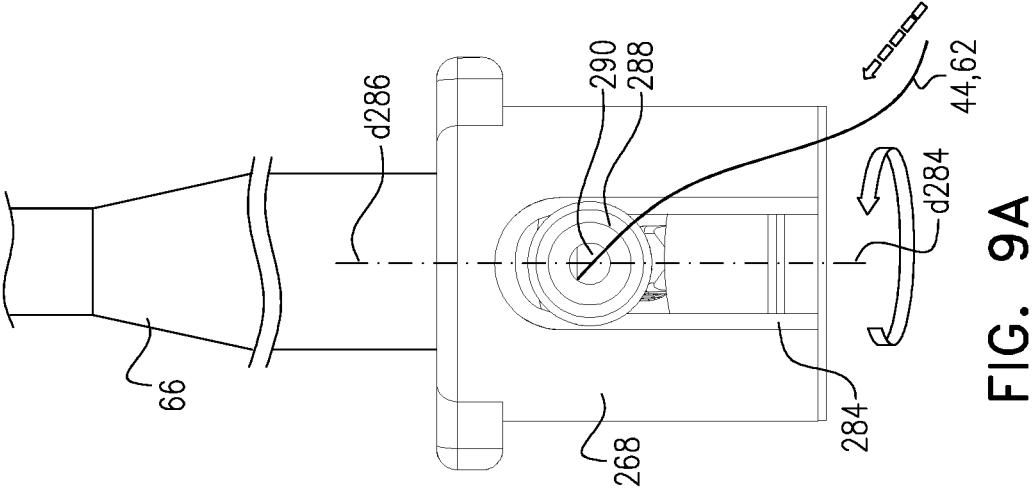

As shown in FIGS. 8A, C-D, winch 240 comprises inclined guides 270*a*, 270*b* that each extend helically around and along rotation axis d248, typically parallel with each other. For some applications, inclined guides 270*a*, 270*b* are coupled to mount 246. For some applications, mount 246 is shaped to define guides 270*a*, 270*b*. For instance, guides 270*a*, 270*b* can be integral to mount 246 (i.e. molded from the same material).

For some applications, and as shown in FIG. 8A-B, adjustment mechanism 236 further comprises a housing 268 that houses winch 240. For some applications, housing 268 is configured to facilitate rotation of mount 246 and spool 242 about rotation axis d248, with respect to the housing.

For some applications, adjustment mechanism 236 (e.g., housing 268 thereof) defines a track 284 along a track axis d286, which is typically parallel to rotation axis d248. Eyelet 288 is mechanically engaged with track 284, such that the eyelet is linearly slidable along the track. The mechanical engagement of eyelet 288 with (i) guide surfaces 272*a* and 272*b*, and (ii) track 284, translates rotation of winch 240 (including guides 270*a* and 270*b*) into reciprocating movement of the eyelet along the track.

This movement of the eyelet 288 guides tether 44 around one side and then the other side of spool 242. Thereby, (1) longitudinal motion of eyelet 288 and end portion 62 of tether 44 in relation to housing 268, and (2) forward rotation of mount 246, winds the tether around spool 242.

Similarly to as described herein above in reference to winch 140, when a rotational force is no longer applied to winch 240 (e.g., upon disengagement of driver 66 from the winch), if a pulling force is applied to tether 44, it is not significantly translated into reverse rotation of winch 240, nor into unwinding of the tether. As in winch 140, spool axis d250 is orthogonal to the axis d248 about which mount 246 is configured to rotate. Therefore, pulling on tether 44 applies a pulling force to spool 142, 242 but the pulling force is applied orthogonally to axis d148, d248, and does not result in rotational movement, yielding a stable rotational orientation, respectively of winch 140, 240. Thus, winch 240 is unable to rotate about axis d250 within housing 268, similarly obviating both a locking mechanism and a locking-actuating mechanism from winch 240 and contributing to the simplicity and ease of use of the winch.

Figure 10:
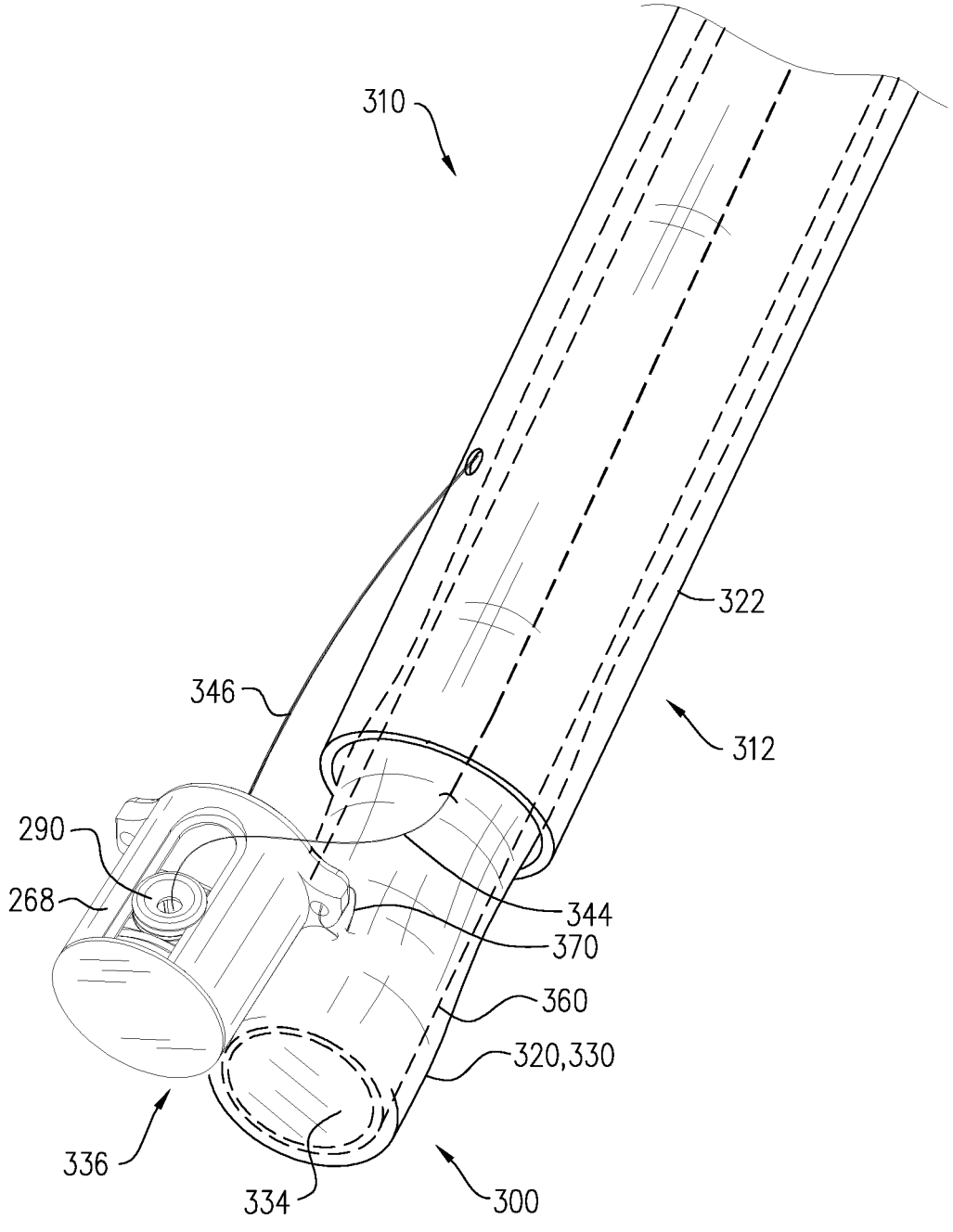
FIG. 10 is a schematic illustration of a multi-component system comprising an implant, and a delivery tool for delivering the implant to a heart of a subject, in accordance with some applications.

Reference is made to FIG. 10, which is a schematic illustration of a multi-component system 310 comprising an implant 300, and a delivery tool 312 for delivering the implant 300 to a heart 390 of a subject, in accordance with some applications.

Implant 300 comprises an adjustment mechanism 336 that comprises a winch. Adjustment mechanism 336 can comprise any of the other adjustment mechanisms described herein, but for the purpose of illustration, it is shown in FIGS. 10-11F as comprising adjustment mechanism 236.

FIG. 10 shows a distal portion of system 310 comprising annuloplasty structure 320 (e.g., an annuloplasty band), disposed partially within a catheter 322 of tool 312. For some applications, and as shown, structure 320 comprises a sleeve 330 that defines an elongate lumen circumscribed by a lateral wall (e.g., the interior of structure 320 is shaped as an elongate lumen). For some applications, sleeve 330 defines an end wall 334 of annuloplasty structure 320.

Sleeve 330 is often a flexible sleeve comprising a braided fabric mesh, e.g., comprising polyethylene terephthalate (such as Dacron™). Sleeve 330 is often configured to be anchored partially or completely around a cardiac valve annulus 388, and subsequently contracted so as to adjust a perimeter of the annulus (i.e., to circumferentially tighten the annulus).

Annuloplasty structure 320 comprises a flexible elongate tether 344 that extends, along at least a portion of sleeve 330, e.g., to an end portion 362 of the tether. The portion of the sleeve along which the tether extends is thereby a contracting portion of the sleeve. For some applications, tether 344 generally corresponds to tether 44 described hereinabove, mutatis mutandis.

Figure 11A:
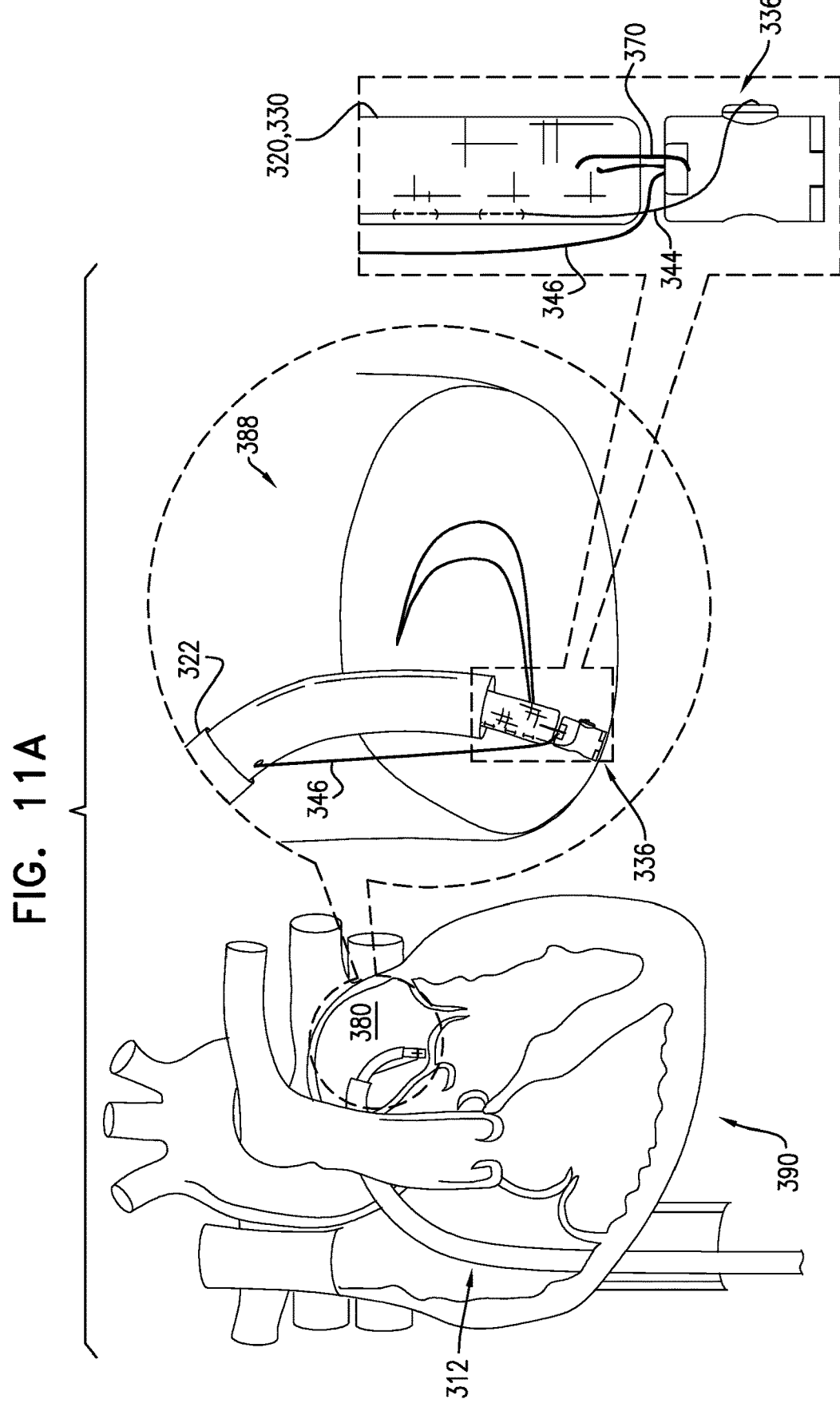
FIGS. 11A-F are schematic illustrations showing use of an adjustment mechanism in the system comprising the implant and the delivery tool, in accordance with some applications.

For some applications, and as shown in FIG. 11A, sleeve 330 (i.e. an outer, lateral surface thereof) is coupled to the winch of by a connector 370 (e.g., by stitches) such that drawing of end portion 362 of tether 344 toward and into the winch longitudinally contracts the contracting portion.

Tether 344 can comprise a wire, a ribbon, a rope, or a band, and can comprise a flexible and/or superelastic material, e.g., nitinol, polyester, stainless steel, or cobalt chrome. For some applications, the wire comprises a radiopaque material. For some applications, tether 344 comprises a braided polyester suture (e.g., Ticron). For some applications, tether 344 is coated with polytetrafluoroethylene (PTFE). For some applications, tether 344 comprises a plurality of wires that are intertwined to form a rope structure.

Adjustment mechanism 336 facilitates axial contracting (and re-expanding) of annuloplasty structure 320. As described for other adjustment mechanisms described herein, adjustment mechanism 336 comprises a winch that comprises a spool, arranged such that rotation of the winch winds tether 344 around the spool, drawing the tether into the winch. This thereby contracts implant structure 320. For some applications, adjustment mechanism 336 comprises a housing within which the winch is disposed, as described hereinabove. Adjustment mechanism 336 (e.g., the spool thereof) is coupled to tether 344. When the winch of the adjustment mechanism is rotated (e.g., with respect to its housing), the winch adjusts a length of structure 320 by applying tension to tether 344 (or by releasing the tension). Particularly, drawing of end portion 362 of tether 344 toward adjustment mechanism 336 reduces a length of structure 320.

System 310 often comprises a flexible, longitudinal guide member 346 (e.g., a wire) coupled to a portion of the winch. For example, in a delivery state shown in FIG. 10, structure 320 is disposed at a distal portion of the catheter, and guide member 346 is coupled to the winch of adjustment mechanism 336. For some applications, and as shown, guide member 346 extends from adjustment mechanism 336 (e.g., the driver interface thereof) and proximally through catheter 322 (e.g., through a parallel side-lumen of the catheter). For some applications, a proximal portion of guide member 346 is accessible from outside the body of the subject.

Reference is made to FIGS. 11A-F, which are schematic illustrations showing use of adjustment mechanism 336 in system 310 comprising implant 300 and delivery tool 312, in accordance with some applications.

For some applications, and as shown in FIG. 11A, delivery tool 312 comprises a catheter 322, the distal portion of the catheter being advanceable (e.g., transluminally steerable) into the body of the subject. For some applications, structure 320 is advanced into left atrium 380 using catheter 322. For some applications, and as shown, this is performed by advancing catheter 322 with structure 320 disposed therein. Optionally, catheter 322 can be advanced first, and structure 320 (or another implant) can be subsequently advanced through the catheter. While a transfemoral transseptal approach to the mitral valve is shown in FIG. 11A, the scope herein includes alternate approaches to the mitral valve, to the tricuspid valve, to other locations in (e.g., valves of) the heart, and to other locations in the body.

For some applications, and as shown, annuloplasty structure 320 can be advanced with an anchor deployment manipulator 360 disposed in an anchor channel 350, within the interior of the annuloplasty structure. Optionally, anchor deployment manipulator 360 can be introduced into the interior after advancement of annuloplasty structure 320 (or another implant).

Figure 11B:
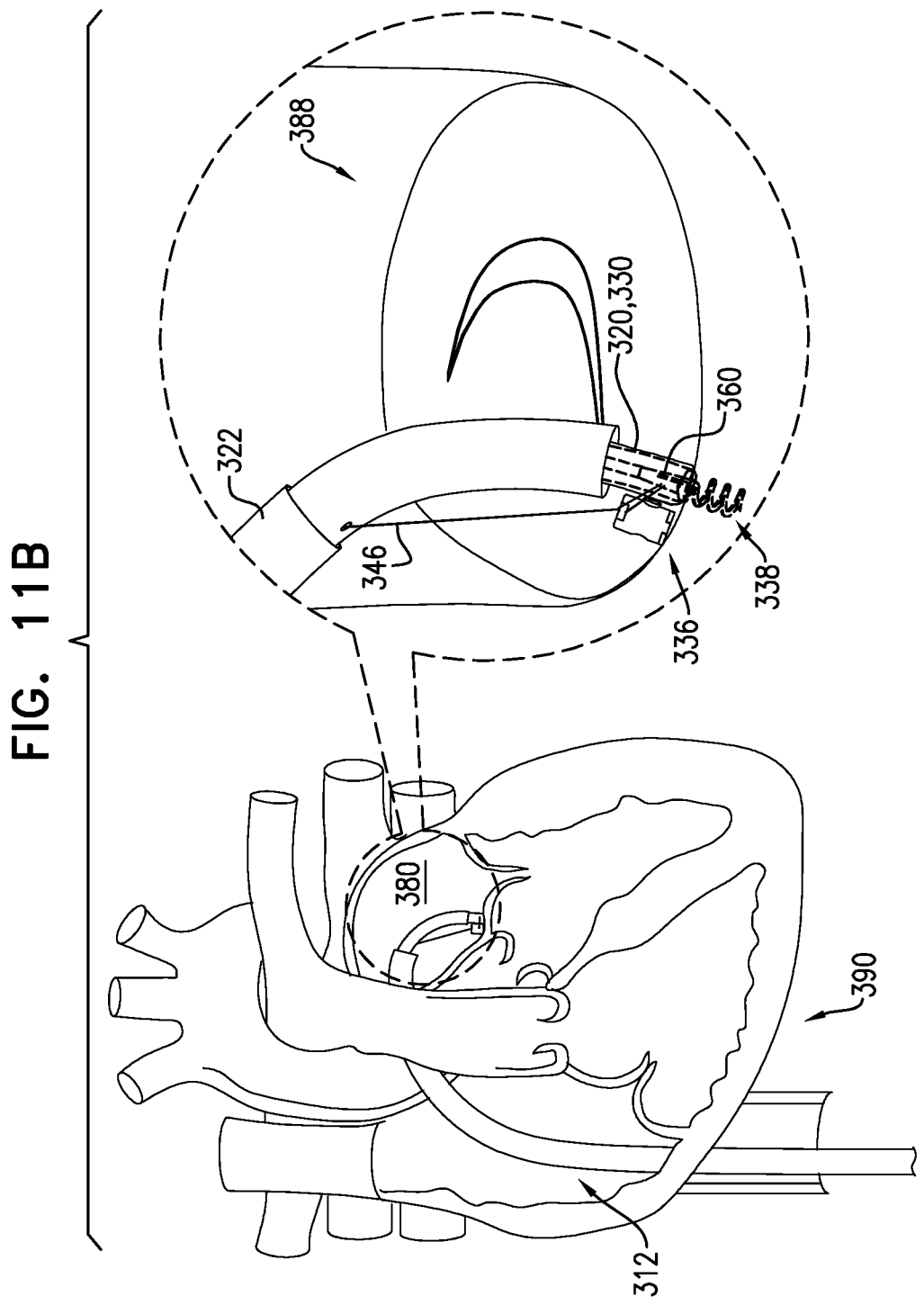

Subsequent to exposure of at least adjustment mechanism 336 (and typically at least end wall 334 of sleeve 330) from catheter 322, the winch is moved away from end wall 334 (FIG. 11B). For some applications, this is achieved by guide member 346 being moved proximally such that adjustment mechanism 336 (and the winch thereof) moves (e.g., translates, deflects, and/or rotates) away from the longitudinal axis of the sleeve, often to become disposed laterally from sleeve 330.

For some applications, connectors 370 facilitate this technique by flexibly and/or articulatably coupling adjustment mechanism 336 to sleeve 330. For some such applications, guide member 346 is also tensioned or relaxed in order to reposition the adjustment mechanism.

The movement of adjustment mechanism 336 (and the winch thereof) away from end wall 334 of sleeve 330 advantageously facilitates (1) advancement of the structure to the mitral valve while adjustment mechanism 336 is disposed on the longitudinal axis of sleeve 330 (e.g., collinearly with the sleeve), so as to maintain a small cross-sectional diameter of the structure for transluminal delivery; and (2) subsequently movement of the adjustment mechanism away from the longitudinal axis, e.g., so as to allow end wall 334 of the sleeve to be placed against the annulus, and/or so as to allow anchor 338 to be driven through the end wall of the sleeve (FIG. 11B).

For some applications, implant 300 comprises at least one anchor 338 configured to anchor tether 344 (e.g., end portion 362 thereof) to a tissue of the subject. For some applications, anchors 338 are deployed from a distal end of manipulator 360 into tissue of a subject. For example, and as shown in FIG. 11B, anchor deployment manipulator 360 is advanced into a lumen of sleeve 330 (typically within anchor channel 350), and, from within the lumen, deploys the anchors through a wall of the sleeve and into cardiac tissue. This process is repeated for several anchors 338 along sleeve 330, in order to anchor the sleeve around a portion of the valve annulus. For some applications, annuloplasty structure 320 is implanted using techniques described, mutatis mutandis, in one or more of the following publications, each of which is incorporated herein by reference:

US Patent Application Publication 2010/0286767 to Zipory et al.,

US Patent Application Publication 2010/0280604 to Zipory et al.,

US Patent Application Publication 2012/0078355 to Zipory et al.,

US Patent Application Publication 2014/0309661 to Sheps et al.,

US Patent Application Publication 2015/0272734 to Sheps et al.,

US Patent Application Publication 2018/0049875 to Iflah et al.

As shown in FIG. 11B, anchor 338 is implanted using manipulator 360 contained within sleeve 330 of annuloplasty structure 320 while at least a portion of annuloplasty structure 320 (e.g., a proximal portion) is contained within surrounding catheter 322.

Figure 11C:
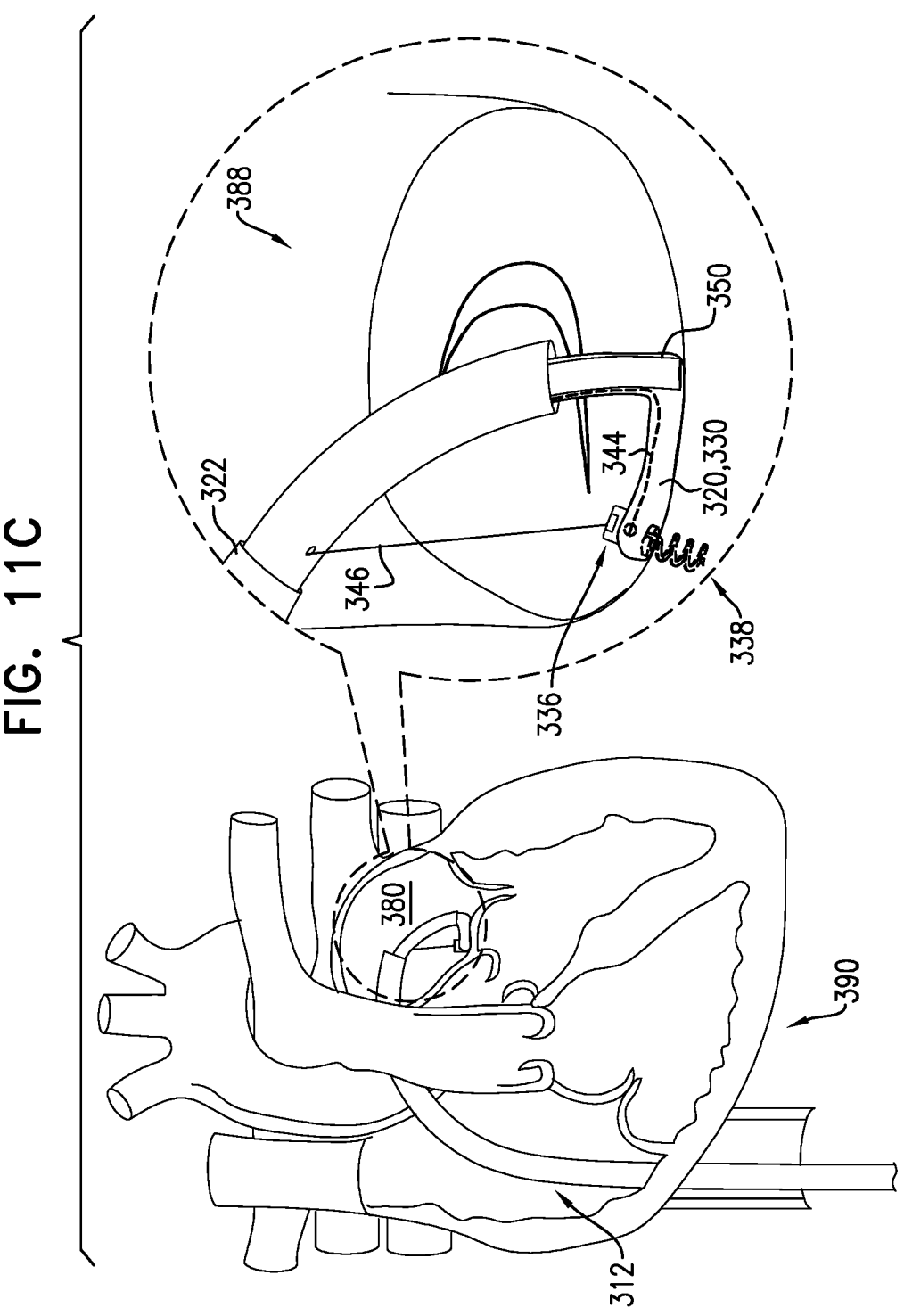

As shown in FIG. 11C, after anchor 338 is implanted, a successive portion of sleeve 330 is freed, and deployment manipulator 360 is repositioned along annulus 388 to a second site selected for deployment of a second one of anchors 338.

Figure 11D:
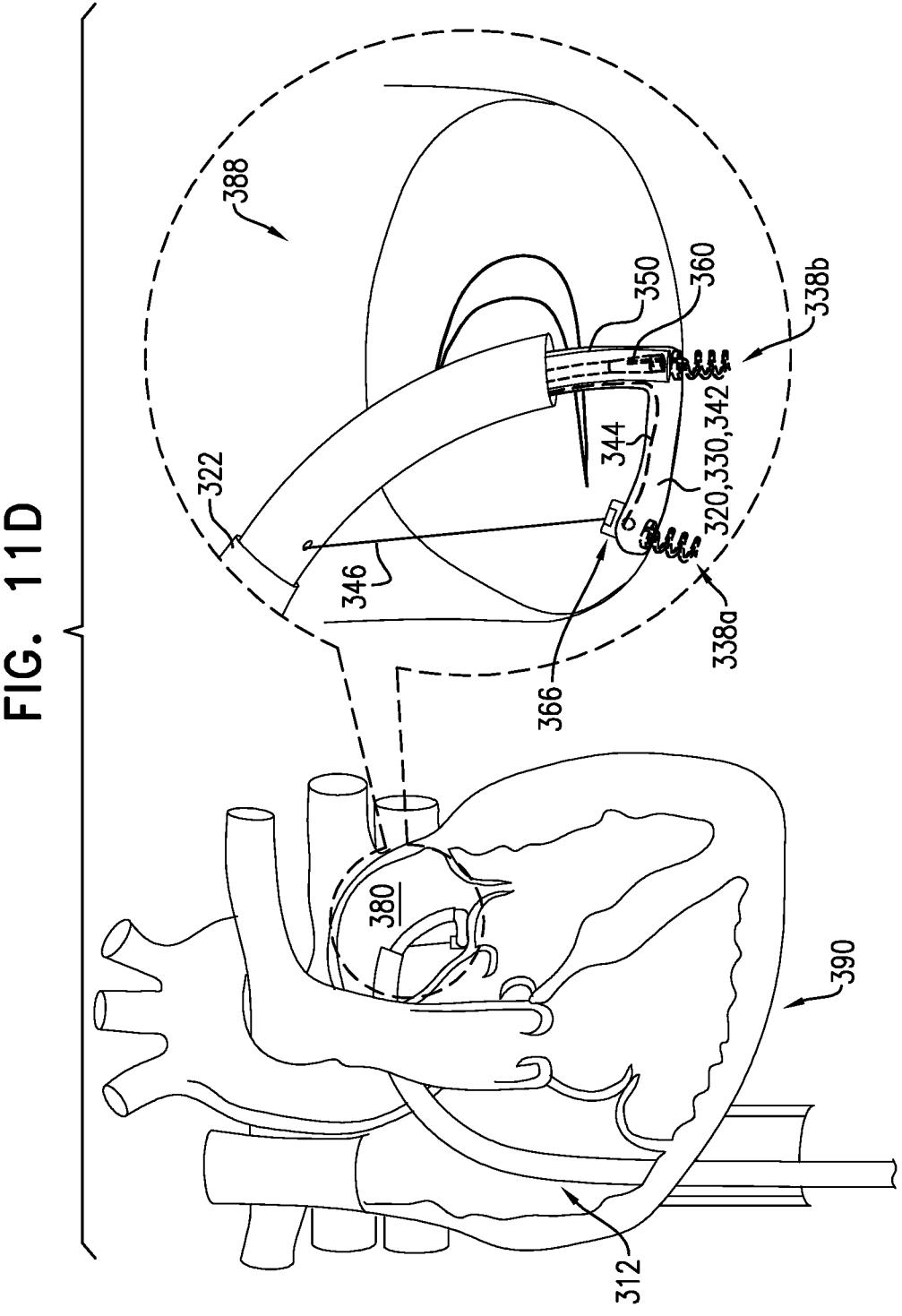

FIG. 11D shows a second tissue anchor 338 (shown as a second tissue anchor 338b) being deployed through a portion of the lateral wall of sleeve 330. The first one of anchors 338 deployed through end wall 334 is labeled as anchor 338a. Deployment manipulator 360 deploys the second tissue anchor by driving the anchor to penetrate and pass through the wall of sleeve 330 into cardiac tissue at the second site. As shown, anchor 338b is implanted while at least a portion of annuloplasty structure 320 (e.g., a proximal portion) is contained within surrounding catheter 322.

Figure 11E:
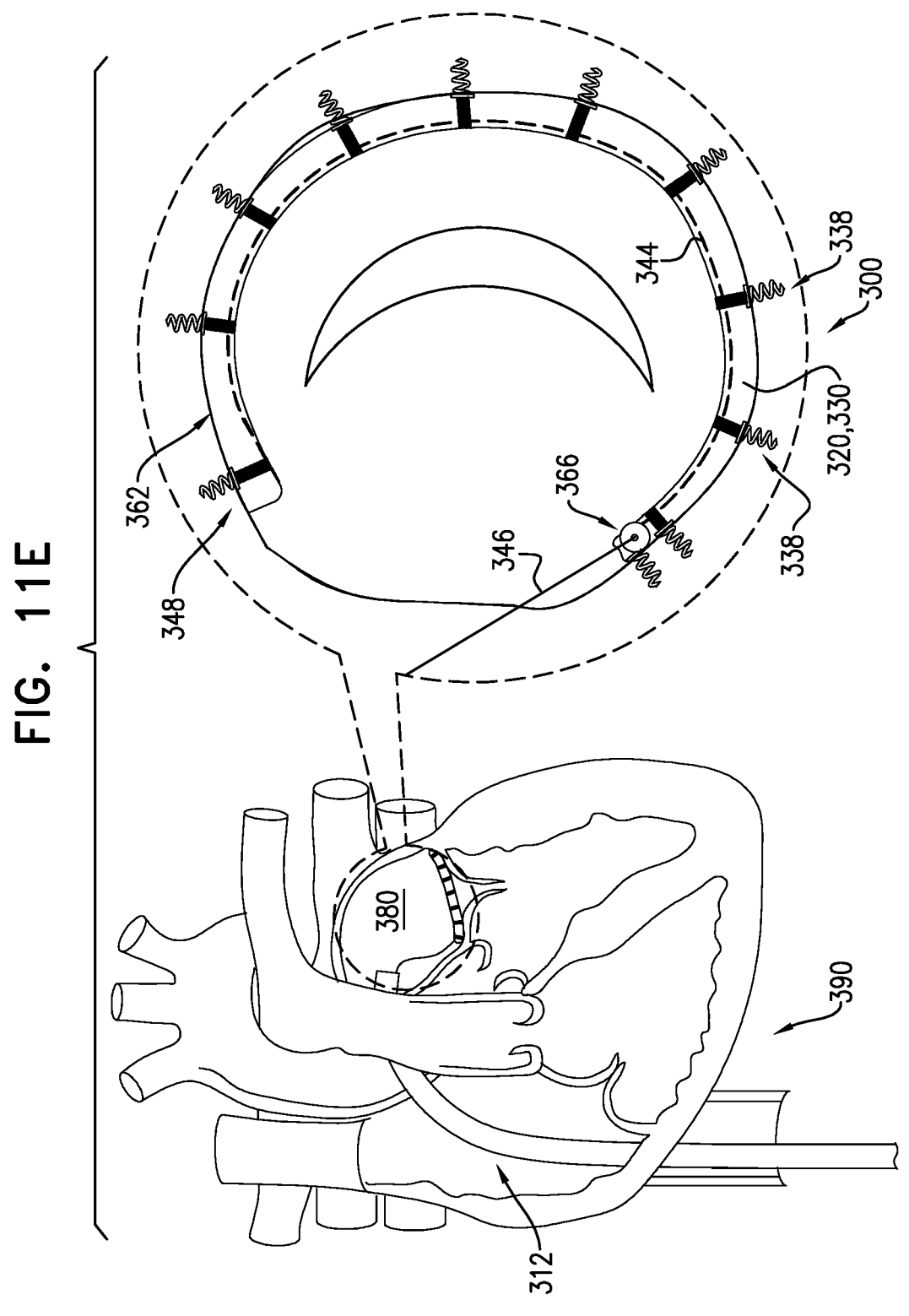
Figure 11F:
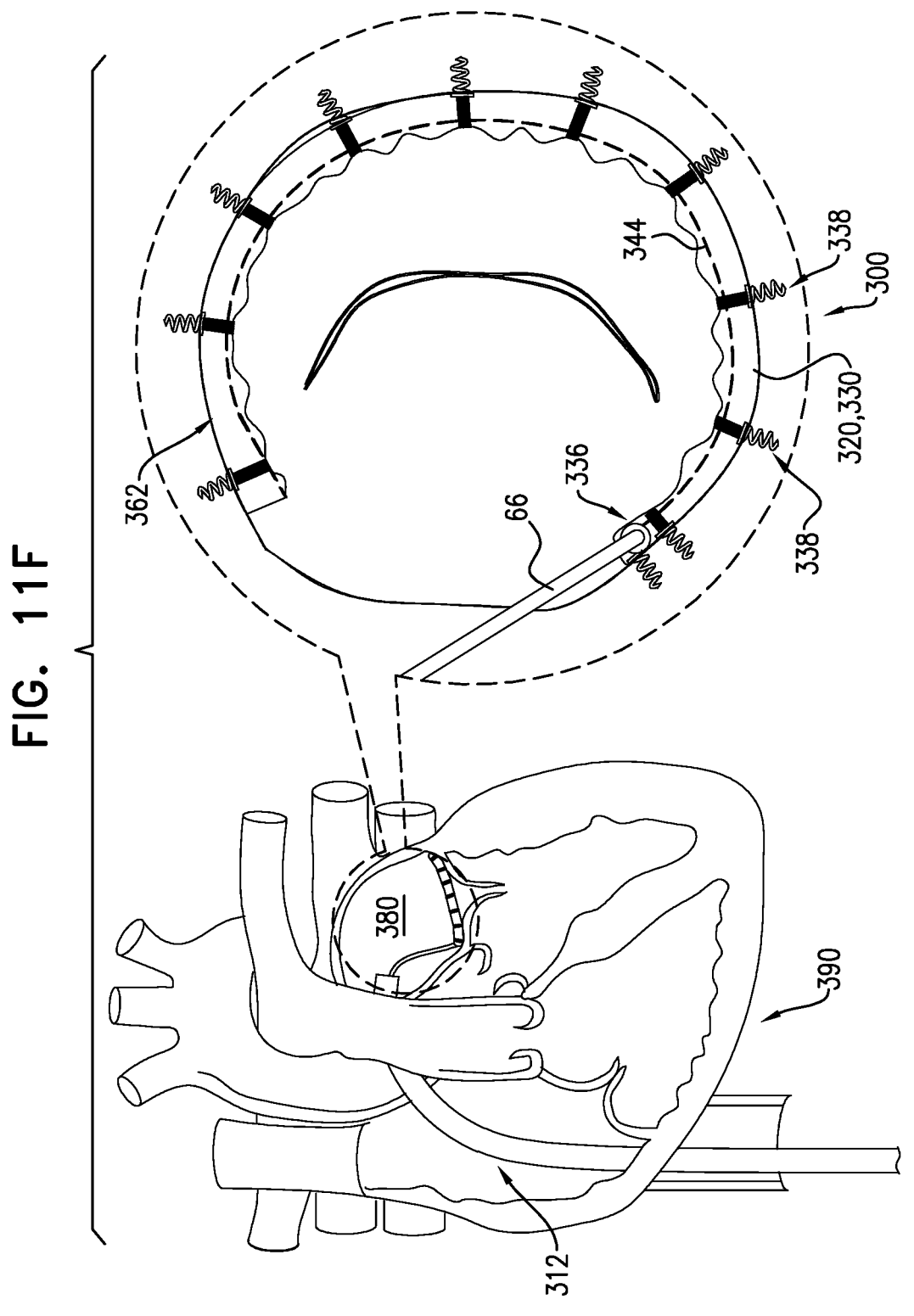

As shown in FIGS. 11E-F, a portion of the lateral wall of sleeve 330 is aligned against the tissue of in a manner in which a surface of the portion of the lateral wall is disposed in parallel with the planar surface of the tissue.

FIG. 11E shows the entire length of sleeve 330 having been anchored, via a plurality of anchors 338, to annulus 388, as described hereinabove. The deployment manipulator (i.e., deployment manipulator 360 described herein but not shown in FIG. 11E) can be repositioned along the annulus to additional sites, at which respective anchors are deployed, until the last anchor is deployed. Then, delivery tool 312 is removed, leaving behind annuloplasty structure 320, typically with guide member 346 coupled thereto.

For some applications, driver 66 is slidable over and along guide member 346. For example, FIG. 11F shows driver 66 having been advanced over and along guide member 346. As described herein above, driver 66 typically comprises a rotation tool, and is configured to engage and drive (e.g., rotate) the winch of adjustment mechanism 336, so as to tension tether 344, and thereby axially contract sleeve 330, in response to a rotational force applied to the winch.

After the degree of tension of tether 344 has been adjusted, driver 66 can be disengaged from the winch of adjustment mechanism 336, typically without actuating or otherwise activating a locking mechanism. For some applications, as described herein above in reference to winches 40, 140, and 240, adjustment mechanism 336 typically does not comprise a discrete locking mechanism (e.g., a discrete actuatable locking mechanism). As described herein above in reference to winches 40, 140, and 240, after disengagement of driver 66 from adjustment mechanism 336, if a pulling force is applied to tether 44, the force is not significantly translated into reverse rotation of the winch of the adjustment mechanism, nor into unwinding of the tether, obviating a need for either a locking mechanism or a locking-actuating mechanism from implant 300, and contributing to the simplicity and ease of use of the implant.

For some applications, implant 300 comprises a different type of annuloplasty structure to that shown hereinabove. For example, adjustment mechanism 336 can be used, mutatis mutandis, as a component of an annuloplasty structure described in one or more of the following publications, each of which is incorporated herein by reference:
US Patent Application Publication 2015/0081014 to Gross,
US Patent Application Publication 2015/0230924 to Miller et al.,
US Patent Application Publication 2015/0105855 to Cabiri et al.,
US Patent Application Publication 2016/0113767 to Miller et al.

In the example shown, implant 300 is described as comprising an annuloplasty structure 320 that is anchored to tissue of an annulus of a native heart valve. However, it is to be noted that, for some applications, the systems, apparatuses, and techniques described herein can be used to facilitate adjustment of other implants, mutatis mutandis. For example, the adjustment mechanisms described herein can be used as a component of an artificial chorda tendinea structure, e.g., in order to adjust a length and/or tension of the artificial chorda tendinea structure. For example, the adjustment mechanisms described herein can be used instead of an adjustment mechanism of an artificial chorda tendinea structure described in one or more of the following publications, each of which is incorporated herein by reference:
US Patent Application Publication 2014/0222137 to Miller et al.,
US Patent Application Publication 2011/0288635 to Miller et al., US Patent Application Publication 2013/0096672 to Reich et al.,
US Patent Application Publication 2014/0094903 to Miller et al.

The systems, apparatuses, and techniques described herein can be used in combination with those described in US Patent Application Publication 2018/0049875 to Iflah et al., and/or U.S. Pat. No. 9,949,828 to Sheps et al., both of which are incorporated by reference herein.

The present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description. Further, each of the techniques, methods, operations, steps, etc. described or suggested herein can be performed on a living animal or on a non-living simulation, such as on a cadaver, cadaver heart, simulator (e.g. with the body parts, tissue, etc. being simulated), etc.

The invention claimed is:

1. A system comprising a transcatheterally-advanceable driver and an implant, the implant comprising:
a tether, having an end portion; and
a winch, comprising:
  a driver interface, engageable and drivable by the driver,
  a mount, coupled to the driver interface such that driving of the driver interface by the driver rotates the mount about a rotation axis, and
  a spool:
    defining a spool axis,
    coupled to the tether, the tether extending away from the winch toward the end portion, and
    fixedly coupled to the mount such that:
      rotation of the mount about the rotation axis draws the end portion of the tether toward the spool by winding the tether around the spool axis of the spool, and
      the spool axis is non-coaxial with the rotation axis.

2. The system according to claim 1, wherein:
pulling of the end portion away from the spool exerts, on the spool, a pulling force that rotates the mount, and
the spool axis being non-coaxial with the rotation axis provides at least one stable rotational orientation of the mount in which the pulling force becomes radial with respect to the rotation axis, and thereby is inhibited from rotating the mount.

3. The system according to claim 1, wherein the spool is fixedly coupled to the mount such that the spool is entirely disposed laterally from the rotation axis.

4. The system according to claim 1, wherein the spool axis is parallel with the rotation axis.

5. The system according to claim 1, further comprising a housing that houses the winch, wherein:
the housing is configured to facilitate movement of the mount and the spool about the rotation axis, with respect to the housing, and
the driver interface is accessible to the driver while the winch is housed within the housing.

6. The system according to claim 5, wherein the housing is shaped to define an aperture via which the tether extends from the spool out of the winch, the aperture having a long axis that is disposed on an aperture plane that is transverse to the rotation axis.

7. The system according to claim 1, wherein the implant further comprises at least one anchor configured to anchor the end portion of the tether to tissue of a subject.

8. The system according to claim 7, wherein the implant comprises an annuloplasty structure, and is configured such that drawing of the end portion of the tether toward the winch reduces a length of the annuloplasty structure.

9. The system according to claim 1, wherein the spool is fixedly coupled to the mount laterally from the rotation axis, such that, in a cross-section of the winch orthogonal to the rotation axis, a radius of the winch:

extends radially outward from the rotation axis toward the spool, reaches the spool at a first surface point of the spool, passes through the spool, and passes out of the spool at a second surface point of the spool.

10. The system according to claim 9, wherein, in the cross-section, the spool has a cross-sectional shape that is at least one of a trapezoid and a D-shape.

11. The system according to claim 9, wherein, in the cross-section, the first surface point of the spool is a closest point of the spool to the rotation axis.

12. The system according to claim 11, wherein, in the cross-section, the first surface point of the spool is at least 0.2 mm from the rotation axis.

13. The system according to claim 1, wherein the spool is fixedly coupled to the mount orthogonally to the rotation axis.

14. The system according to claim 13, wherein the winch comprises at least one inclined guide coupled to the mount, disposed laterally from the rotation axis, and positioned such that, upon rotation of the mount in a forward rotational direction, the at least one inclined guide guides the tether around the spool.

15. The system according to claim 14, wherein the at least one inclined guide is fixedly coupled to the mount such that, upon driving of the driver interface by the driver, the at least one inclined guide moves with the mount about the rotation axis.

16. The system according to claim 14, wherein the at least one inclined guide defines a guide surface that extends helically around and along the rotation axis.

17. The system according to claim 14, wherein:

the at least one inclined guide comprises a first inclined guide and a second inclined guide, the first inclined guide is positioned such that, upon rotation of the mount in the forward rotational direction, the first inclined guide guides the tether to a second side of the spool, and the second inclined guide is positioned such that, upon rotation of the mount in the forward rotational direction, the second inclined guide guides the tether to a first side of the spool that is opposite the second side of the spool.

18. The system according to claim 17, wherein:

the winch defines a first shoulder at which the first inclined guide is coupled to a first end of the spool, and a second shoulder at which the second inclined guide is coupled to a second end of the spool, the first inclined guide is positioned such that, upon rotation of the mount in the forward rotational direction, the first inclined guide guides the tether over the first shoulder to the second side of the spool, and the second inclined guide is positioned such that, upon rotation of the mount in the forward rotational direction, the second inclined guide guides the tether over the second shoulder to the first side of the spool.

19. The system according to claim 14, further comprising an eyelet that defines an aperture therethrough, the aperture configured to facilitate passage of the tether from outside the winch to the spool as the spool draws the end portion of the tether toward the winch, the eyelet mechanically engaged with the guide such that, upon rotation of the mount in the forward rotational direction, the at least one inclined guide guides the tether around the spool by moving the eyelet longitudinally, parallel with the rotation axis.

20. The system according to claim 19, further comprising a housing that houses the winch, wherein:

the housing is configured to facilitate movement of the mount and the spool about the rotation axis, with respect to the housing, the housing defines a longitudinal track along a track axis, parallel with the rotation axis, and the track is configured to facilitate, upon rotation of the mount in the forward rotational direction, longitudinal movement of the eyelet along the track axis.

* * * * *